(12) United States Patent
Haque et al.

(10) Patent No.: US 11,712,222 B2
(45) Date of Patent: Aug. 1, 2023

(54) CONFIGURABLE ULTRASONIC IMAGER

(71) Applicant: eXo Imaging, Inc., Redwood City, CA (US)

(72) Inventors: Yusuf Haque, Woodside, CA (US); Sandeep Akkaraju, Wellesley, MA (US); Janusz Bryzek, Oakland, CA (US); Brian Bircumshaw, Orinda, CA (US)

(73) Assignee: EXO IMAGING, INC., Santa Clara, CA (US)

( * ) Notice: Subject to any disclaimer, the term of this patent is extended or adjusted under 35 U.S.C. 154(b) by 273 days.

(21) Appl. No.: 17/067,139

(22) Filed: Oct. 9, 2020

(65) Prior Publication Data

US 2021/0022707 A1 Jan. 28, 2021

Related U.S. Application Data

(62) Division of application No. 15/826,606, filed on Nov. 29, 2017, now Pat. No. 10,835,209.
(Continued)

(51) Int. Cl.
*B06B 1/06* (2006.01)
*H10N 30/00* (2023.01)
(Continued)

(52) U.S. Cl.
CPC .......... *A61B 8/4494* (2013.01); *A61B 8/0883* (2013.01); *A61B 8/145* (2013.01);
(Continued)

(58) Field of Classification Search
CPC ... A61B 8/4494; A61B 8/0883; A61B 8/4488; A61B 8/461; A61B 8/5207; A61B 8/546;
(Continued)

(56) References Cited

U.S. PATENT DOCUMENTS 4,211,949 A 7/1980 Brisken et al.
4,281,298 A 7/1981 Gounji et al.
(Continued)

FOREIGN PATENT DOCUMENTS

EP 2745137 A1 6/2014
EP 3453056 A1 3/2019
(Continued)

OTHER PUBLICATIONS

PCT/US2019/051238 International Search Report and Written Opinion dated Dec. 19, 2019.
(Continued)

*Primary Examiner* — J. San Martin
(74) *Attorney, Agent, or Firm* — Morgan, Lewis & Bockius LLP

(57) ABSTRACT

An imaging device includes a two dimensional array of piezoelectric elements. Each piezoelectric element includes: a piezoelectric layer; a bottom electrode disposed on a bottom side of the piezoelectric layer and configured to receive a transmit signal during a transmit mode and develop an electrical charge during a receive mode; and a first top electrode disposed on a top side of the piezoelectric layer; and a first conductor, wherein the first top electrodes of a portion of the piezoelectric elements in a first column of the two dimensional array are electrically coupled to the first conductor.

13 Claims, 36 Drawing Sheets

Related U.S. Application Data

(60) Provisional application No. 62/433,782, filed on Dec. 13, 2016, provisional application No. 62/429,833, filed on Dec. 4, 2016, provisional application No. 62/429,832, filed on Dec. 4, 2016.

(51) Int. Cl.
| | |
|---|---|
| A61B 8/00 | (2006.01) |
| G01S 7/52 | (2006.01) |
| H10N 30/88 | (2023.01) |
| H10N 30/20 | (2023.01) |
| A61B 8/08 | (2006.01) |
| A61B 8/14 | (2006.01) |
| B06B 1/02 | (2006.01) |
| G01S 7/521 | (2006.01) |
| G01S 15/89 | (2006.01) |

(52) U.S. Cl.
CPC .......... *A61B 8/4483* (2013.01); *A61B 8/4488* (2013.01); *A61B 8/461* (2013.01); *A61B 8/488* (2013.01); *A61B 8/5207* (2013.01); *A61B 8/546* (2013.01); *B06B 1/0215* (2013.01); *B06B 1/0238* (2013.01); *B06B 1/0629* (2013.01); *B06B 1/0662* (2013.01); *B06B 1/0692* (2013.01); *G01S 7/521* (2013.01); *G01S 7/52046* (2013.01); *G01S 7/52079* (2013.01); *G01S 15/8925* (2013.01); *H10N 30/1051* (2023.02); *H10N 30/2047* (2023.02); *H10N 30/2048* (2023.02); *H10N 30/88* (2023.02); *A61B 8/4427* (2013.01); *A61B 8/4472* (2013.01); *B06B 2201/76* (2013.01)

(58) Field of Classification Search
CPC ..... A61B 8/4483; A61B 8/488; A61B 8/4427; A61B 8/4472; B06B 1/0662; B06B 1/0215; B06B 1/0692; H01L 41/053; H01L 41/098; G01S 7/52079; G01S 7/8925

See application file for complete search history.

(56) References Cited

U.S. PATENT DOCUMENTS

| | | | |
|---|---|---|---|
| 4,375,042 A | 2/1983 | Marcus | |
| 4,731,865 A | 3/1988 | Sievenpiper | |
| 5,520,187 A | 5/1996 | Snyder | |
| 5,605,154 A | 2/1997 | Ries et al. | |
| 5,969,621 A | 10/1999 | Getman et al. | |
| 6,023,977 A | 2/2000 | Langdon et al. | |
| 6,083,168 A | 7/2000 | Hossack et al. | |
| 6,108,121 A | 8/2000 | Mansell et al. | |
| 6,359,367 B1 | 3/2002 | Sumanaweera et al. | |
| 7,005,776 B1 | 2/2006 | Iino et al. | |
| 7,532,093 B1 | 5/2009 | Pulskamp et al. | |
| 8,004,158 B2 | 8/2011 | Hielscher | |
| 10,548,565 B2 | 2/2020 | Kinnon et al. | |
| 10,835,209 B2 | 11/2020 | Haque et al. | |
| 2001/0005776 A1 | 6/2001 | Holley et al. | |
| 2003/0178914 A1 | 9/2003 | Ogawa et al. | |
| 2003/0181814 A1 | 9/2003 | Ji et al. | |
| 2004/0195937 A1 | 10/2004 | Matsubara et al. | |
| 2005/0025377 A1 | 2/2005 | Avinash et al. | |
| 2005/0228282 A1 | 10/2005 | Wang et al. | |
| 2006/0113866 A1 | 6/2006 | Ganor | |
| 2006/0122486 A1 | 6/2006 | Tamez-Pena et al. | |
| 2006/0173313 A1 | 8/2006 | Liu et al. | |
| 2007/0167752 A1 | 7/2007 | Proulx et al. | |
| 2007/0242567 A1 | 10/2007 | Daft et al. | |
| 2008/0255451 A1 | 10/2008 | Cohen et al. | |
| 2010/0020645 A1 | 1/2010 | Wodnicki et al. | |
| 2010/0168583 A1 | 7/2010 | Dausch et al. | |
| 2010/0266186 A1 | 10/2010 | Hebrank et al. | |
| 2011/0051461 A1 | 3/2011 | Buchwald et al. | |
| 2011/0249878 A1 | 10/2011 | Pagoulatos et al. | |
| 2012/0116220 A1 | 5/2012 | Burcher et al. | |
| 2012/0127136 A1 | 5/2012 | Schneider et al. | |
| 2012/0146642 A1 | 6/2012 | Du | |
| 2012/0232397 A1 | 9/2012 | Ohshima | |
| 2013/0158397 A1 | 6/2013 | Srinivas et al. | |
| 2013/0206962 A1 | 8/2013 | Barr et al. | |
| 2013/0303919 A1 | 11/2013 | Corl | |
| 2014/0024928 A1 | 1/2014 | Boctor et al. | |
| 2014/0031694 A1* | 1/2014 | Solek | B06B 1/0622 600/459 |
| 2014/0117812 A1 | 5/2014 | Hajati | |
| 2014/0155747 A1 | 6/2014 | Bennett et al. | |
| 2014/0211592 A1 | 7/2014 | Miyazawa | |
| 2014/0219063 A1 | 8/2014 | Hajati et al. | |
| 2014/0328504 A1 | 11/2014 | Stephanou et al. | |
| 2014/0355377 A1 | 12/2014 | Hiriyannaiah | |
| 2015/0023561 A1 | 1/2015 | Hamilton | |
| 2015/0097468 A1 | 4/2015 | Hajati et al. | |
| 2015/0160322 A1 | 6/2015 | Matthews | |
| 2015/0182196 A1 | 7/2015 | Ninomiya et al. | |
| 2015/0265245 A1 | 9/2015 | Von Ramm et al. | |
| 2015/0333730 A1 | 11/2015 | Meltaus et al. | |
| 2016/0107194 A1 | 4/2016 | Panchawagh et al. | |
| 2016/0157818 A1 | 6/2016 | Cho et al. | |
| 2016/0211828 A1 | 7/2016 | Simmonds et al. | |
| 2016/0262725 A1 | 9/2016 | Boser et al. | |
| 2016/0288168 A1 | 10/2016 | Hynynen et al. | |
| 2016/0331353 A1 | 11/2016 | Ralston et al. | |
| 2017/0000461 A1 | 1/2017 | Wong et al. | |
| 2017/0119349 A1* | 5/2017 | Miyazawa | A61B 8/4494 |
| 2017/0224312 A1 | 8/2017 | Call et al. | |
| 2017/0262598 A1 | 9/2017 | Petkov et al. | |
| 2017/0328870 A1 | 11/2017 | Garlepp et al. | |
| 2018/0153510 A1 | 6/2018 | Haque et al. | |
| 2018/0154393 A1 | 6/2018 | Viegas et al. | |
| 2018/0192999 A1 | 7/2018 | Song et al. | |
| 2019/0184426 A1 | 6/2019 | Kojima et al. | |
| 2019/0316957 A1 | 10/2019 | Akkaraju et al. | |
| 2019/0343485 A1 | 11/2019 | Shepard et al. | |
| 2020/0046320 A1* | 2/2020 | Wodnicki | H01L 41/1132 |
| 2021/0022706 A1 | 1/2021 | Haque et al. | |
| 2021/0196989 A1 | 7/2021 | Rinaldi et al. | |

FOREIGN PATENT DOCUMENTS

| | | | |
|---|---|---|---|
| JP | | 2004141328 A | 5/2004 |
| JP | | 2007512870 A | 5/2007 |
| JP | | 2008272471 A | 11/2008 |
| JP | | 2009535097 A | 10/2009 |
| JP | | 2010050888 A | 3/2010 |
| JP | | 2010142637 A | 7/2010 |
| JP | | 2011015423 A | 1/2011 |
| JP | | 2012139491 A | 7/2012 |
| JP | | 2012187296 A | 10/2012 |
| JP | | 2014124427 A | 7/2014 |
| JP | | 2014144100 A | 8/2014 |
| JP | | 2014528219 A | 10/2014 |
| JP | | 2015520975 A | 7/2015 |
| JP | | 2015211726 A | 11/2015 |
| JP | | 2016503312 A | 2/2016 |
| JP | | 2016507273 A | 3/2016 |
| WO | | WO-2013044471 A1 | 4/2013 |
| WO | | WO-2015086413 A1 | 6/2015 |
| WO | | WO-2014050280 A1 | 8/2016 |
| WO | | WO-2018102621 A1 | 6/2018 |
| WO | | WO-2018102622 A1 | 6/2018 |
| WO | | WO-2019182771 A1 | 9/2019 |
| WO | | WO-2020068473 A1 | 4/2020 |
| WO | | WO-2020139775 A1 | 7/2020 |

OTHER PUBLICATIONS

PCTUS2021014141 Communication dated Apr. 14, 2021 and International Search Report/Written Opinion dated Apr. 8, 2021.

(56) References Cited

OTHER PUBLICATIONS

U.S. Appl. No. 15/826,614 Ex Parte Quayle Action dated Apr. 22, 2021.
APC International, Ceramic manufacturing series—poling PZT ceramics. https://www.americanpiezo.com/blog/ceramic-manufacturing-series-poling-pzt-ceramics/ [1-3] (2016).
Assef et al., A reconfigurable arbitrary waveform generator using PWM modulation for ultrasound research. BioMedical Engineering OnLine 12:24 [1-13] (2013).
Choudhry et al., Comparison of tissue harmonic imaging with conventional US in abdominal disease. RadioGraphics: Imaging and Therapeutic Technology 20:1127-1135 (2000).
Dahl, Ultrasound beamforming and image formation, http://people.duke.edu/-jjd/RSNA_USbeamforming.pdf [Slide presentation] (c. 2005).
Dausch et al., Theory and operation of 2-D array piezoelectric micromachined ultrasound transducers. IEEE Transactions on Ultrasonics, Ferroelectrics, and Frequency Control 55(11):2484-2492 (2008).
Doerry, Generating nonlinear FM chirp waveforms for radar. Sandia Report, SAND2006-5856:1-34 (2006).
Felix et al., Biplane ultrasound arrays with integrated multiplexing solution for enhanced diagnostic accuracy in endorectal and transvaginal imaging. http://www.vermon.com/vermon/publications/Felix_UFFC_2005.pdf (2005).
Goldman, Apple's Lightning connector and you: what you should know. CNET Sep. 19, 2012: https://www.cnet.com/news/apples-lightning-connector-and-you-what-you-should-know/ (2012).
Guedes et al., Aluminum nitride pMUT based on a flexurally-suspended membrane. IEEE 16th International Solid-State Sensors, Actuators and Microsystems Conference:12169346 (2011).
Hajati et al.,Three-dimensional micro electromechanical system piezoelectric ultrasound transducer. Appl. Phys. Lett. 101:253101 (2012); doi: 10.1063/1.4772469 (2012).
Harput, Use of chirps in medical ultrasound imaging. Ultrasound Group, School of Electronic and Electrical Engineering, University Of Leeds, PhD Thesis, Dec. 2012.
Karki, Signal conditioning piezoelectric sensors. Texas Instruments Application report, SLA033A:1-5 (2000).
Khuri-Yakub et al., Capacitive micro machined ultrasonic transducers for medical imaging and therapy. Journal of Micromech Microeng. 21(5):054004-054014 (2011).
Lach et al., Piezoelectric materials for ultrasonic probes. http://www.ndt.net/article/platte2/platte2.htm NDTnet 1 (9):1-9 (1996).
Lee et al., Wafer-to-wafer alignment for three-dimensional integration: a review. Journal of MicroElectroMechanical Systems 20(4):885-898 (2011).
Lu et al., High frequency piezoelectric micromachined ultrasonic transducer array for intravascular ultrasound imaging. Proceedings of the IEEE International Conference on Micro Electro Mechanical Systems (MEMS):06765748 (2014).
Martin, Introduction to B-mode imaging. Cambridge University Press; Diagnostic Ultrasound: Physics and equipment, 2nd Edition. Chapter 1:1-10 (2010).
Mina, High frequency transducers from PZT films. Materials Science and Engineering Thesis; Pennsylvania State University:1-199 (2007).
Moazzami et al., Electrical characteristics of ferroelectric PZT thin films for DRAM applications. IEEE Transaction on Electron Devices 39(9):2044-2049 (1992).
Orenstein Scanning in pain—sonographers seek relief from job-related hazard. Radiology Today 10(8):24 (2009).
Ovland, Coherent plane-wave compounding in medical ultrasound imaging. NTNU-Trondheim, Norwegian University of Science and Technology, Master of Science Thesis, 1-62 (Jun. 2012).
PCT/US2017/064090 International Search Report and Written Opinion dated Mar. 28, 2018.
PCT/US2017/064091 International Search Report and Written Opinion dated Mar. 28, 2018.
PCT/US2019/068004 International Search Report and Written Opinion dated Apr. 21, 2020.
Pye et al., Adaptive time gain compensation for ultrasonic imaging. Ultrasound in Medicine and Biology 18(2):205-212 [abstract] (1992).
Rodriguez et al., Low cost matching network for ultrasonic transducers. Physics Procedia 3:1025-1031 (2010).
Smyth, Design and modeling of a PZT thin film based piezoelectric micromachined ultrasonic transducer (PMUT). MSME Thesis, MIT:1-156 (2012).
Spectral doppler. http://www.echocardiographer.org/Echo%20Physics/spectral%20doppler.html (2017).
Szabo. Diagnostic ultrasound imaging: inside out. ELSEVIER Academic Press, ISBN: 0-12-680145-2 (572 pgs) (2014).
Trots et al., Synthetic aperture method in ultrasound imaging. InTech Press; Ultrasound Imaging, Masayuki Tanabe (Ed.). http://www.intechopen.com/books/ultrasound-imaging/synthetic-aperture-method-in-ultrasound-imaging. Chapter 3:37-56 (2011).
U.S. Appl. No. 15/826,614 Office Action dated Oct. 1, 2020.
Wang et al., Broadband piezoelectric micromachined ultrasonic transducer (pMUT) using mode-merged design. Proceedings of the 10th IEEE International Conference on Nano/Micro Engineered and Molecular Systems (IEEE-NEMS 2015):15260900. Xi'an, China, Apr. 7-11, 2015.
Wang et al., Zero-bending piezoelectric micromachined ultrasonic transducer (pMUT) with enhanced transmitting performance. Journal of Microelectromechanical Systems 24(6):2083-2091 (2015).

* cited by examiner

CONFIGURABLE ULTRASONIC IMAGER

CROSS REFERENCE TO RELATED APPLICATIONS

This application is a Divisional of U.S. patent application Ser. No. 15/826,606 filed on Nov. 29, 2017, which claims the benefit of U.S. Provisional Application Nos. 62/429,832, filed on Dec. 4, 2016, entitled "A Configurable Ultrasonic Line imager," 62/429,833, filed on Dec. 4, 2016, entitled "Low Voltage, Low Power MEMS Transducer with Direct Interconnect," and 62/433,782, filed on Dec. 13, 2016, entitled "Micromachined Transceiver Array," which are hereby incorporated by reference in their entirety.

BACKGROUND

A. Technical Field

The present invention relates to imaging devices, and more particularly, to imaging devices having configurable ultrasonic line imagers.

B. Background of the Invention

A non-intrusive imaging system/probe for imaging internal tissue, bones, blood flow or organs of human or animal body and displaying the images requires transmission of a signal into the body and receiving an emitted or reflected signal from the body part being imaged. Typically, transducers that are used in an imaging system are referred to as transceivers and some of the transceivers are based on photo-acoustic or ultrasonic effects. In general, the transceivers are used for imaging, but are not necessarily limited to imaging. For example, the transceivers can be used in medical imaging, flow measurements in pipes, speaker and microphone arrays, lithotripsy, localized tissue heating for therapeutics or highly intensive focused ultrasound (HIFU) for surgery. The conventional transducers built from bulk piezoelectric (PZT) material typically require very high voltage pulses to generate transmission signals, typically 100 V or more. This high voltage results in high power dissipation, since the power consumption/dissipation in the transducers is proportional to the square of the drive voltage. There is also a limit on how hot the surface of the probe could be and this limits how much power could be consumed in the probe, since the consumed power is proportional to the heat generated by the probe. In the conventional systems, the heat generation has necessitated cooling arrangements for some probes, increasing the manufacturing costs and weights of the probes. In general, the weight of the conventional probe is also an issue, since a large number of sonographers, who use these probes, are known to suffer from muscular injuries.

The conventional ultrasound probes in use for medical imaging typically use PZT material or other piezo ceramic and polymer composites. Probes typically house the transducers and some other electronics with means to cause an image to be displayed on a display unit. To fabricate the conventional bulk PZT elements for the transducers, one can simply cut a thick piezoelectric material slab into large rectangular shaped PZT elements. These rectangular shaped PZT elements are very expensive to build, since the manufacturing process involves precisely cutting of the rectangular shaped thick PZT or ceramic material and mounting on substrates with precise spacing. Further, the impedance of the transducers is much higher than the impedance of the transmit/receive electronics for the transducers.

In the conventional systems, the transmit/receive electronics for the transducers often are located far away from the probe, requiring micro-coax cables between the transducers and electronics. In general, the cables need to have a precise length for delay and impedance matching, and, quite often, additional impedance matching networks are required for efficient connection of the transducers through the cables to the electronics.

Advances in micro-machining technologies allow sensors and actuators, such as capacitive micromachined ultrasound transducers (cMUTs) and piezoelectric micromachined ultrasound transducers (pMUTs), to be efficiently formed on a substrate. Compared to the conventional transducers having bulky piezoelectric material, pMUTs are less bulky and cheaper to manufacture while they have simpler and higher performance interconnection between electronics and transducers, provide greater flexibility in the operational frequency, and potential to generate higher quality images.

Although the basic concepts for these transducers have been disclosed in the early 1990's, commercial implementation of these concepts has met with a number of challenges. For instance, the conventional cMUT sensors are particularly prone to failure or drift in performance due to the charge build-up during the high voltage operation, difficulty with generating high enough acoustic pressure at lower frequencies and are inherently nonlinear. The conventional pMUTs have been a promising alternative but have issues related to transmission and receive inefficiencies, still required relatively high operating voltages and had limited bandwidth As such, there is a need for pMUTs that have an enhanced efficiency, that can operate at lower voltages and exhibit high bandwidth.

SUMMARY OF THE DISCLOSURE

In embodiments, an imaging device includes a two dimensional array of piezoelectric elements. Each piezoelectric element includes: a piezoelectric layer; a bottom electrode disposed on a bottom side of the piezoelectric layer and configured to receive a transmit signal during a transmit mode and develop an electrical charge during a receive mode; and a first top electrode disposed on a top side of the piezoelectric layer; and a first conductor, where the first top electrodes of a portion of the piezoelectric elements in a first column of the two dimensional array are electrically coupled to the first conductor.

In embodiments, an imaging device includes: a two dimensional array of piezoelectric elements, each piezoelectric element of the two dimensional array of piezoelectric elements including at least one sub piezoelectric element and including: a piezoelectric layer; a bottom electrode disposed on a bottom side of the piezoelectric layer; and first and second top electrodes disposed on a top side of the piezoelectric layer; and a first conductor, the first top electrodes of a portion of piezoelectric elements in a first column of the two dimensional array being electrically coupled to the first conductor; a first electrical circuit electrically coupled to the first conductor and configured to process a signal received through the first conductor; a second conductor, the second top electrodes of a portion of piezoelectric elements in a second column of the two dimensional array being electrically coupled to the second conductor; a switch having first and second ends, the first end being electrically coupled to the second conductor; a second electrical circuit for processing a signal; a transmit driver for sending a signal to the second conductor; and the second end of the switch selectively coupled to one of the second electrical circuit and the transmit driver.

In embodiments, an imaging device includes: a two dimensional array of piezoelectric elements, each piezoelectric element of the two dimensional array of piezoelectric elements including at least one sub piezoelectric element and comprising: a piezoelectric layer; a bottom electrode disposed on a bottom side of the piezoelectric layer; and first and second top electrodes disposed on a top side of the piezoelectric layer; and a first conductor, the first top electrodes of a portion of piezoelectric elements in a first row of the two dimensional array being electrically coupled to the first conductor; a first electrical circuit electrically coupled to the first conductor and configured to process a signal received through the first conductor; a second conductor, the second top electrodes of a portion of piezoelectric elements in a first column of the two dimensional array being electrically coupled to the second conductor; a switch having first and second ends, the first end being electrically coupled to the second conductor; a second electrical circuit for processing a signal; a transmit driver for sending a signal to the second conductor; and the second end of the switch selectively coupled to one of the second electrical circuit and the transmit driver.

In embodiments, an imaging device includes a transceiver substrate and an application-specific integrated circuit (ASIC) chip. The transceiver substrate includes: a two dimensional array of piezoelectric elements, each piezoelectric element of the two dimensional array of piezoelectric elements comprising: a piezoelectric layer; a bottom electrode disposed on a bottom side of the piezoelectric layer; first and second top electrodes disposed on a top side of the piezoelectric layer; and first and second conductors electrically coupled to the first and second top electrodes, respectively. The ASIC chip includes: a two dimensional array of circuit elements, each circuit element of the two dimensional array of circuit elements comprising: a first electrical circuit electrically coupled to the first conductor of a piezoelectric element and configured to process a signal received through the first conductor; a switch having first and second ends, the first end being electrically coupled to the second conductor of a piezoelectric element; a second electrical circuit for processing a signal; a transmit driver for sending a signal to the second conductor; and the second end of the switch selectively coupled to one of the second electrical circuit and the transmit driver.

In embodiments, an electrical circuit for controlling a plurality of piezoelectric elements includes: a first conductor for transmitting a driving signal to one or more of the plurality of piezoelectric elements therethrough during a transmit mode; and a second conductor for transmitting a sensor signal from one or more of the plurality of piezoelectric elements therethrough during a receive mode. Each circuit element of the plurality of circuit elements includes: a first switch having a first end electrically coupled to the second conductor and a first electrode of a piezoelectric element; a second switch having first and second ends, the first end of the second switch being electrically coupled to the first conductor; a transmit driver electrically coupled to the second end of the second switch and configured to transmit a signal to a first electrode of a piezoelectric element upon receiving a signal through the second end of the second switch; and a third switch having first and second ends, the first end of the third switch being electrically coupled to the second end of the second switch, the second end of the third switch being electrically coupled to an electrode of a piezoelectric element.

In embodiments, a method for poling a piezoelectric element that is electrically coupled to an application-specific integrated circuit (ASIC) chip and includes a bottom electrode, a piezoelectric layer disposed on the bottom electrode, first and second top electrodes disposed on the piezoelectric layer, includes the steps of: electrically connecting the bottom electrode to a ground; applying a positive voltage to the first top electrode; applying a negative voltage to the second top electrode; and subjecting the piezoelectric element to a temperature for an extended period of time so that a first portion of the piezoelectric layer under the first top electrode is poled in a first direction and a second portion of the piezoelectric layer under the second top electrode is poled in a second direction that is opposite to the first direction.

In embodiments, an imaging device includes: a two dimensional array of piezoelectric elements, each piezoelectric element including at least one sub piezoelectric element and comprising: a piezoelectric layer; a bottom electrode disposed on a bottom side of the piezoelectric layer; and a first top electrode disposed on a top side of the piezoelectric layer; and an application-specific integrated circuit (ASIC) chip comprising an array of circuits for driving the two dimensional array of piezoelectric elements, each of the circuits being electrically coupled to a corresponding piezoelectric element, wherein a first line imager including a portion of piezoelectric elements in a first column of the two dimensional array is formed by simultaneously turning on a portion of the circuits that control the portion of the piezoelectric elements in the first column of the two dimensional array.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

FIG. 19A-1 shows a top view of a transceiver substrate and an ASIC chip according to embodiments of the present disclosure.

FIG. 19A-2 shows a side view of an imaging assembly according to embodiments of the present disclosure.

FIG. 19B-1 shows a top view of a transceiver substrate and an ASIC chip according to embodiments of the present disclosure.

FIG. 19B-2 shows a side view of an imaging assembly according to embodiments of the present disclosure.

DETAILED DESCRIPTION OF THE PREFERRED EMBODIMENTS

In the following description, for purposes of explanation, specific details are set forth in order to provide an understanding of the disclosure. It will be apparent, however, to one skilled in the art that the disclosure can be practiced without these details. Furthermore, one skilled in the art will recognize that embodiments of the present disclosure, described below, may be implemented in a variety of ways, such as a process, an apparatus, a system, a device, or a method on a tangible computer-readable medium.

One skilled in the art shall recognize: (1) that certain fabrication steps may optionally be performed; (2) that steps may not be limited to the specific order set forth herein; and (3) that certain steps may be performed in different orders, including being done contemporaneously.

Elements/components shown in diagrams are illustrative of exemplary embodiments of the disclosure and are meant to avoid obscuring the disclosure. Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments. The terms "include," "including," "comprise," and "comprising" shall be understood to be open terms and any lists that follow are examples and not meant to be limited to the listed items. Any headings used herein are for organizational purposes only and shall not be used to limit the scope of the description or the claims. Furthermore, the use of certain terms in various places in the specification is for illustration and should not be construed as limiting.

In embodiments, the pMUT transducers and transducer assemblies may be used for generating images of internal organs of a human/animal body as well as other therapeutic applications where ultrasonic beams are used to heat tissue for healing or focus high power ultrasonic beams for micro surgery. In embodiments, the piezoelectric elements may also be used for tomography applications.

In embodiments, the manufacturing cost of pMUTs may be reduced by applying modern semiconductor and wafer processing techniques. In embodiments, thin film piezoelectric layer may be spun on or sputtered onto semiconductor wafers and later patterned to create piezoelectric sensors that each have two or more electrodes. In embodiment, each piezoelectric element may be designed to have the ability to emit or receive signals at a certain frequency, known as center frequency, as well as the second and/or additional frequencies. Hereinafter, the terms piezoelectric element, pMUT, transceiver, and pixel are used interchangeably.

Figure 1:
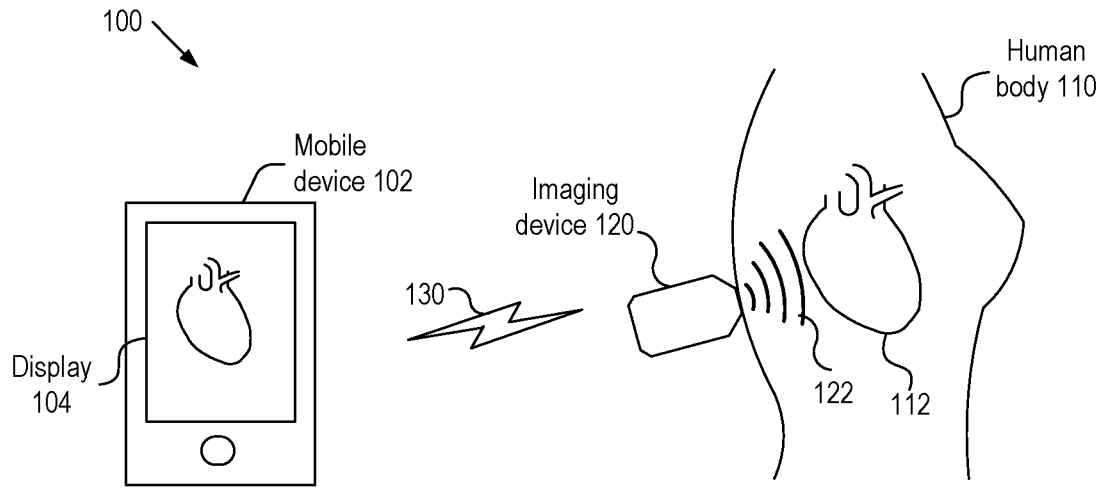
FIG. 1 shows a schematic diagram of an imaging system according to embodiments of the present disclosure.

FIG. 1 shows a schematic diagram of an imaging system 100 according to embodiments of the present disclosure. As depicted, the system 100 may include: an imager 120 that generates and transmits pressure waves 122 toward an internal organ 112, such as heart, in a transmit mode/process; and a device 102 that sends and receives signals to the imager through a communication channel 130. In embodiments, the internal organ 112 may reflect a portion of the pressure waves 122 toward the imager 120, and the imager 120 may capture the reflected pressure waves and generate electrical signals in a receive mode/process. The imager 120 may communicate electrical signals to the device 102 and the device 102 may display images of the organ or target on a display/screen 104 using the electrical signals.

In embodiment, the imager 120 may be used to perform one dimensional imaging, also known as A-Scan, two dimensional imaging, also known as B scan, three dimensional imaging, also sometimes referred to as C scan, and Doppler imaging. Also, the imager may be switched to various imaging modes under program control.

In embodiments, the imager 120 may be used to get an image of internal organs of an animal, too. The imager 120 may also be used to determine direction and velocity of blood flow in arteries and veins as in Doppler mode imaging and also measure tissue stiffness. In embodiments, the pressure wave 122 may be acoustic, ultrasonic, or photo-acoustic waves that can travel through the human/animal body and be reflected by the internal organs, tissue or arteries and veins.

In embodiments, the imager 120 may be a portable device and communicate signals through the communication channel 130, either wirelessly (using a protocol, such as 802.11 protocol) or via a cable (such as USB2, USB 3, USB 3.1, and USB-C), with the device 102. In embodiments, the device 102 may be a mobile device, such as cell phone or iPad, or a stationary computing device that can display images to a user.

In embodiments, an imager may be configured to simultaneously transmit and receive ultrasonic waveforms. Certain piezoelectric elements may be configured to send pressure waves toward the target organ being imaged while other piezoelectric elements may receive the pressure waves reflected from the target organ and develop electrical charges in response to the received waves.

Figure 2:
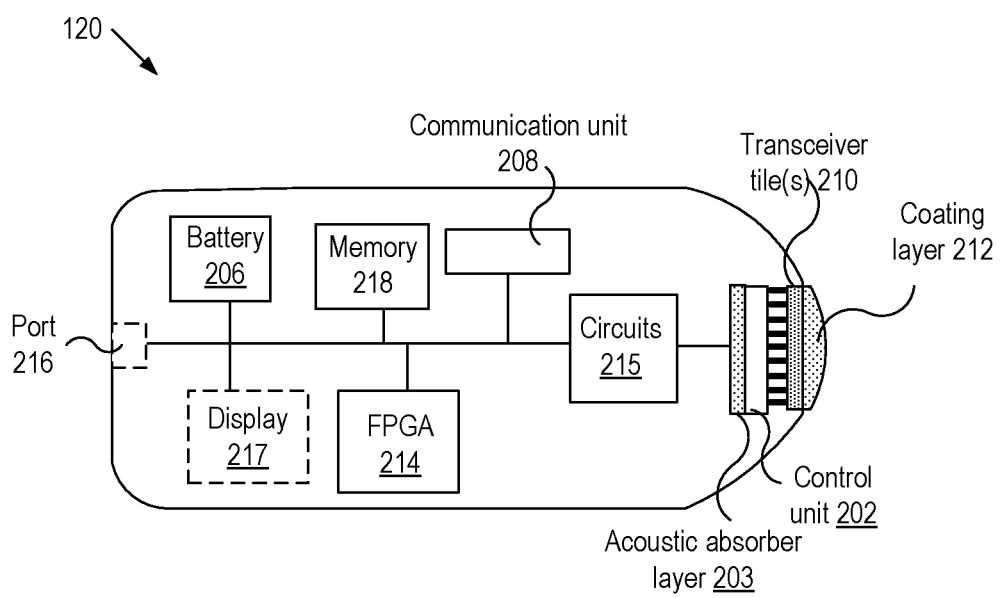
FIG. 2 shows a schematic diagram of an ultrasonic imager according to embodiments of the present disclosure.

FIG. 2 shows a schematic diagram of the imager 120 according to embodiments of the present disclosure. In embodiments, the imager 120 may be an ultrasonic imager. As depicted in FIG. 2, the imager 120 may include: a transceiver tile(s) 210 for transmitting and receiving pressure waves; a coating layer 212 that operates as a lens for steering the propagation direction of and/or focusing the pressure waves and also functions as an impedance interface between the transceiver tile and the human body 110; a control unit 202, such as ASIC chip (or, shortly ASIC), for controlling the transceiver tile(s) 210 and coupled to the transducer tile 210 by bumps; Field Programmable Gate Arrays (FPGAs) 214 for controlling the components of the imager 120; a circuit(s) 215, such as Analogue Front End (AFE), for processing/conditioning signals; an acoustic absorber layer 203 for absorbing waves that are generated by the transducer tiles 210 and propagate toward the circuit 215; a communication unit 208 for communicating data with an external device, such as the device 102, through one or more ports 216; a memory 218 for storing data; a battery 206 for providing electrical power to the components of the imager; and optionally a display 217 for displaying images of the target organs.

In embodiments, the device 102 may have a display/screen. In such a case, the display may not be included in the imager 120. In embodiments, the imager 120 may receive electrical power from the device 102 through one of the ports 230. In such a case, the imager 120 may not include the battery 206. It is noted that one or more of the components of the imager 120 may be combined into one integral electrical element. Likewise, each component of the imager 120 may be implemented in one or more electrical elements.

In embodiments, the user may apply gel on the skin of the human body 110 before the body 110 makes a direct contact with the coating layer 212 so that the impedance matching at the interface between the coating layer 212 and the human body 110 may be improved, i.e., the loss of the pressure wave 122 at the interface is reduced and the loss of the reflected wave travelling toward the imager 120 is also reduced at the interface. In embodiments, the transceiver tiles 210 may be mounted on a substrate and may be attached to an acoustic absorber layer. This layer absorbs any ultrasonic signals that are emitted in the reverse direction, which may otherwise be reflected and interfere with the quality of the image.

As discussed below, the coating layer 212 may be only a flat matching layer just to maximize transmission of acoustic signals from the transducer to the body and vice versa. In embodiments, the thickness of the coating layer 212 may be a quarter wavelength of the pressure wave generated by the transducer tile(s) 202. Beam focus in the elevation direction, which is along the direction of the length of the column, is not essential in this case, because it can be electronically implemented in control unit 202. Even then, the lens may be designed with a focus in some cases. The imager 120 may use the reflected signal to create an image of the organ 112 and results may be displayed on a screen in a variety of format, such as graphs, plots, and statistics shown with or without the images of the organ 112.

In embodiments, the control unit 202, such as ASIC, may be assembled as one unit together with the transceiver tiles. In other embodiments, the control unit 202 may be located outside the imager 120 and electrically coupled to the transceiver tile 210 via a cable. In embodiments, the imager 120 may include a housing that encloses the components 202-215 and a heat dissipation mechanism for dissipating heat energy generated by the components.

Figure 3A:
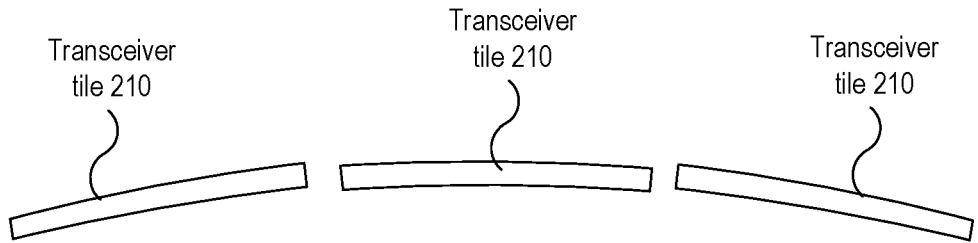
FIG. 3A shows a side views of an exemplary transceiver array according to embodiments of the present disclosure.
Figure 3B:
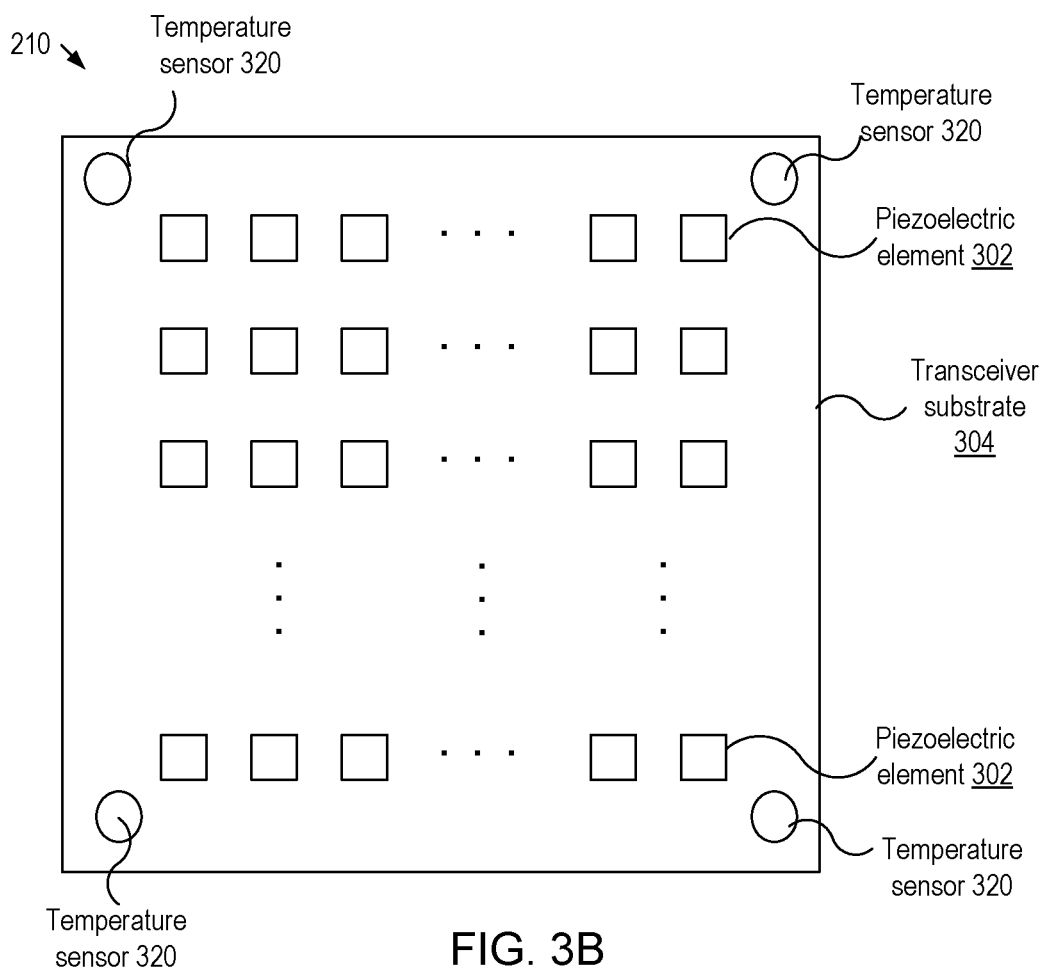
FIG. 3B shows a top view of a transceiver tile according to embodiments of the present disclosure.

FIG. 3A shows a schematic diagram of an exemplary transceiver array having three transceiver tiles 210 according to embodiments of the present disclosure. The tiles may be on a planar surface or on a curved surface. FIG. 3B shows a top view of the transceiver tile 210 that includes one or more piezoelectric elements 302 according to embodiments of the present disclosure. As depicted, the transceiver tile 210 may include a transceiver substrate 304 and one or more piezoelectric elements 302 arranged on the transceiver substrate 304.

Unlike the conventional systems that use bulk piezoelectric elements, in embodiments, the pMUT array 302 may be formed on a wafer and the wafer may be diced to form multiple transceiver tiles 210. This process may reduce the manufacturing cost since the transceiver tiles 210 may be fabricated in high volume and at low cost. In embodiments, the diameter of the wafer may range 6~12 inches and many pMUT arrays may be batch manufactured. Further, in embodiments, as discussed in conjunction with FIGS. 18 and 19, the integrated circuits for controlling the pMUT array 302 may be formed in an ASIC chip so that the pMUT array 302 may be connected to the matching integrated circuits in close proximity, preferably within 25 µm-100 µm. For example, the transceiver tile 210 may have 1024 pMUT elements 302 and be connected to a matching ASIC chip that has the appropriate number of circuits for driving the 1024 pMUT elements 302.

In embodiments, each piezoelectric element 302 may have any suitable shape such as, square, rectangle, and circle, so on. In embodiments, two or more piezoelectric elements may be connected to form a larger pixel element. As depicted in FIG. 3B, when building an imager, it is desirable to have a two dimensional array of piezoelectric element 302, arranged in orthogonal directions. In embodiments, to create a line element, a column of N piezoelectric elements 302 may be connected electrically in parallel. Then, this line element may provide transmission and reception of ultrasonic signals similar to those achieved by a continuous piezoelectric element that is almost N times longer than each element. This line element may be called a column or line or line element interchangeably. It is understood that tiles may be arranged in other shape such as circular, or other shapes. In embodiments, one or more temperature sensors 320 may be installed in the transducer tile 210 to measure the temperature of the tile 210. It is noted that the imager 120 may include one or more temperature sensors for measuring temperatures at various locations of the imager 120.

To mimic a line element of the conventional designs, the shape of a piezoelectric element of a given width may need to be very tall. For example, a line element of a conventional design may be 280 µm in width and 8000 µm tall, while the thickness may be 100 µm. However, on the transceiver tile 210, it is advantageous to design a line element using a plurality of identical piezoelectric elements 302, where each element may have its characteristic center frequency. In embodiments, when a plurality of the piezoelectric elements 302 are connected together, the composite structure (i.e. the line element) may act as one line element with a center frequency that consists of the center frequencies of all the element pixels. In modern semiconductor processes, these center frequencies match well to each other and have a very small deviation from the center frequency of the line element. It is also possible to mix several pixels of somewhat different center frequencies to create a wide bandwidth line compared to lines using only one central frequency.

In embodiments, the piezoelectric elements 302 have a suspended membrane associated with them that vibrates at a center frequency when exposed to stimulus at that frequency and behave like resonators. There is a selectivity associated with these resonators, known as a Q factor. In embodiments, for ultrasound imagers, Q may be usually designed to be low (close 1 or thereabouts) and achieved by a combination of design of the pixels and loading applied to the pixels in actual use. In embodiments, the loading may be provided by application of a layer of RTV or other material to the top face of the piezoelectric elements, where the loading may facilitate closer impedance matching between the transducer surface emitting and receiving the pressure waves and the human body part being imaged. In embodiments, the low Q and the well matched center frequency may allow the line element to essentially act like a line imaging element with substantially one center frequency. In embodiments, loading may also include a matching layer below the transducers, where the emitted waveform is absorbed by an acoustic absorber.

In embodiments, for instance, each piezoelectric element 302 may be spaced 250 µm from each other center to center. Further to simplify, say they are square in shape. Now, let's say, to mimic a conventional line element, a column of the piezoelectric elements 302 may be connected to each other. For example, 24 piezoelectric elements 302 in a column may create a line element of roughly 6 mm in elevation, with each element being 0.25 mm in width. In embodiments, this connection may be achieved at wafer level using a metal interconnect layer.

It is noted that the transceiver tile 210 may include one or more membranes that suspend from the substrate and the piezoelectric elements 302 may be disposed on the membranes. In embodiments, as described below in conjunction with FIGS. 4-8, a membrane may be disposed under each of the piezoelectric elements 302. In embodiments, more than one piezoelectric elements may be disposed on one membrane 309. In embodiments, more than one membrane may be disposed under one of the piezoelectric elements 302. More information on the arrangement of piezoelectric elements on a membrane may be found in a copending U.S. patent application Ser. No. 15/820,319, entitled "Imaging devices having piezoelectric transducers," filed on Nov. 21, 2017, which is herein incorporated by reference in its entirety.

Figure 4:
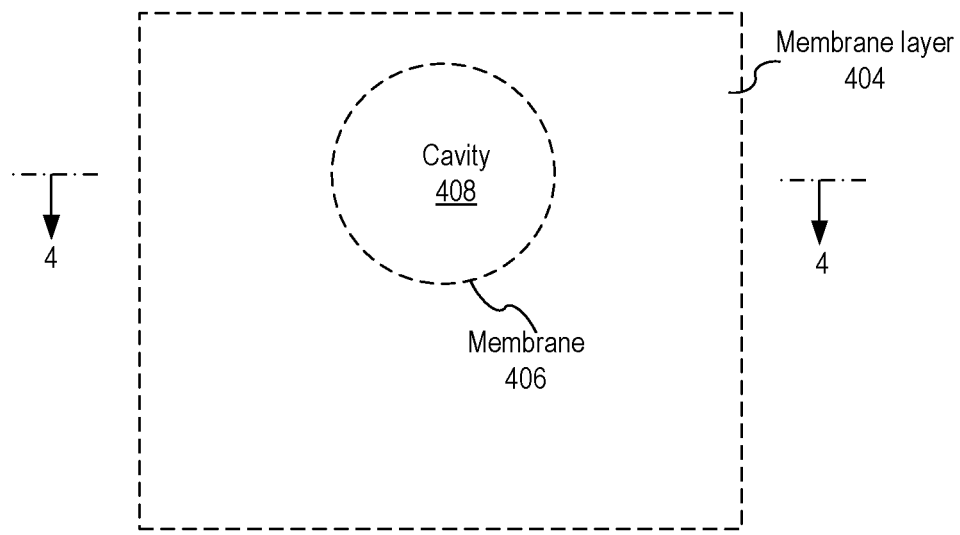
FIG. 4-8 show steps for fabricating an exemplary piezoelectric element according to embodiments of the present disclosure.
Figure 5:
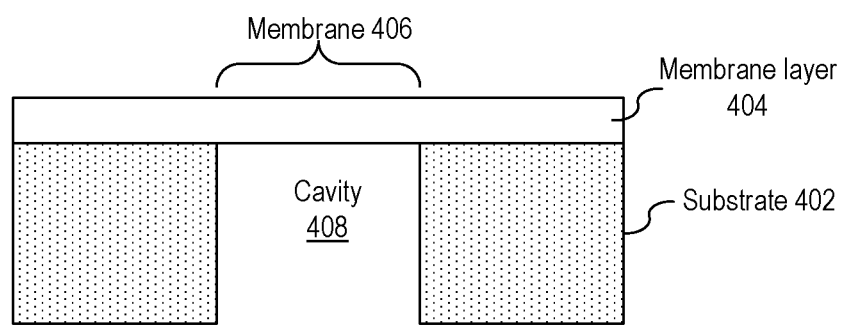

For the conventional bulk piezoelectric elements, the voltage potential across the top and bottom electrodes ranges 100V~200V. For the conventional pMUTs, the voltage potential across the top and bottom electrodes is about 30V. In embodiments, in order to reduce this voltage further, the piezoelectric elements 302 may include a scaled down thin piezoelectric layer, and the piezoelectric layer may have a thickness in the order of 2 µm or less. FIGS. 4-8 show steps for fabricating an exemplary piezoelectric element according to embodiments of the present disclosure. FIG. 4 shows a top view of a membrane 406 disposed on a substrate 402 and FIG. 5 shows a cross sectional view of the membrane and substrate, taken along the line 4-4 according to embodiments of the present disclosure. (In embodiments, the substrate 402 may correspond to the transceiver substrate 304 in FIG. 3B.) As depicted, in embodiments, a membrane layer 404 may be deposited on the substrate 402 and a cavity 408 may be formed to remove a portion of the substrate 402, to thereby form the membrane 406 that may vibrate relative to the substrate 402 in the vertical direction. In embodiment, the cavity 408 may be formed by conventional wafer processing techniques, such as etching. In embodiments, the substrate 402 may be formed of the same material as the membrane layer 404. In alternative embodiments, the substrate 402 may be formed of a different material from the membrane layer 404. It is noted that the cavity 408 may be formed after the other components, such as top conductor (812 in FIG. 8), of the piezoelectric element is formed.

In embodiments, the membrane 406 has a circular projection area. However, it should be apparent to those of ordinary skill in the art that the membrane 406 may have other suitable geometrical shape.

Figure 6:
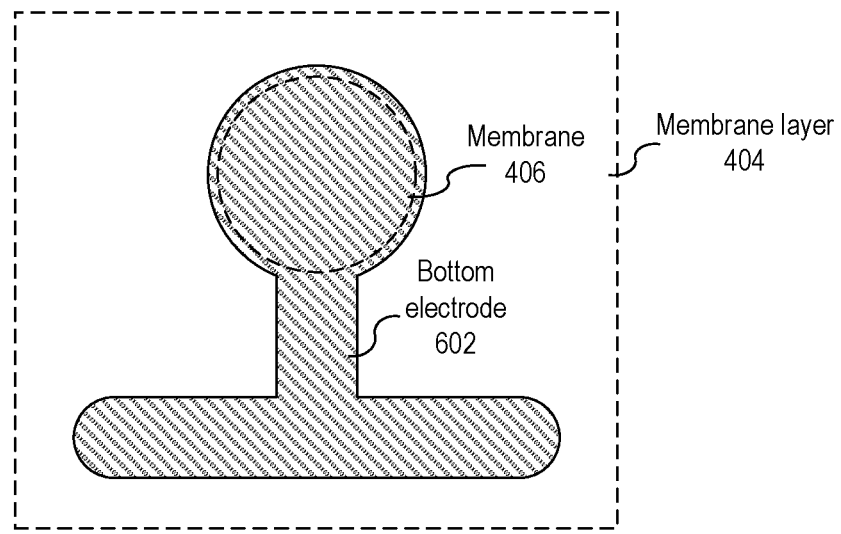
Figure 7:
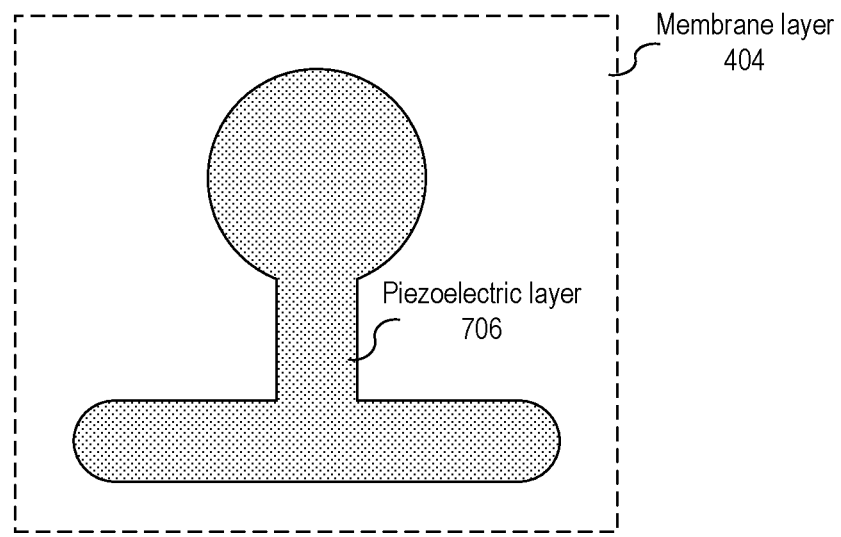

FIG. 6 shows a top view of a bottom electrode 602 disposed on the membrane layer 404 and arranged over the membrane 406 according to embodiments of the present disclosure. FIG. 7 shows a top view of a piezoelectric layer 706 disposed on the bottom electrode 602 according to embodiments of the present disclosure. In embodiments, the piezoelectric layer 706 may have the similar projection area as the bottom electrode 602 so that the piezoelectric layer 706 may cover the entire portion of the bottom electrode 602.

Figure 8:
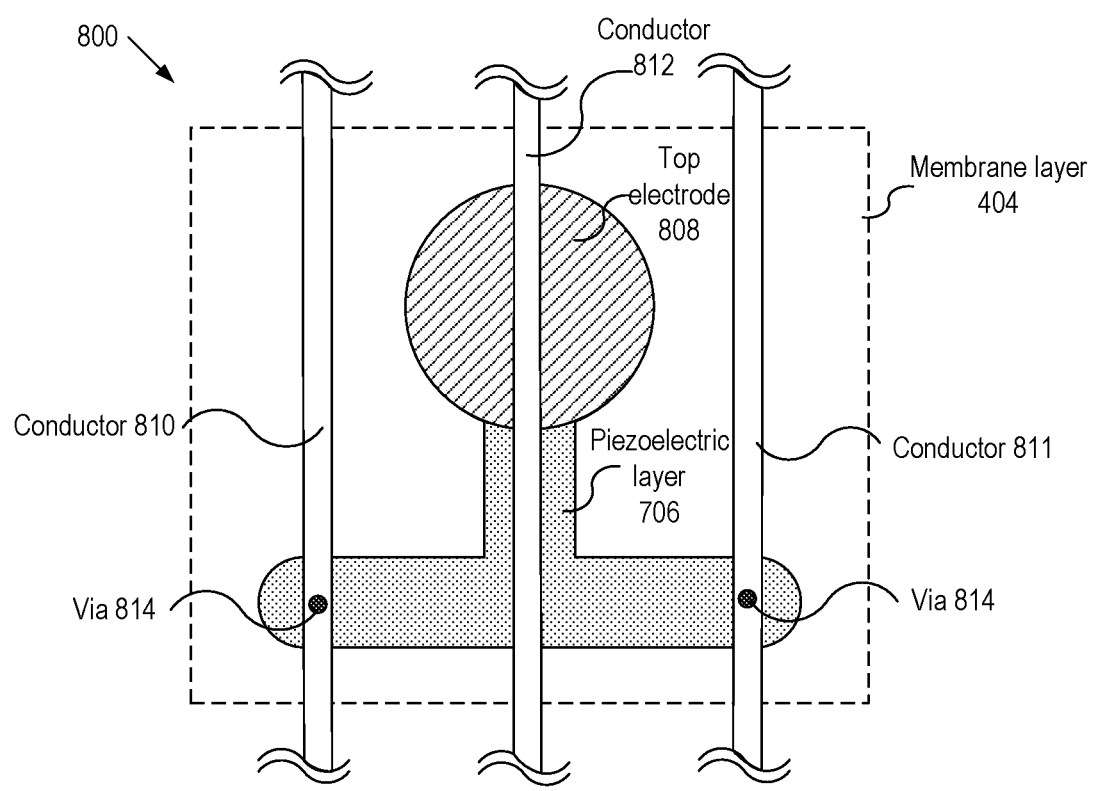

FIG. 8 shows a top view of a piezoelectric element according to embodiments of the present disclosure. As depicted, a top electrode 808 may be disposed on the piezoelectric layer 706 and arranged over the membrane 406. In embodiments, a conductor 812 may be disposed on and electrically coupled to the top electrode 808, while conductors 810 and 811 may reach the bottom electrode 602 through one or more vias 814. In embodiments, the top electrode 808, the piezoelectric layer 706 and the bottom electrode 602 may form a two terminal piezoelectric element and the membrane 406 may vibrate when an electrical voltage is applied across the top and bottom electrodes. In embodiments, electrical charge may be developed in the top and bottom electrodes when the membrane is deformed by a pressure wave during a receive mode/process.

Figure 9:
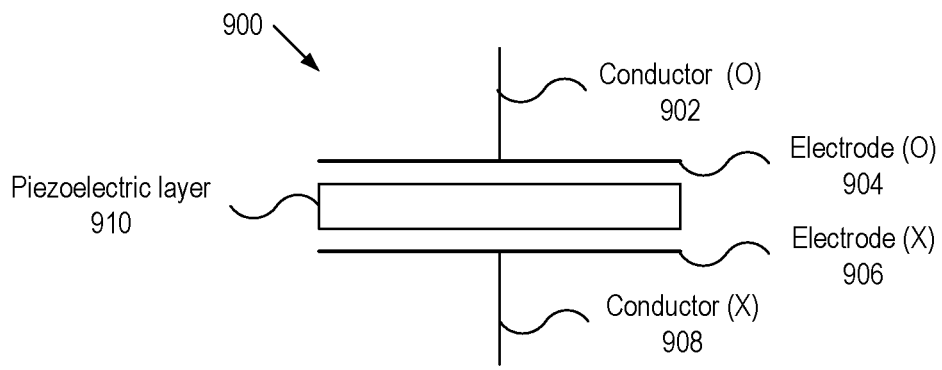
FIG. 9 shows a schematic diagram of a piezoelectric element according to embodiments of the present disclosure.

FIG. 9 shows a schematic diagram of a piezoelectric element 900 according to embodiments of the present disclosure. As depicted, a piezoelectric layer 910 may be disposed between a first electrode (X) 906 and a second electrode (O) 904. In embodiments, the first electrode (X) 906 may be connected to a ground or a DC bias via the conductor (X) 908 and the second electrode (O) 904 may be connected to an electrical circuit (not shown in FIG. 9) through a signal conductor (O) 902. In embodiments, the piezoelectric element 800 in FIG. 8 is an exemplary implementation of the piezoelectric element 900 and the piezoelectric element 900 may be disposed on a membrane layer (such as 404 in FIG. 5).

In the conventional piezoelectric elements, the piezoelectric layer is thick, approaching around 100 µm and typically an AC voltage of +100 to −100 V across the piezoelectric layer is required to create an ultrasonic pressure wave of sufficient strength to enable medical imaging. The frequency of this AC drive signal is typically around the resonating frequency of the piezoelectric structure, and typically above 1 MHz for medical imaging applications. In the conventional systems, the power dissipated in driving the piezoelectric element is proportional to $C*V^2$, where C is capacitance of the piezoelectric element and V is the maximum voltage across the piezoelectric layer. Typically, when transmitting pressure waves, multiple piezoelectric lines are driven together with somewhat different phase delays to focus the pressure waves or to steer a propagation direction of the pressure waves. The simultaneous drive of multiple piezoelectric lines causes the temperature at the surface of the piezoelectric elements to rise. In general, it is highly desirable not to exceed a certain threshold temperature, so as not to injure the subject being imaged. This limits the number of lines that can be driven and the time period for which they can be driven.

In embodiments, the piezoelectric layer 910 is much thinner, approximately 1 to 2 µm thick, compared to the conventional bulk piezoelectric elements. In embodiments, this large reduction in thickness may enable the use of lower voltage drive signals for the piezoelectric element 900, where the voltage is lowered approximately by the amount by which the thickness of the piezoelectric layer 910 is lowered to maintain the similar electric field strength. For example, in embodiments, the voltage potential across the two electrodes 904 and 906 may range from around 1.8 V to 12.6 V peak to peak. The capacitance of the piezoelectric element 900 may increase due to the reduction in thickness of the piezoelectric layer 910 for similar piezoelectric material. For instance, when the drive voltage is decreased by a factor of 10 while the thickness of the piezoelectric layer 910 is also decreased by a factor of 10, the capacitance increases by a factor of 10 and the power dissipation decreases by a factor of 10. This reduction in power dissipation also reduces heat generation and temperature rise in the piezoelectric element. Thus, in embodiments, using lower drive voltages and thinner piezoelectric layer, compared to the conventional piezoelectric elements, the temperature of the pMUT surface may be lowered. Alternately, in embodiments, for a given temperature, more pMUT elements may be driven simultaneously to illuminate the larger target area, compared to the conventional piezoelectric elements. This may allow faster scanning of the target, especially if multiple emissions are needed to scan the entire portion of the target to form one image. In embodiments, a target area may be scanned with multiple emissions using different steering angles and the obtained image data may be combined to obtain a higher quality image.

Compared to the conventional bulk piezoelectric elements, in embodiments, the ability to drive more piezoelectric elements simultaneously may allow more coverage of the transducer aperture per emission, minimizing the number of emissions needed to cover the entire aperture, thus increasing frame rates. A frame rate measures how many times a target is imaged per minute. It is desirable to image at a high frame rate, especially when tissue motion is involved since the moving tissue may make the image blurry. In embodiments, the imager 120 that operates at a higher frame rate may be able to generate images of enhanced quality, compared to the conventional bulk piezoelectric elements.

In embodiments, image quality may be improved by compounding several frames of images into one resultant lower noise frame. In embodiments, by using low voltage and low power pMUTs with a high frame rate, compared to the conventional bulk piezoelectric elements, for a given rise in the pMUT temperature, this averaging technique may be feasible to enhance the image quality. In embodiments, the synthetic aperture method of ultrasound imaging may be used to allow compounding of images. The various frames of images may also be with different steering angles or from orthogonal steering directions to better view the target.

Figure 10A:
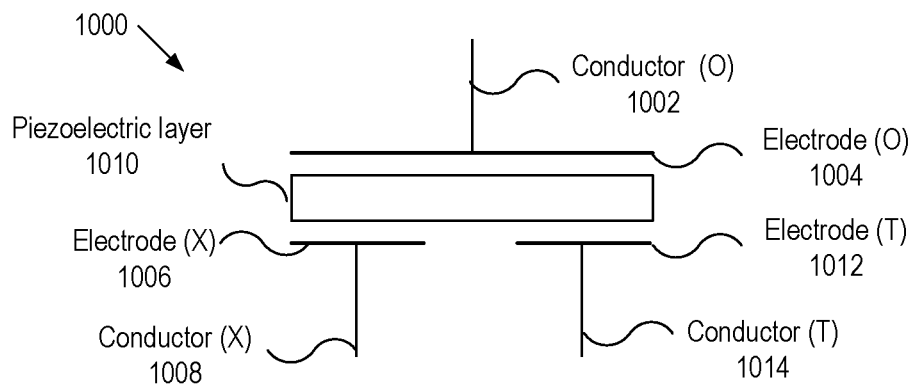
FIG. 10A shows a schematic diagram of a piezoelectric element according to embodiments of the present disclosure.
Figure 10B:
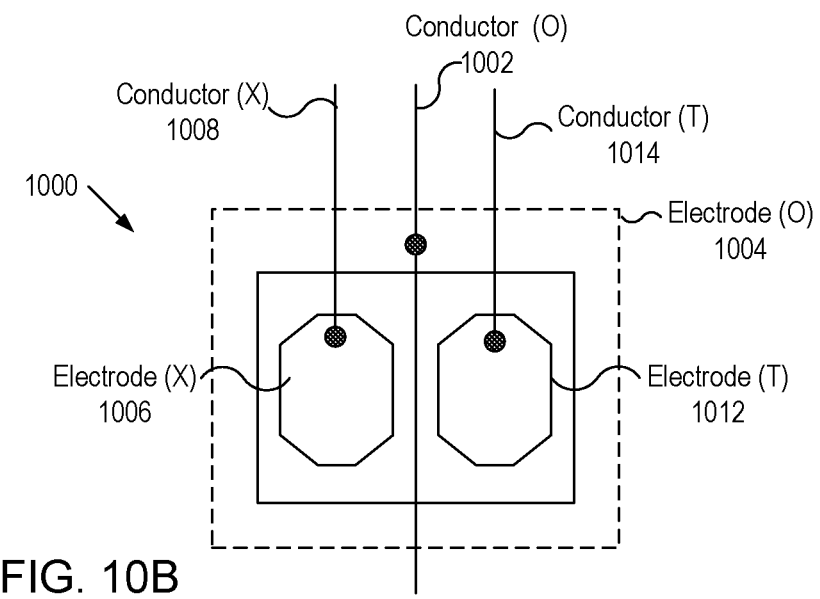
FIG. 10B shows a symbolic representation of the piezoelectric element in FIG. 10A.

FIG. 10A shows a schematic diagram of a piezoelectric element 1000 according to embodiments of the present disclosure. FIG. 10B shows a symbolic representation of the piezoelectric element 1000 in FIG. 10A. As depicted, the piezoelectric element 1000 is similar to the piezoelectric element 900, with the difference that the piezoelectric element 1000 has more than two electrodes. More specifically, the piezoelectric element 1000 may include: a top electrode (O) 100, a first bottom electrode (X) 1006; a second bottom electrode (T) 1012; a piezoelectric layer 1010 disposed between the top and bottom electrodes; and three conductors 1002, 1008 and 1014 that are electrically coupled to the bottom and top electrodes 1004, 1006 and 1012, respectively. (Hereinafter, the terms top and bottom merely refer to two opposite sides of the piezoelectric layer, i.e., the top electrode is not necessarily disposed over the bottom electrode.)

While a unimorph piezoelectric element is shown in FIG. 10A purely for the purpose of illustration, in embodiments, a multiplayer piezoelectric element composed of a plurality of piezoelectric sublayers and electrodes can be utilized. In embodiments, the piezoelectric layer 1010 may include at least one of PZT, PZT-N, PMN-Pt, AlN, Sc—AlN, ZnO, PVDF, and LiNiO$_3$.

Figure 10C:
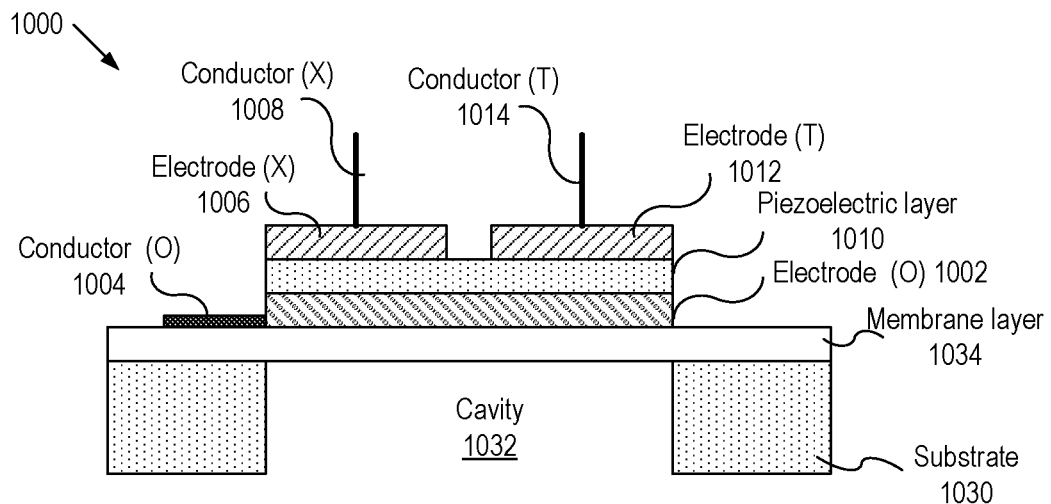
FIG. 10C shows a schematic cross sectional view of an exemplary piezoelectric element according to embodiments of the present disclosure.

FIG. 10C shows a schematic cross sectional diagram of the piezoelectric element 1000 according to embodiments of the present disclosure. As depicted, the piezoelectric element 1000 may be disposed on a membrane layer 1034 that is supported by a substrate 1030. In embodiments, a cavity 1032 may be formed in the substrate 1030 to define a membrane. In embodiments, the membrane layer 1034 may be formed by depositing SiO$_2$ on the substrate 1030.

In embodiments, the piezoelectric element 1000 may include a piezoelectric layer 1010 and a first electrode (O) 1002 that is electrically connected to a signal conductor (O) 1004. In embodiments, the signal conductor (O) 1004 may be formed by depositing TiO$_2$ and metal layers on the membrane layer 1034. In embodiments, the piezoelectric layer 1010 may be formed by the sputtering technique or by the Sol Gel process.

In embodiments, a second electrode (X) 1006 may be grown above the piezoelectric layer 1010 and electrically connected to a second conductor 1008. A third electrode (T) 1012 may be also grown above the piezoelectric layer 1010 and disposed adjacent to the second conductor 1012 but electrically isolated from the second conductor (X) 1008. In embodiments, the second electrode (X) 1006 and third electrode (T) 1012 may be formed by depositing one metal layer on the piezoelectric layer 1010 and patterning the metal layer. In embodiments, the projection areas of the electrodes 1002, 1006 and 1012 may have any suitable shape, such as square, rectangle, circle, and ellipse, so on.

As in the piezoelectric element 1000, the first electrode (O) 1002 may be electrically connected to the conductor (O) 1004 using a metal, a via and interlayer dielectrics. In embodiments, the first electrode (O) 1002 may be in direct contact with the piezoelectric layer 1010. The third conductor (T) 1014 may be deposited or grown on the other side of the piezoelectric layer 1010 with respect to the first electrode (O) 1002.

Figure 10D:
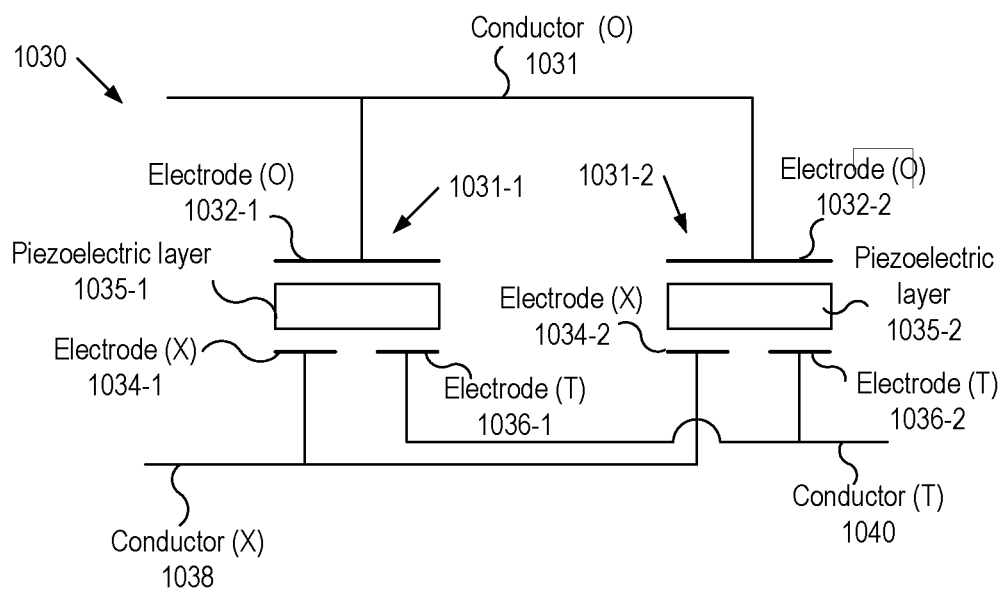
FIG. 10D shows a schematic diagram of a piezoelectric element according to embodiments of the present disclosure.

FIG. 10D shows a schematic diagram of a piezoelectric element 1030 according to embodiments of the present disclosure. As depicted, the piezoelectric element 1030 may include two sub piezoelectric elements (or shortly sub elements) 1031-1 and 1031-2. In embodiments, each sub element may be a three terminal device, i.e. it may have one top electrode 1032-1 (or 1032-2), two bottom electrodes 1034-1 (or 1034-2) and 1036-1 (or 1036-2), and one piezoelectric layer 1035-1 (or 1035-2). In embodiments, the top electrode 1032-1 may be electrically connected to the top electrode 1032-2 by a common conductor (O) 1031, the first bottom electrode (X) 1034-1 may be electrically connected to the first bottom electrode (X) 1034-2 by a common conductor (X) 1038, and the second bottom electrode (T) 1036-1 may be electrically connected to the second bottom electrode (T) 1036-2 by a common conductor (T) 1040. In embodiments, the piezoelectric element 1030 may be disposed on one membrane or each sub element may be disposed on a separate membrane. It should be apparent to those of ordinary skill in the art that the conductor (O) 1032-1 may be electrically connected to the electrode (O) 1031, using metals, vias, interlayer dielectrics (ILD), so on, in the similar manner as the piezoelectric element illustrated in FIGS. 12-16.

Figure 10E:
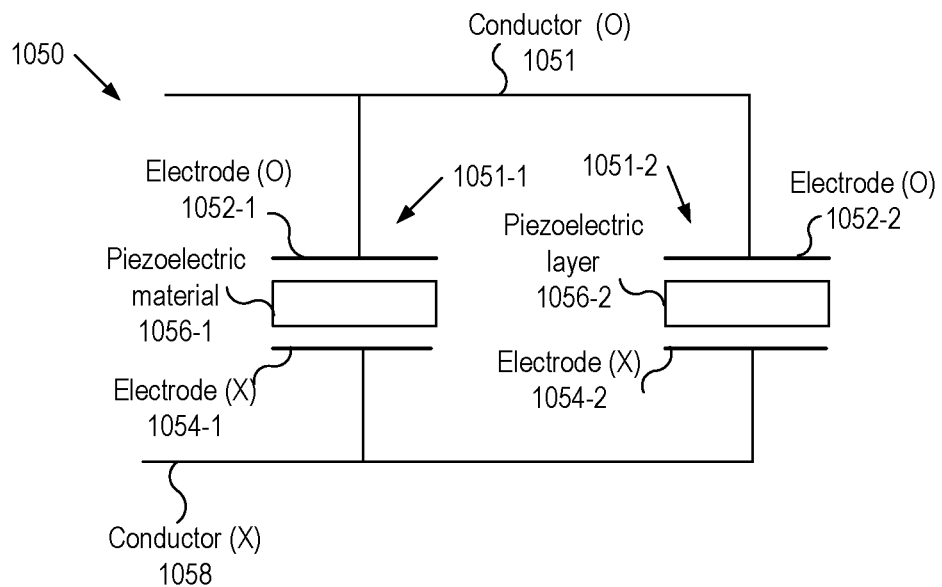
FIG. 10E shows a schematic diagram of a piezoelectric element according to embodiments of the present disclosure.

In embodiments, the conductor (X) 1038 and the conductor (T) 1040 may be all grounded (or connected to a DC bias) during active operation of the imager. In embodiments, the electrodes (O) 1032-1 and 1032-2 may be driven by a common transmit driver circuit and a common electrical signal, typically a signal waveform around the center frequency of the transducer. For example, if the center frequency is 2 MHz, a sinusoidal waveform or square waveform at 2 MHz is applied to the piezoelectric element 1030. This waveform may cause the piezoelectric element 1030 to resonate at 2 MHz and send out a pressure wave, such as 122, from the surface of the transducer. The pressure wave may be reflected from the target organ to be imaged. In embodiments, the reflected pressure wave may hit the piezoelectric element 1030 which is now connected to a signal receiver. The pressure wave may be converted to the electrical charge in the piezoelectric element 1030 by the piezoelectric layers 1035-1 and 1035-2. In embodiments, this charge may be signal processed by amplifiers, filters and eventually digitized by an A/D converter (not shown in FIG. 10D), followed by digital decimators with the data eventually interfaced to FPGAs or Graphical Processing Units (GPUs). These processed signals from multiple piezoelectric elements may be then reconstructed into images. The signal waveform driving the transmit driver can also be a frequency varying signal or a phase varying signal or other complex coded signals, such as chirps or Golay codes FIG. 10E shows a schematic diagram of a piezoelectric element 1050 according to embodiments of the present disclosure. As depicted, the piezoelectric element 1050 may include two sub elements 1051-1 and 1051-2. In embodiments, each sub element may be a two terminal device, i.e. it may have one top electrode 1052-1 (or 1052-2), one bottom electrode 1054-1 (or 1054-2), and one piezoelectric layer 1056-1 (or 1056-2). In embodiments, the top electrode (O) 1052-1 may be electrically connected to the top electrode (O) 1052-2 by a common conductor (O) 1051, and the bottom electrode (X) 1054-1 may be electrically connected to the bottom electrode (X) 1054-2 by a common conductor (X) 1058. In embodiments, the piezoelectric element 1050 may be disposed on one membrane or each sub element may be disposed on a separate membrane.

Figure 10F:
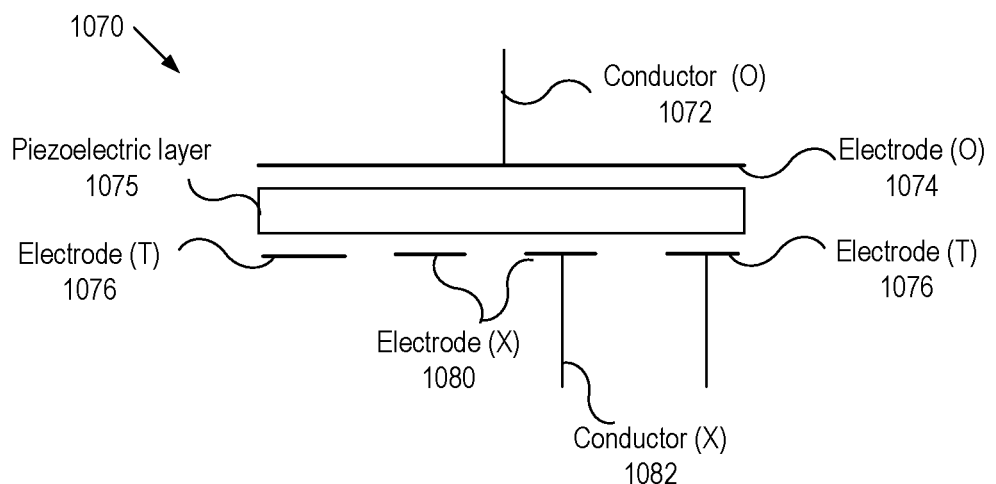
FIG. 10F shows a schematic diagram of a piezoelectric element according to embodiments of the present disclosure.
Figure 10G:
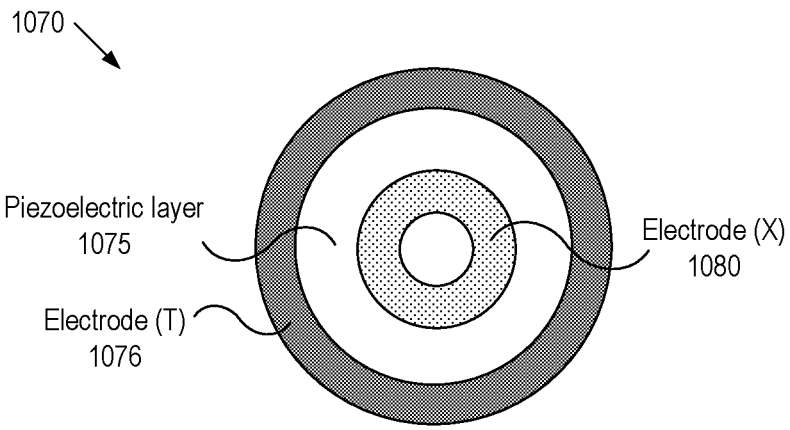
FIG. 10G shows a bottom view of the piezoelectric element in FIG. 10F according to embodiments of the present disclosure.

FIG. 10F shows a schematic diagram of a piezoelectric element 1070 according to embodiments of the present disclosure. FIG. 10G shows a bottom view of the piezoelectric element 1070 according to embodiments of the present disclosure. As depicted, the piezoelectric element 1070 may include: a top electrode (O) 1074, a first bottom electrode (X) 1080; a second bottom electrode (T) 1076; a piezoelectric layer 1075 disposed between the top and bottom electrodes; and three conductors 1072, 1078 and 1082 that are electrically coupled to the bottom and top electrodes 1074, 1076 and 1080, respectively. (In FIG. 10G, the conductors are not shown.) In embodiments, each of the first and second bottom electrodes has an annular shape and the second bottom electrode (X) 1076 surrounds the first bottom electrode (T) 1080.

Figure 10H:
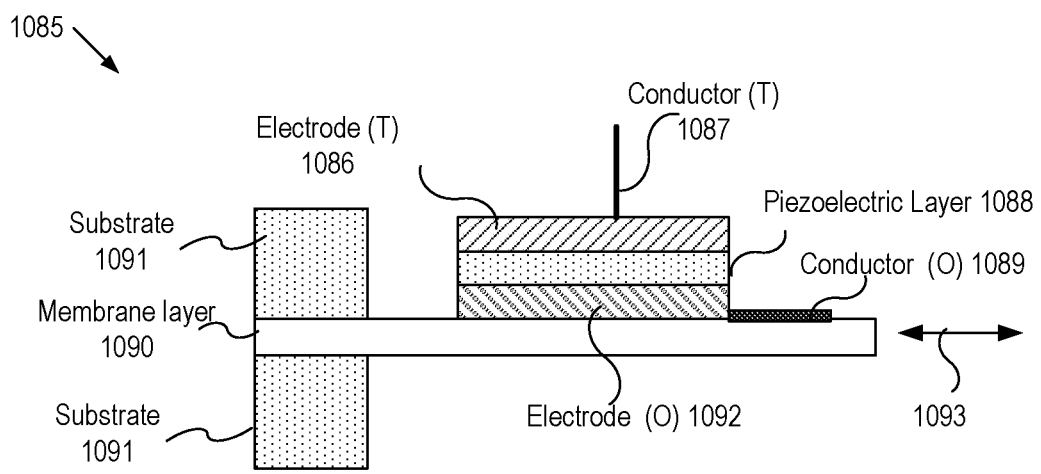
FIG. 10H shows a cross sectional view of the piezoelectric element in FIG. 10F according to embodiments of the present disclosure.

FIG. 10H shows a schematic diagram of a piezoelectric element 1085 according to embodiments of the present disclosure. As depicted, the piezoelectric element 1085 may utilize transverse mode of operation and include: a substrate 1091, a membrane 1090 secured to the substrate at one end; a bottom electrode (O) 1092 that is electrically coupled to a conductor 1089; a piezoelectric layer 1088; and a top electrode 1086 that is electrically coupled to a conductor 1087. In embodiments, the membrane 1090 may be secured to the substrate 1091 at one end so as to vibrate in the transverse mode, as indicated by an arrow 1093, i.e., the piezoelectric element may operate in the transverse mode.

It is noted that the piezoelectric element 1085 may have any suitable number of top electrodes. Also, it is noted that more than one piezoelectric element may be installed on the membrane 1090. It is further noted that the substrate 1091 and membrane 1090 may be formed of one monolithic body and the membrane is formed by etching the substrate.

Figure 11:
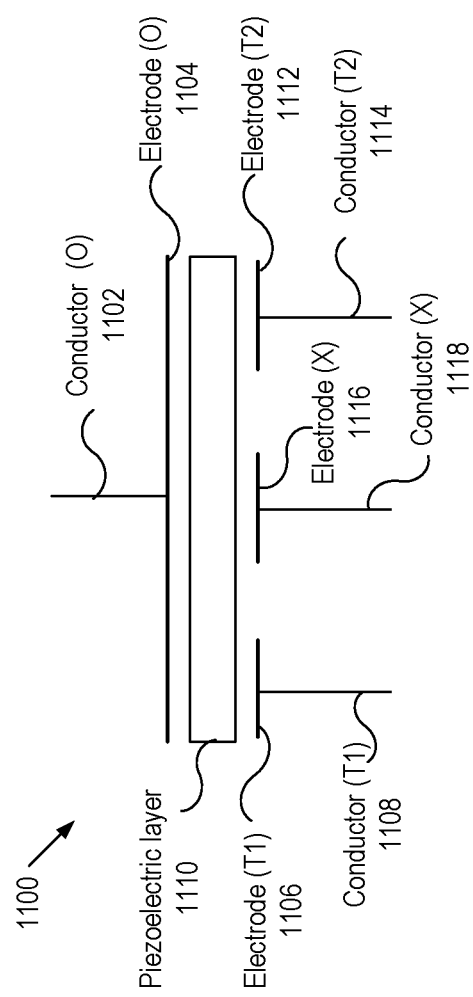
FIG. 11 shows a schematic diagram of a piezoelectric element according to embodiments of the present disclosure.

FIG. 11 shows a schematic diagram of a piezoelectric element 1100 according to embodiments of the present disclosure. As depicted, an electrode (O) 1104 may be disposed on the top surface of a piezoelectric layer 1110 and electrically connected to a conductor (O) 1102 that may be connected to an electric circuit. The conductor (T1) 1108, conductor (T2) 1114 and conductor (X) 1118 may be connected to the bottom electrode (T1) 1106, electrode (T2) 1112 and electrode (X) 1116, respectively. The electrode (T1) 1106, the electrode (X) 1116 and the electrode (T2) 1112 may be disposed on the bottom surface of the piezoelectric layer 1110. In embodiments, the piezoelectric element 1100 may be disposed on one membrane or three separate membranes.

FIGS. 10A-11 show piezoelectric elements (or sub elements) that each have either two terminal (O and X) or three terminals (O, X, and T) or four terminals (O, X, T1 and T2). However, it should be apparent to those of ordinary skill in the art that more than a piezoelectric element (or sub element) may have more than four terminals. For instance, a piezoelectric element may have top bottom (O) electrode and more than three bottom electrodes.

Figure 12:
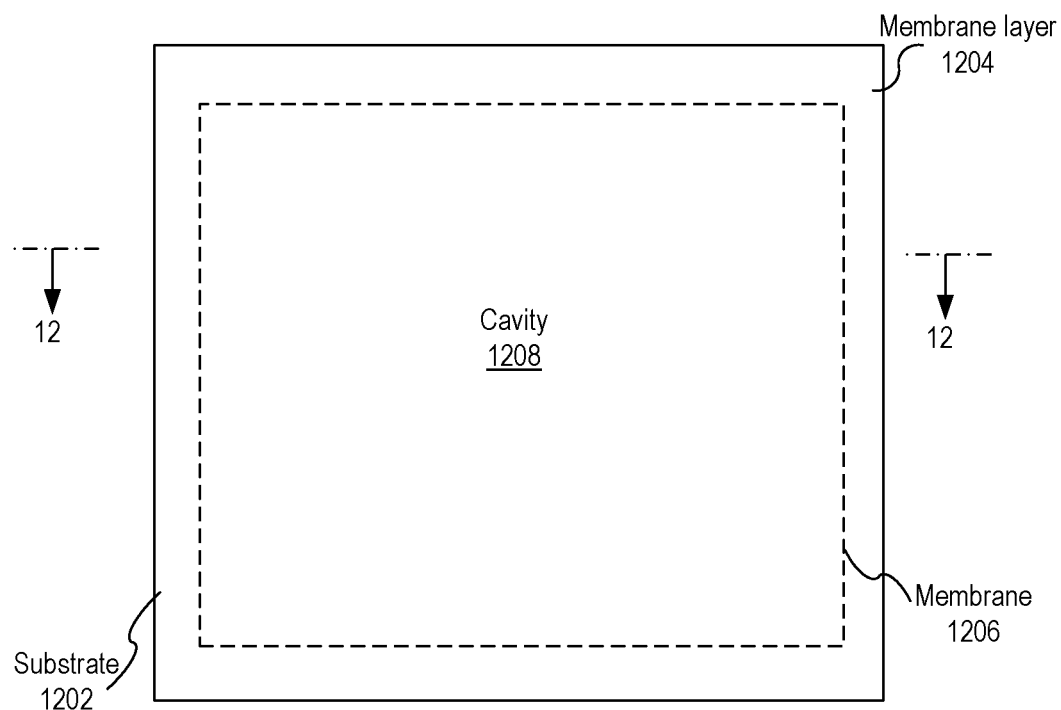
FIG. 12-16 shows steps for fabricating an exemplary piezoelectric element according to embodiments of the present disclosure.
Figure 13:
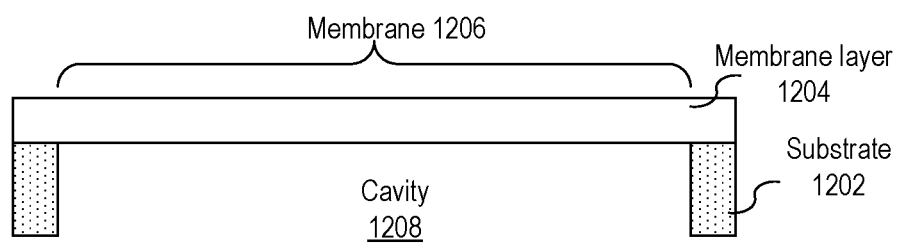

FIG. 12-16 show steps for fabricating an exemplary piezoelectric element that has four terminals according to embodiments of the present disclosure. FIG. 12 show top view of a membrane 1206, which may be formed by forming a membrane layer 1204 on a substrate 1202, and forming a cavity 1208 in the substrate. FIG. 13 shows a cross sectional view of the structure in FIG. 12, taken along the line 12-12. In embodiments, the membrane 1204 may be deposited by a suitable wafer processing technique.

Figure 14:
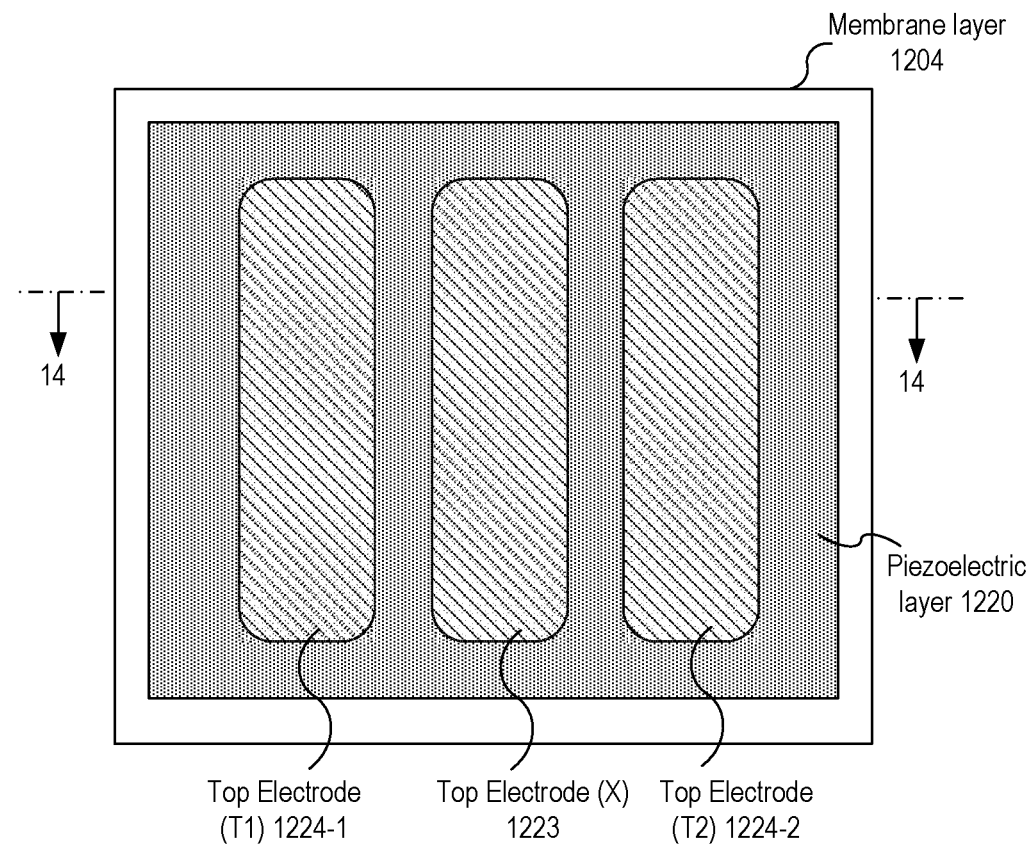
Figure 15:
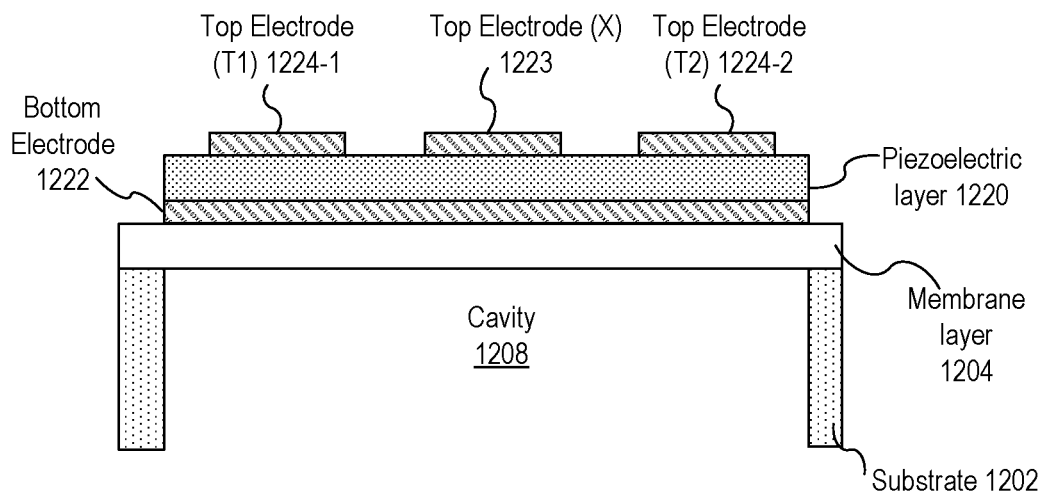

FIG. 14 shows a top view of a layer structure formed on the membrane layer 1204 and FIG. 15 shows a cross sectional view of the layer structure in FIG. 14, taken along the line 14-14, according to embodiments of the present disclosure. As depicted, three top electrodes 1223, 1224-1, and 1224-2, a piezoelectric layer 1220, and a bottom electrode 1222, may be formed on the membrane layer 1204. In embodiments, the top electrodes 1223, 1224-1, and 1224-2, piezoelectric layer 1220, and bottom electrode 1222 may be deposited by suitable wafer processing techniques, such as deposition, sputtering, patterning so on.

Figure 16:
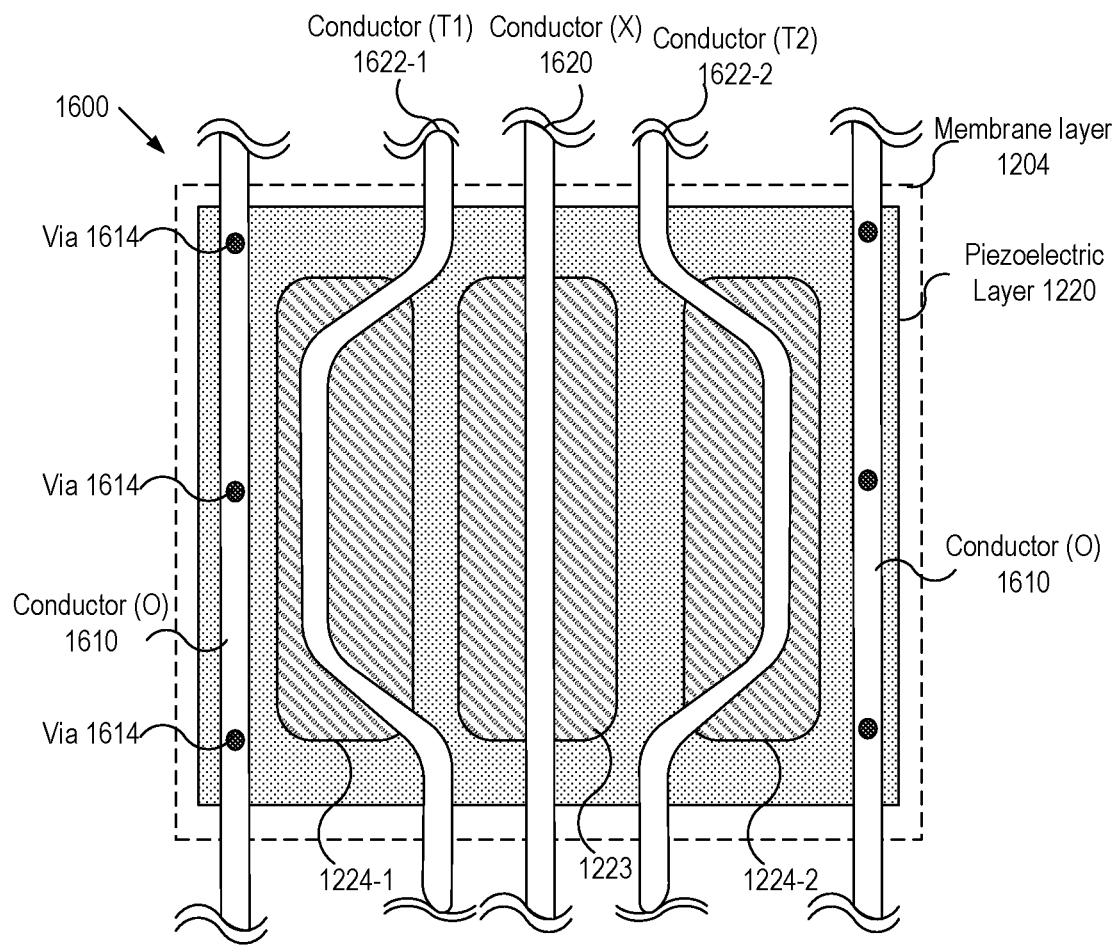

FIG. 16 shows a top view of a piezoelectric element 1600 according to embodiments of the present disclosure. As depicted, three conductors 1620, 1622-1, and 1622-2 may be electrically coupled to the electrodes 1223, 1224-1, and 1224-2, respectively. Also, the conductors (O) 1610 may be electrically coupled to the bottom electrode 1222 through one or more vias 1614. In embodiments, electrical grounds and source planes may be reached to the bottom electrode 1222 through the vias 1614 and the conductors (O) 1610. In embodiments, each of the conductors 1620, 1622-1, and 1622-2 may be connected to the ground or a DC bias voltage. In embodiments, the conductor 1620, may be connected to the ground or a first DC bias voltage, and the conductors 1622-1 and 1622-2 may be connected to the ground or a second DC bias voltage.

Figure 17A:
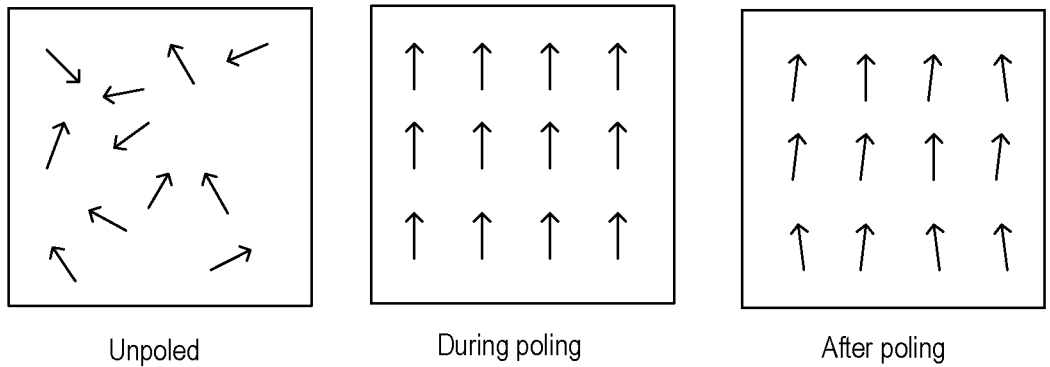
FIG. 17A shows dipole orientations of a piezoelectric material before, during and after a poling process according to embodiments of the present disclosure.

In general, due to the inherent non-symmetry in the crystalline structure of piezoelectric material, an electrical polarity develops, creating electric dipoles. In a macroscopic crystalline structure, the dipoles are by default found to be randomly oriented as shown in FIG. 17A on the left. When the material is subjected to a mechanical stress, each dipole rotates from its original orientation toward a direction that minimizes the overall electrical and mechanical energy stored in the dipole. If all the dipoles are initially randomly oriented (i.e. a net polarization of zero), their rotation may not significantly change the macroscopic net polarization of the material; hence, the piezoelectric effect exhibited will be negligible. Therefore, during an initial state, the dipoles need to be more-or-less oriented in the same direction, which is referred to as poling process. The direction along which the dipoles align is known as the poling direction. FIG. 17 shows dipole orientations of a piezoelectric material before, during and after the poling process according to embodiments of the present disclosure.

As depicted, before the poling process, the individual dipole moments are not aligned. During the poling process, the dipole moments may be aligned to point the same direction. After poling, the dipole moments may remain fairly aligned, although there may still be some elements of random direction. In embodiments, the poling process may be performed by putting the piezoelectric material in a constant electric field at a high temperature to thereby force the dipoles to align.

In embodiments, the piezoelectric element 1000 in FIG. 10A may be poled so that the portions of the piezoelectric layer over the electrode (X) 1006 and electrode (T) 1012 may be poled in opposite directions. This type of poling may result in boosted pressure output for the same transmit voltage, compared to the pressure output that would be obtained using the one poling direction configuration. Also, in embodiments, this type of poling may improve the receive sensitivity, where the reflected pressure waves may be differentially boosted to create a larger charge output, compared to the one poling direction configuration.

Figure 17B:
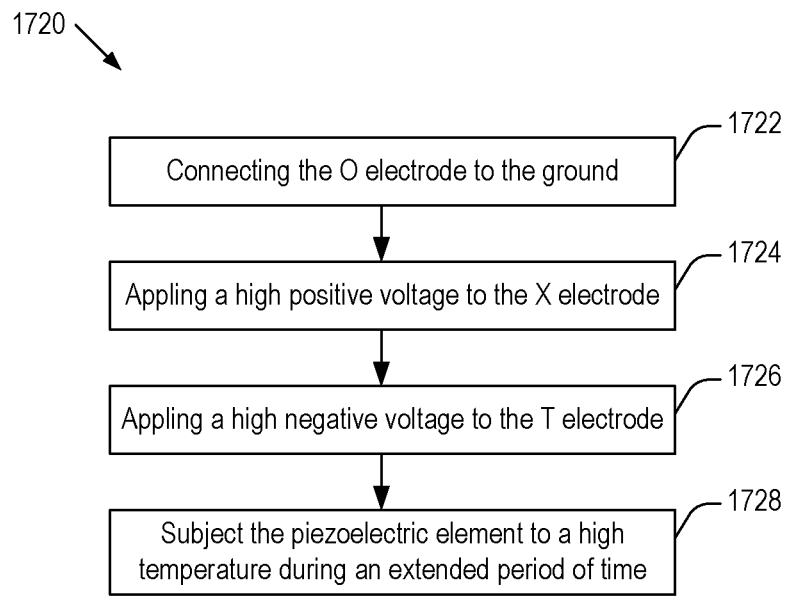
FIG. 17B shows a flow chart of an illustrative process for poling a piezoelectric layer according to embodiments of the present disclosure.

FIG. 17B shows a flow chart of an illustrative process for poling a piezoelectric element 1600 according to embodiments of the present disclosure. To pole the piezoelectric element 1600, the piezoelectric element 1600 may be mounted inside a high temperature chamber (step 1728) and the bottom electrode 1222 may be coupled to the ground (step 1722), while the first top electrode 1224-1 (or 1224-2) may be coupled to a high positive voltage, such as 15 V, (step 1724) and the second top electrode 1223 may be coupled to a high negative voltage, such as −15 V, (step 1726). Then, the piezoelectric element 1600 may be subject to a high temperature inside the chamber for extended period of time (step 1728).

Depending on the polarities of the first and second high voltages, the portions of the piezoelectric layer 1220 under the two electrodes 1224-1 and 1224-2 may be polarized in the same or opposite direction to that of the portion of the piezoelectric layer 1220 under the electrodes 1223. In embodiments, for instance, poling may be implemented by application of high voltages across the electrodes at high temperature, typically 150° C., for 30 minutes for certain piezoelectric materials. For example, for a 1 µm thick piezoelectric layer, +15 V from the signal electrode to the T electrode and −15V from the signal electrode to the X electrode may be applied. Once the piezoelectric material is poled, then each of the X and T electrodes may be grounded or tied to a non-zero DC bias voltage while the conductor (O) 1610 may be connected to an ASIC chip so as to be driven by a transmit driver during the transmit operation or may be connected to an LNA (such as 1811 in FIG. 18A) in the ASIC chip during the receive operation. In embodiments, a DC bias voltage may improve the sensitivity of the piezoelectric element 1600.

Figure 18A:
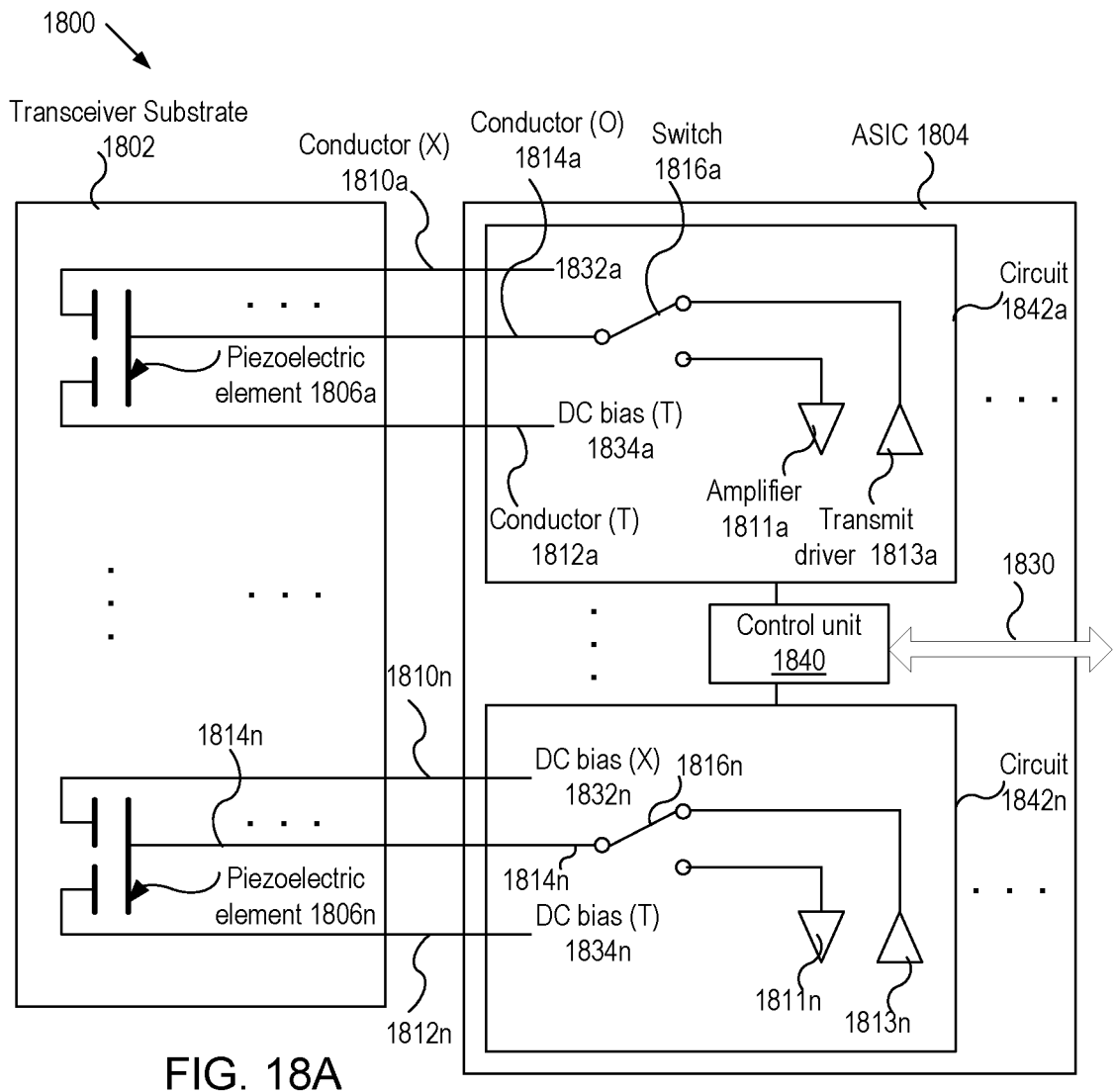
FIG. 18A shows a schematic diagram of an imaging assembly according to embodiments of the present disclosure.

FIG. 18A shows an imaging assembly 1800 according to embodiments of the present disclosure. As depicted, the imaging assembly 1800 may include: a transceiver substrate 1802 (which may be similar to the transceiver tile 210); and an ASIC chip 1804 electrically coupled to the transceiver substrate. In embodiments, the transceiver substrate 1802 may include one or more piezoelectric elements 1806, where each of the piezoelectric element may be disposed on one or more membranes. In embodiments, more than one piezoelectric element may be disposed on one membrane. In embodiments, poling of the piezoelectric layer may be performed after the transceiver substrate 1802 is interconnected to the ASIC chip 1804. It is noted that the ASCI 1804 may be replaced by a suitable substrate that includes multiple circuits for driving the piezoelectric elements 1806 in the transceiver substrate 1802.

In embodiments, poling may be performed on the transceiver tile/substrate 1802 after the transceiver substrate is 3D interconnected to the ASIC chip 1804. In the conventional piezoelectric elements, it is difficult to perform the poling process on a transceiver tile after the transducer tile is coupled to the circuits for driving the piezoelectric elements. It is due to the fact that poling requires application of high voltages to the circuits for controlling the piezoelectric elements and the high voltages may damage the circuits. In contrast, in embodiments, the poling may be performed on the transducer substrate 1802 that is already integrated with the ASIC chip 1804. In embodiments, the ASIC chip 1804 may enable application of desired voltages on all first electrodes of the piezoelectric elements and high voltages may be applied to all second or additional electrodes.

In embodiments, each of the piezoelectric elements 1806a-1806n may have two or more electrodes and these electrodes may be connected to drive/receive electronics housed in the ASIC chip 1804. In embodiments, each piezoelectric element (e.g. 1806a) may include a top conductor that is electrically connected to a conductor (O) (e.g. 1814a) and two bottom electrodes that are electrically connected to conductors (X,T) (e.g. 1810a and 1812a). In embodiments, the conductor 1810a may be electrically coupled to a DC bias (X) 1832a or the ground, and the conductor (T) 1812a may be coupled to a DC bias (T) 1834a or the ground.

In embodiments, the ASIC chip 1804 may include one or more circuits 1842a-1842n that are each electrically coupled to one or more piezoelectric elements 1806a-1806n; and one control unit 1840 for controlling the circuits 1842a-1842n. In embodiments, each circuit (e.g. 1842a) may include a transmit driver (1813a), a receiver amplifier (or shortly amplifier) (e.g. 1811a), a switch (e.g. 1816a) having one terminal electrically coupled to the conductor (O) (1814a) and another terminal that toggles between the two conductors coupled to the transmit driver 1813a and amplifier 1811a. During a transmit (Tx) mode/process, the switch 1816a may connect the transmit driver 1813a to the piezoelectric element 1806a so that a signal is transmitted to the top electrode of the piezoelectric element 1806a. During a receive (Rx) mode/process, the switch 1816a may connect the amplifier 1811a to the piezoelectric element 1806a so that a signal is transmitted from the top electrode of the piezoelectric element 1806a to the amplifier 1811a.

It is noted that the transmit driver 1813a may include various electrical components. However, for brevity, the transmit driver 1813a is represented by one driver. But, it should be apparent to those of ordinary skill in the art that the transmit driver may include a more complex driver with many functions. Electrical components for processing the received signals may be connected to the amplifier 1811a, even though only one amplifier 1811a is shown in FIG. 18A. In embodiments, the amplifier 1811a may be a low noise amplifier (LNA). In embodiments, the circuit 1842n may have the same or similar structure as the circuit 1842a.

In embodiments, all of the DC biases (X) 1832a-1832n may be connected to the same DC bias or the ground, i.e., all of the conductors (X) 1810a-1810n may be connected to a single DC bias or the ground. Similarly, all of the DC biases (X) 1834a-1834n may be connected to the same DC bias or a different DC bias, i.e., all of the conductors (T) 1812a-1812n may be connected to a single DC bias or the ground.

In embodiments, the conductors (X, T and O) 1810, 1812, and 1814 may be connected to the ASIC chip 1804 using an interconnect technology—for instance, copper pillar interconnects or bumps (such as 1882 in FIG. 18B), as indicated by an arrow 1880. In embodiments, the circuitry components in the ASIC chip 1804 may communicate outside the ASIC chip 1804 using an interconnect 1830. In embodiments, the interconnect 1830 may be implemented using bonding wires from pads on the ASIC chip 1804 to another pad outside the ASIC chip. In embodiments, other types of interconnects, such as bump pads or redistribution bumps on the ASIC chip 1804 may be used in addition to wire bonded pads.

In embodiments, the LNAs 1811 included in the circuits 1842 may be implemented outside the ASIC chip 1804, such as part of a receive analog front end (AFE). In embodiments, a LNA may reside in the ASIC chip 1804 and another LNA and programmable gain amplifier (PGA) may reside in the AFE. The gain of each LNA 1811 may be programmed in real time, allowing the LNA to be part of a time gain compensation function (TGC) needed for the imager.

In embodiments, the LNAs 1811 may be built using low voltage transistor technologies and, as such, may be damaged if they are exposed to high transmit voltages that the conventional transducers need. Therefore in the conventional systems, a high voltage transmit/receive switch is used to separate the high transmit voltages from the low voltage receive circuitry. Such a switch may be large and expensive, use High Voltage (HV) processes, and degrade the signal sent to LNA. In contrast, in embodiments, low voltages may be used, and as such, the high voltage components of the conventional system may not be needed any more. Also, in embodiments, by eliminating the conventional HV switch, the performance degradation caused by the conventional HV switch may be avoided.

In embodiments, the piezoelectric elements 1806 may be connected to the LNAs 1811 during the receive mode by the switches 1816. The LNAs 1811 may convert the electrical charge in the piezoelectric elements 1806 generated by the reflected pressure waves exerting pressure on the piezoelectric elements, to an amplified voltage signal with low noise. The signal to noise ratio of the received signal may be among the key factors that determine the quality of the image being reconstructed. It is thus desirable to reduce inherent noise in the LNA itself. In embodiments, the noise may be reduced by increasing the transconductance of the input stage of the LNAs 1811, such as using more current in the input stage. The increase in current may cause the increase in power dissipation and heat. In embodiments, pMUTs 1806 may be operated with low voltages and be in close proximity to the ASIC chip 1804, and as such, the power saved by the low voltage pMUTs 1806 may be utilized to lower noise in the LNAs 1811 for a given total temperature rise acceptable, compared to conventional transducers operated with high voltages.

Figure 18B:
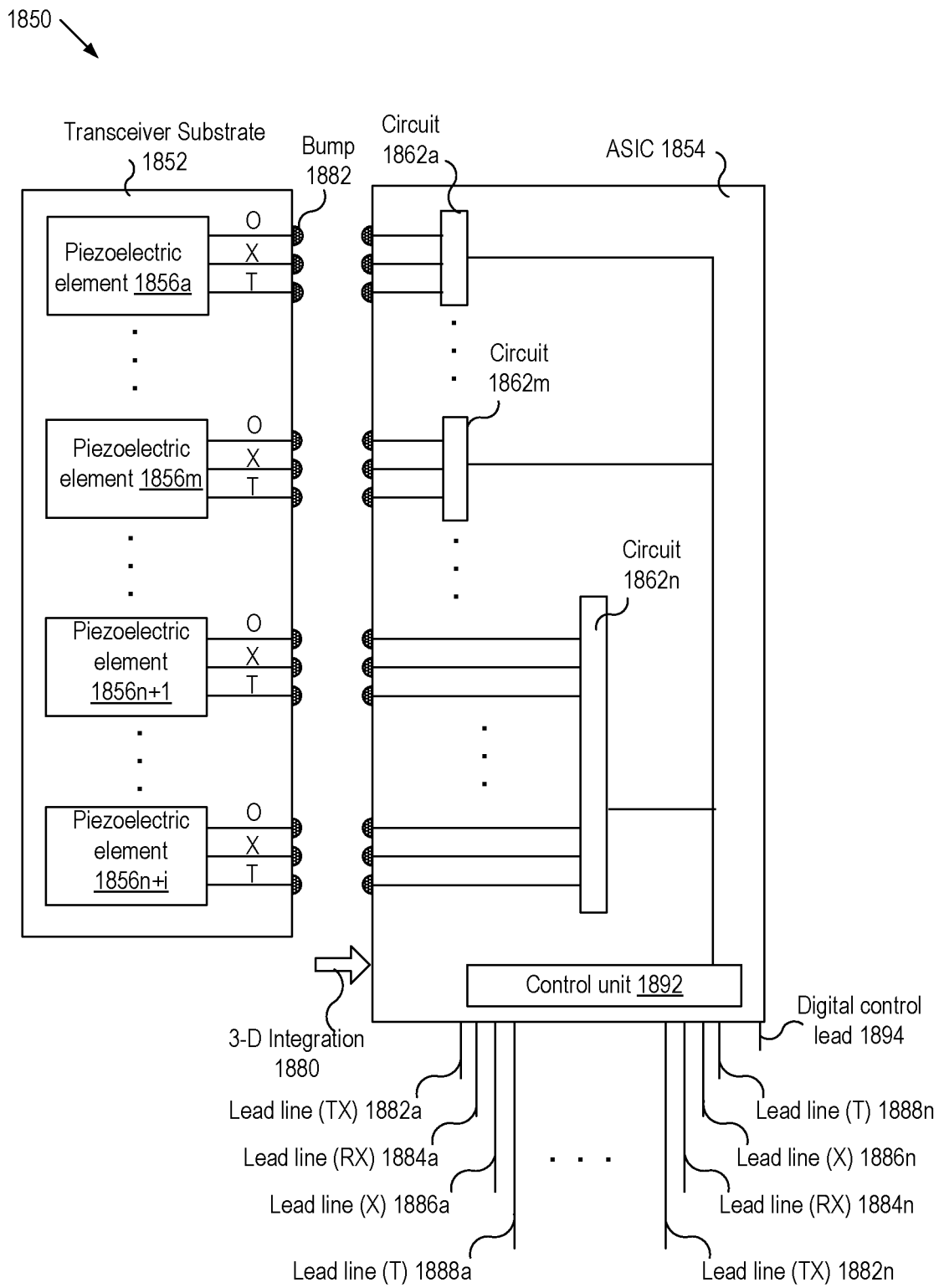
FIG. 18B shows a schematic diagram of an imaging assembly according to embodiments of the present disclosure.

FIG. 18B shows a schematic diagram of an imaging assembly 1850 according to embodiments of the present disclosure. In embodiments, the transceiver substrate 1852 and ASIC chip 1854 may be similar to the transceiver substrate 1802 and ASIC chip 1804, respectively. In the conventional systems, the electronics for driving piezoelectric transducers is typically located far away from the piezoelectric transducers and are connected to the piezoelectric transducers using a coax cable. In general, the coax cable increases parasitic loading, such as additional capacitance, on the electronics, and the additional capacitance causes loss in critical performance parameters, such as increase in noise and loss of signal power. In contrast, as depicted in FIG. 18B, the transmit driver or drivers (or equivalently circuits) 1862a-1862n may be connected directly to piezoelectric elements (or equivalently pixels) 1856a-1856n+i using a low impedance three dimensional (3D) interconnect mechanism (as indicated by an arrow 1880), such as Cu pillars or solder bumps 1882, or wafer bonding or similar approaches or a combination of such techniques. In embodiments, upon integrating the transceiver substrate 1852 to the ASIC chip 1854, the circuits 1862 may be located less than 100 μm vertically (or so) away from the piezoelectric elements 1856. In embodiments, any conventional device for impedance matching between driver circuits 1862 and piezoelectric elements 1856 may not be required, further simplifying design and increasing power efficiency of the imaging assembly 1800. Impedance of the circuits 1862 may be designed to match the requirement of the piezoelectric elements 1856.

In embodiments, in FIG. 18A, each of the piezoelectric elements 1806a-1806n may be electrically connected to a corresponding one of the circuits 1842a-1842n located in the ASIC chip 1804. In embodiments, this arrangement may allow the imager to generate three-dimensional images. Similarly, in FIG. 18B, each of the piezoelectric elements 1856a-1856m may have three leads represented by X, T, and O. The leads from each of the piezoelectric elements may be electrically connected to a corresponding one of the circuits 1862a-1862m located in the ASIC chip 1854 by the interconnect means 1882. In addition, in embodiments, a line of piezoelectric elements, such as 1856n+1-1856n+i may be electrically coupled to one common circuit 1862n. In embodiments, the transmit driver circuit 1862n may be implemented with one transmit driver. In alternative embodiment, the transmit driver circuit 1862n may be implemented with multilevel drivers to facilitate various imaging modes.

Figure 33:
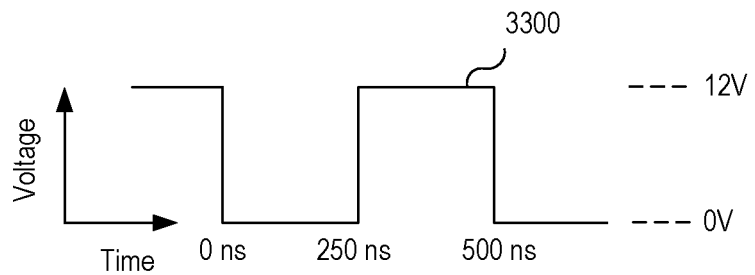
FIG. 33 shows a transmit drive signal waveform according to embodiments of the present disclosure.
Figure 34:
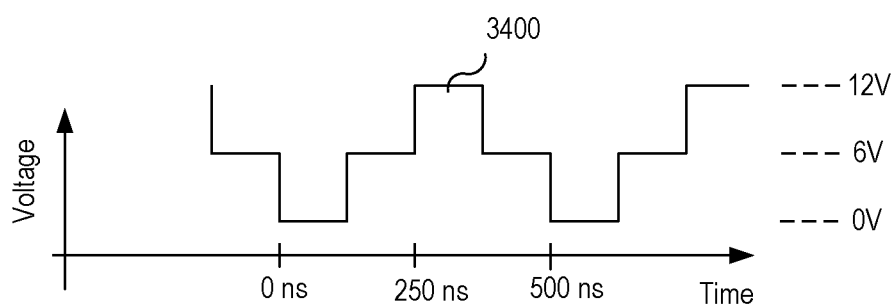
FIG. 34 shows a transmit drive signal waveform according to embodiments of the present disclosure.

It should be apparent to those of ordinary skill in the art that the ASIC chip 1854 may have any suitable number of circuits that are similar to the circuit 1862n. In embodiments, the control unit 1892 may have capability to configure the piezoelectric elements, either horizontally or vertically in a two dimensional pixel array, configure their length and put them into transmit or receive or poling mode or idle mode. In embodiments, the control unit 1892 may perform the poling process after the transceiver substrate 1852 is combined with the ASIC chip 1854 by the three dimensional integration technique 1882. In embodiments, the transmit driver circuit 1843 may be implemented with multilevel drive as shown in FIG. 34, where the transmit driver output may have more than 2 output levels. FIG. 34 shows an embodiment where the output level may be 0V or 6V or 12V. It is understood that that these voltages can be different, for example they can be −5V, 0V and +5V. The transmit driver can also be a 2 level driver with drive signal as shown in FIG. 33.

In embodiments, lead lines 1882a-1882n may be signal conductors that are used to apply pulses to the electrodes (O) of the piezoelectric elements 1856. Similarly, the lead lines 1884a-1884n, 1886a-1886n, and 1888a-1888n may be used to communicate signals with the piezoelectric elements 1856a-1856n+i. It is noted that other suitable number of lead lines may be used to communicate signals/data with the imaging assembly 1800.

In embodiments, each of the lead lines (X) 1886 and lead lines (T) 1888 may be connected to the ground or a DC bias terminal. In embodiments, the digital control lead 1894 may be a digital control bus and include one or more leads that are needed to control and address the various functions in the imaging assembly 1850. These leads, for example, may allow programmability of the ASIC chip 1854 using communication protocols, such as Serial Peripheral Interface (SPI) or other protocols.

In embodiments, the piezoelectric elements 1806 (or 1856) and the control electronics/circuits 1842 (or 1862) may be developed on the same semiconductor wafer. In alternative embodiments, the transceiver substrate 1802 (or 1852) and ASIC chip 1804 (or 1854) may be manufactured separately and combined to each other by a 3D interconnect technology, such as metal interconnect technology using bumps 1882. In embodiments, the interconnect technology may eliminate the low yield multiplication effect, to thereby lower the manufacturing cost and independently maximize the yield of components.

In embodiments, lead lines 1862a-1862n may be signal conductors that are used to apply pulses to the electrodes (O) of the piezoelectric elements 1806. Similarly, the lead lines 1864a-1864n, 1866a-1866n, and 1868a-1868n may be used to communicate signals with the piezoelectric elements 1806a-1806n. It is noted that other suitable number of lead lines may be used to communicate signals/data with the imaging assembly 1800.

As discussed above, the LNAs 1811 may operate in a charge sensing mode and each have a programmable gain that may be configured in real time to provide gain compensation. In embodiments, as discussed in conjunction with FIG. 3B, one or more temperature sensors may be installed in the imager 120. In embodiments, the ASIC may receive temperature data from the temperature sensor(s) and, using the temperature data, adjust the imaging frame rate or a signal-to-noise ratio of the LNAs 1811.

Figures 1, 19A:
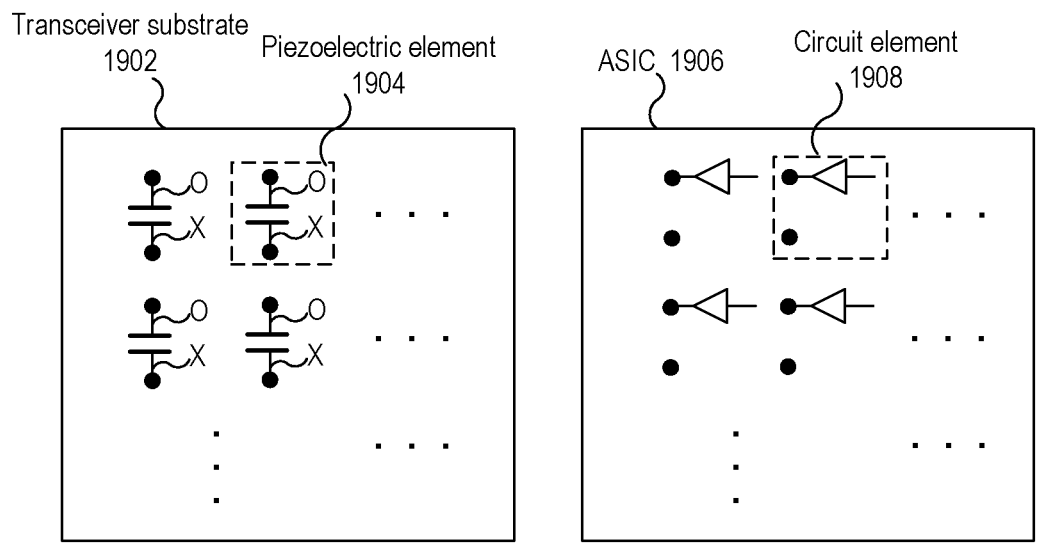
Figures 2, 19A:
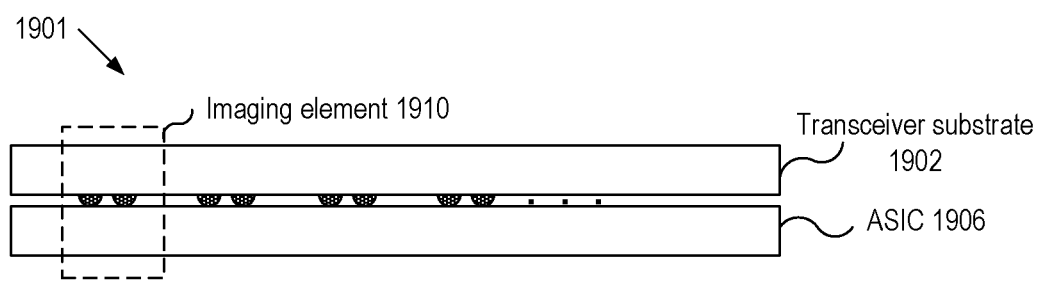

FIG. 19A-1 shows a top view of a transceiver substrate 1902 and an ASIC chip 1906 and FIG. 19A-2 shows a side view of imaging assembly 1901 according to embodiments of the present disclosure. As depicted, the imaging assembly 1901 may include the transceiver substrate 1902 that is interconnected to the ASIC chip 1906 by suitable interconnection mechanism, such as bumps. Hereinafter, the bumps are shown as the interconnection mechanism, even though other suitable interconnection mechanisms may be used in place of the bumps.

In embodiments, each piezoelectric element 1904 may be a two terminal piezoelectric element, where the piezoelectric element is symbolically represented by two electrodes O and X. In embodiments, the circuit element 1908 may include electrical components for driving the corresponding piezoelectric element 1904, where the circuit element 1908 is symbolically represented by a transmit driver. In embodiments, an imaging element 1910 may include a piezoelectric element 1904 and a circuit element 1908, and the piezoelectric element 1904 may be electrically connected to the circuit element 1908 by two bumps.

Figures 1, 19B:
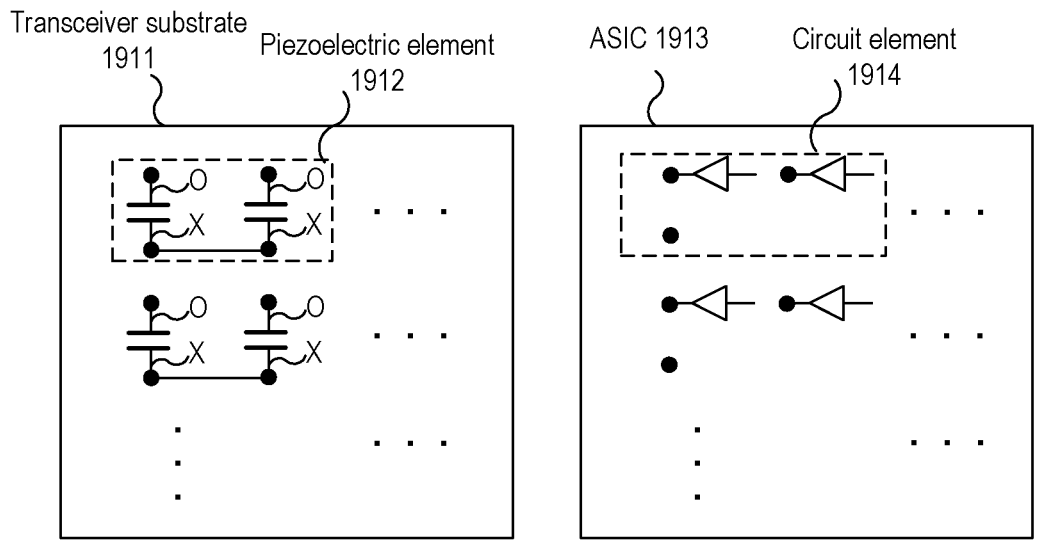
Figures 2, 19B:
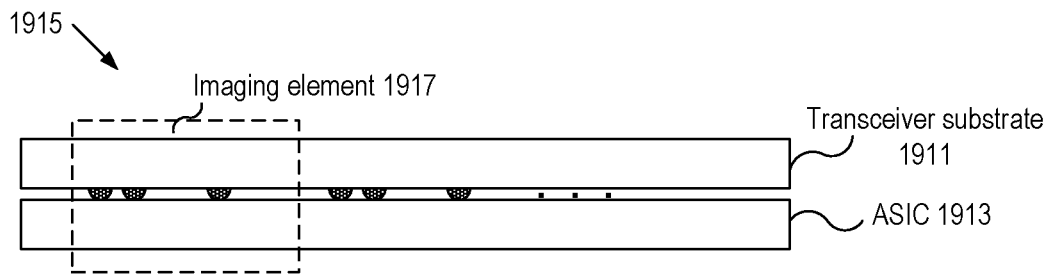

FIG. 19B-1 shows a top view of a transceiver substrate 1911 and an ASIC chip 1913 and FIG. 19B-2 shows a side view of imaging assembly 1915 according to embodiments of the present disclosure. As depicted, the imaging assembly 1915 may be similar to the imaging assembly 1901, with the difference that two sub piezoelectric elements are electrically coupled to two sub circuit elements by three bumps. More specifically, the piezoelectric element 1912 includes two sub piezoelectric elements, each sub piezoelectric element may be a two terminal piezoelectric element, and the X electrodes of the two sub piezoelectric elements may be electrically coupled to each other. In embodiments, each O electrode of the sub piezoelectric element may be electrically coupled to a transmit driver of the corresponding sub circuit element 1914 and the X electrodes of the two sub piezoelectric elements may be electrically coupled to a common electrical terminal of the circuit element 1914. As such, in each imaging element 1917, the piezoelectric element 1912 may be interconnected to the circuit element 1914 by three bumps.

Figure 19C:
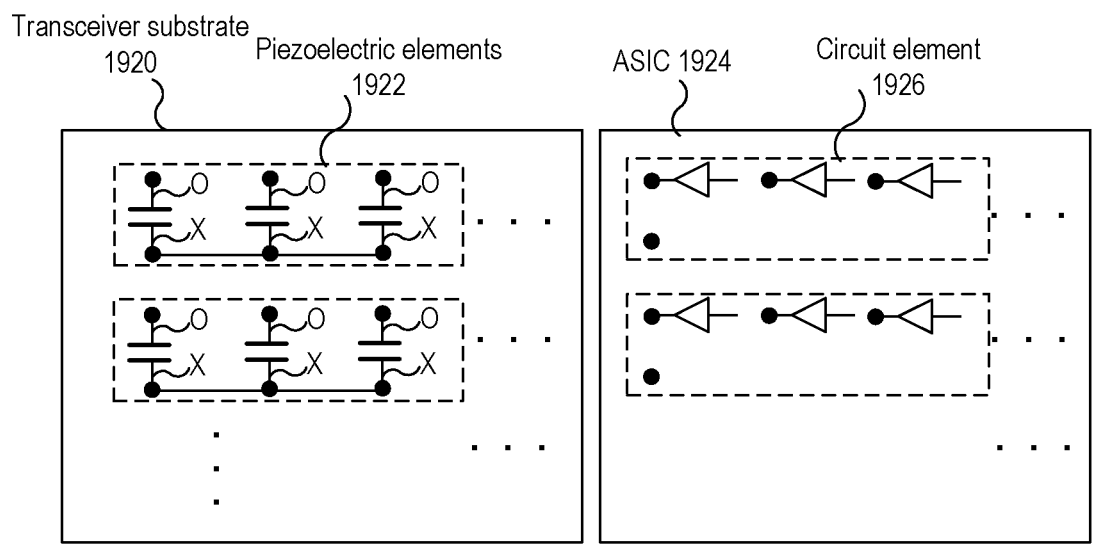
FIG. 19C shows a top view of a transceiver substrate and an ASIC chip according to embodiments of the present disclosure.

FIG. 19C shows a top view of a transceiver substrate 1920 and an ASIC chip 1924 according to embodiments of the present disclosure. As depicted, the transceiver substrate 1920 may be similar to the transceiver substrate 1902, with the difference that three sub piezoelectric elements are electrically coupled to three sub circuit elements by four bumps. More specifically, the piezoelectric element 1922 includes three sub piezoelectric elements, each sub piezoelectric element may be a two terminal piezoelectric element, and the X electrodes of the three sub piezoelectric elements may be electrically coupled to each other. In embodiments, each O electrode of the sub piezoelectric element may be electrically coupled to a transmit driver of the corresponding sub circuit element and the X electrodes of the three sub piezoelectric elements may be electrically coupled to a common electrical terminal of the circuit element 1926. As such, the piezoelectric element 1922 may be interconnected to the circuit element 1926 by four bumps.

Figure 19D:
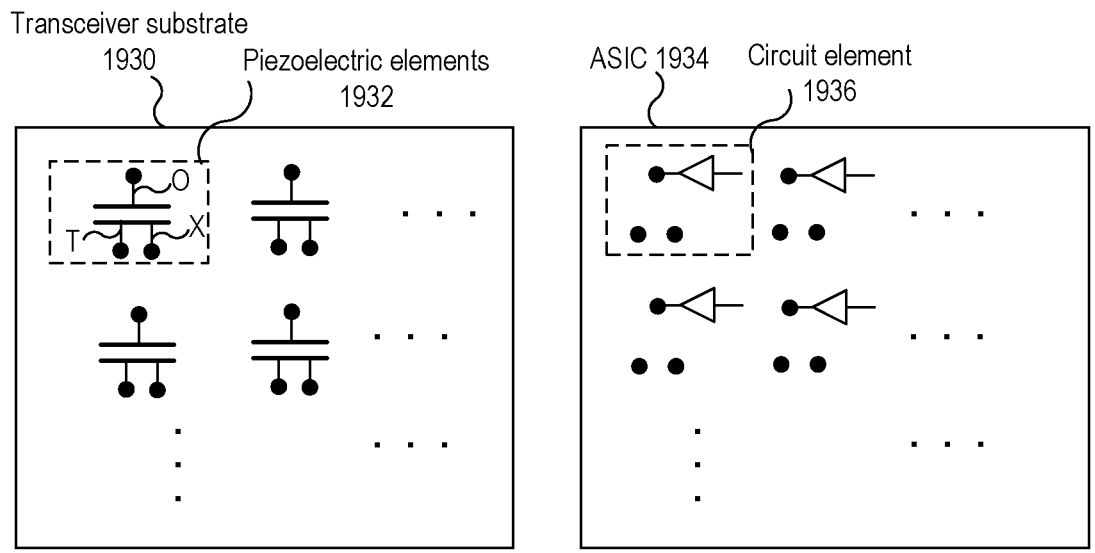
FIG. 19D shows a top view of a transceiver substrate and an ASIC chip according to embodiments of the present disclosure.

It is noted that the piezoelectric element may have more than two terminals. FIG. 19D shows a top view of a transceiver substrate 1930 and an ASIC chip 1934 according to embodiments of the present disclosure. As depicted, the transceiver substrate 1930 may be similar to the transceiver substrate 1902, with the difference that each piezoelectric element 1932 may be electrically coupled to a circuit element 1936 by three bumps. In embodiments, the O electrode may be coupled to a transmit driver of the circuit element 1936 by a bump, and the X and T electrodes may be coupled to the circuit element 1936 by two bumps.

Figure 19E:
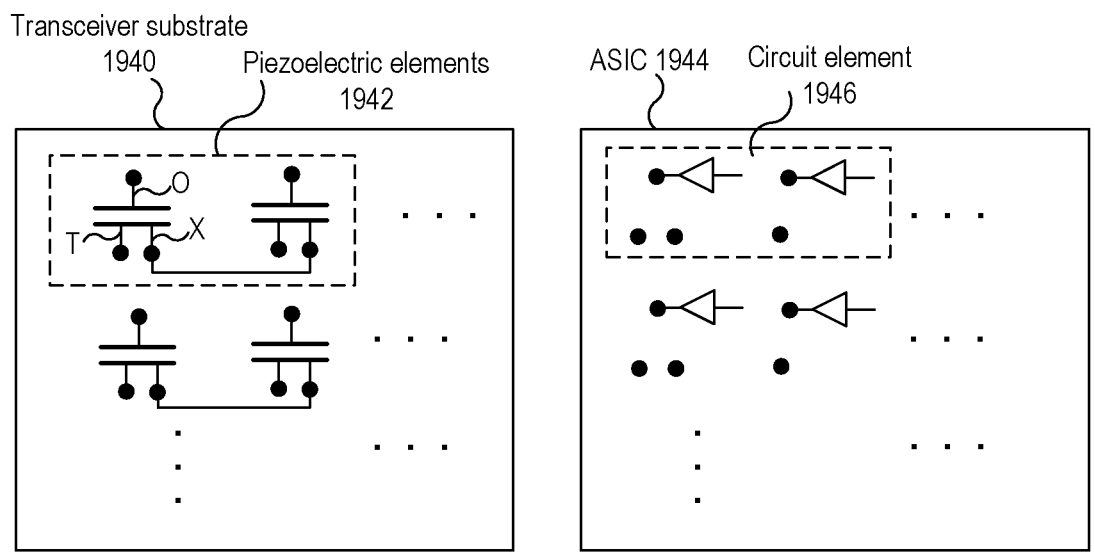
FIG. 19E shows a top view of a transceiver substrate and an ASIC chip according to embodiments of the present disclosure.

FIG. 19E shows a top view of a transceiver substrate 1940 and an ASIC chip 1944 according to embodiments of the present disclosure. As depicted, the piezoelectric element 1942 may include two sub piezoelectric elements, each sub piezoelectric element may be a three terminal piezoelectric element, and the X electrodes of the two sub piezoelectric elements may be electrically coupled to each other. In embodiments, each O electrode of the sub piezoelectric element may be electrically coupled to a transmit driver of the corresponding sub circuit element by a bump and the X electrodes of the two sub piezoelectric elements may be electrically coupled to the circuit element 1946 by a bump and each T electrode of the sub piezoelectric element may be electrically coupled to the circuit element 1946 by a bump. As such, the piezoelectric element 1942 may be interconnected to the circuit element 1946 by five bumps.

Figure 19F:
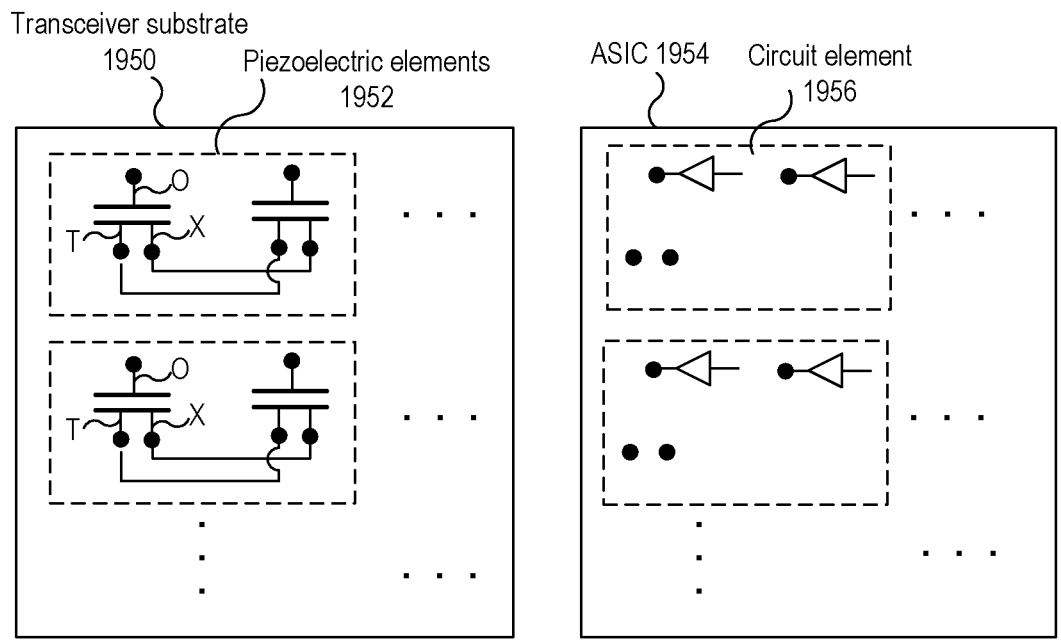
FIG. 19F shows a top view of a transceiver substrate and an ASIC chip according to embodiments of the present disclosure.

FIG. 19F shows a top view of a transceiver substrate 1950 and an ASIC chip 1954 according to embodiments of the present disclosure. As depicted, the piezoelectric element 1952 may include two sub piezoelectric elements, each sub piezoelectric element may be a three terminal piezoelectric element, the X electrodes of the two sub piezoelectric elements may be electrically coupled to each other, and T electrodes of the two sub piezoelectric elements may be electrically coupled to each other. In embodiments, each O electrode of the sub piezoelectric element may be electrically coupled to a transmit driver of the corresponding sub circuit element by a bump and the X electrodes of the two sub piezoelectric elements may be electrically coupled to the circuit element 1956 by a bump. Also, the T electrodes of the two sub piezoelectric elements may be electrically coupled to the circuit element 1956 by a bump. As such, the piezoelectric element 1952 may be interconnected to the circuit element 1956 by four bumps.

Figure 19G:
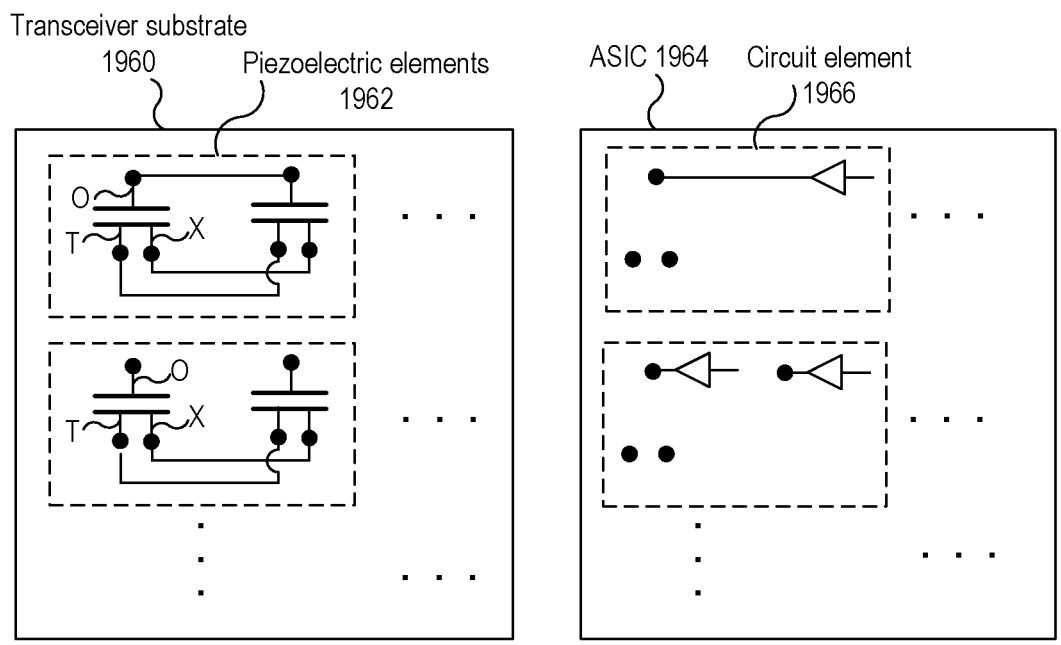
FIG. 19G shows a top view of a transceiver substrate and an ASIC chip according to embodiments of the present disclosure.

FIG. 19G shows a top view of a transceiver substrate 1960 and an ASIC chip 1964 according to embodiments of the present disclosure. As depicted, the piezoelectric element 1962 may include two sub piezoelectric elements, each sub piezoelectric element may be a three terminal piezoelectric element, the O electrodes of the two sub piezoelectric elements may be electrically coupled to each other, the X electrodes of the two sub piezoelectric elements may be electrically coupled to each other, and the T electrodes of the two sub piezoelectric elements may be electrically coupled to each other. As such, the piezoelectric element 1962 may be interconnected to the circuit element 1966 by three bumps.

Figure 20:
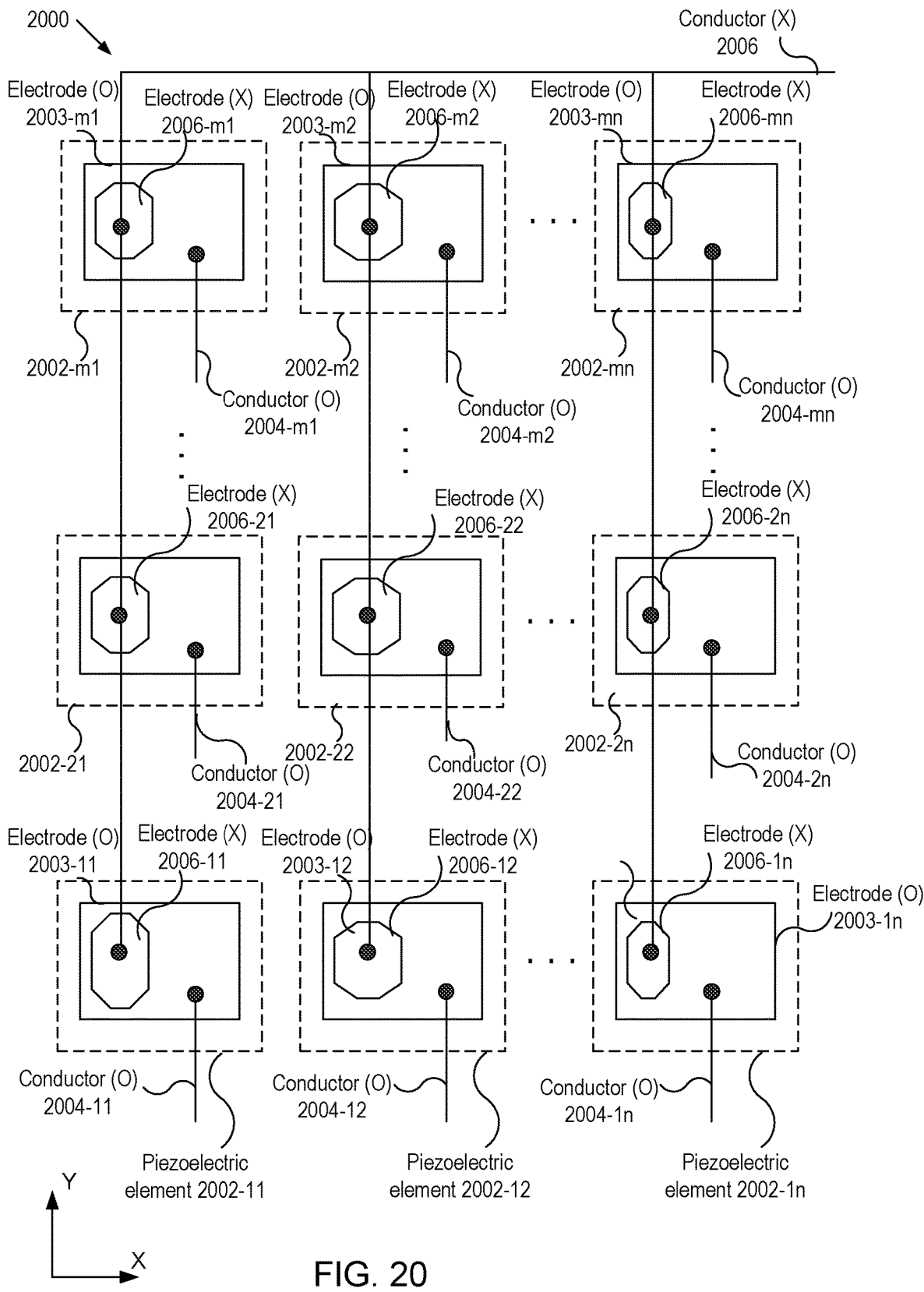
FIG. 20 illustrates a schematic diagram of an array of piezoelectric elements capable of performing two and three dimensional imaging according to embodiments of the present disclosure.

FIG. 20 shows a schematic diagram of an m×n array 2000 of piezoelectric elements 2002-11-2002-*mn* according to embodiments of the present disclosure. As depicted, each piezoelectric element may be a two terminal piezoelectric element (such as piezoelectric element 900 in FIG. 9) and have an electrode (O) (e.g. 2003-11) electrically coupled to a conductor (O) (e.g. 2004-11) and an electrode (X) electrically connected to ground or a DC bias voltage via a common conductor (X) 2006. In embodiments, each signal conductor (O) may be managed independently by a circuit element (such as 1908). In embodiments, each conductor (O) (e.g. 2004-*mn*) may be electrically coupled to a transmit driver of a circuit element while all of the X electrodes (2006-11-2006-*mn*) of the piezoelectric element array may be connected to a common conductor (X) 2006. In embodiments, the array 2000 may be disposed on a transceiver substrate and electrically coupled to an ASIC chip by interconnection mechanism, such as m×n+1 bumps, as discussed in conjunction with FIGS. 19A-19G. More specifically, the m×n conductors (O) 2004-11-2004-*mn* may be coupled to m×n transmit drivers of ASIC chip by m×n bumps and the common conductor (X) 2006 may be coupled to the ASIC chip by one bump. In embodiments, such an exemplary arrangement as described here is used to perform 3D imaging, where each piezoelectric element, including at least one sub piezoelectric element, can provide unique information in the array. In embodiments, each piezoelectric element may have one or more membranes and vibrate in multiple modes and frequencies of the membranes. In embodiments, each piezoelectric element 2002 may be driven by pulses that have voltage profiles 3300 and 3400 in FIGS. 33 and 34.

In embodiments, the O electrodes in each column (e.g. 2003-11-2003-$m1$) may be electrically coupled to a common conductor. For instance, the circuit elements in the ASIC chip may be electronically controlled so that the O electrodes in each column may be electrically coupled to each other. In such a configuration, the O electrodes in each column may receive the same electrical pulse through a common transmit driver or per a multiplicity of drivers with identical electrical drive signals during the transmit mode. Similarly, the O electrodes in each column may simultaneously transmit the electrical charge to a common amplifier during the receive mode. Stated differently, the piezoelectric element in each column may be operated as a line unit (or equivalently line element).

Figure 21:
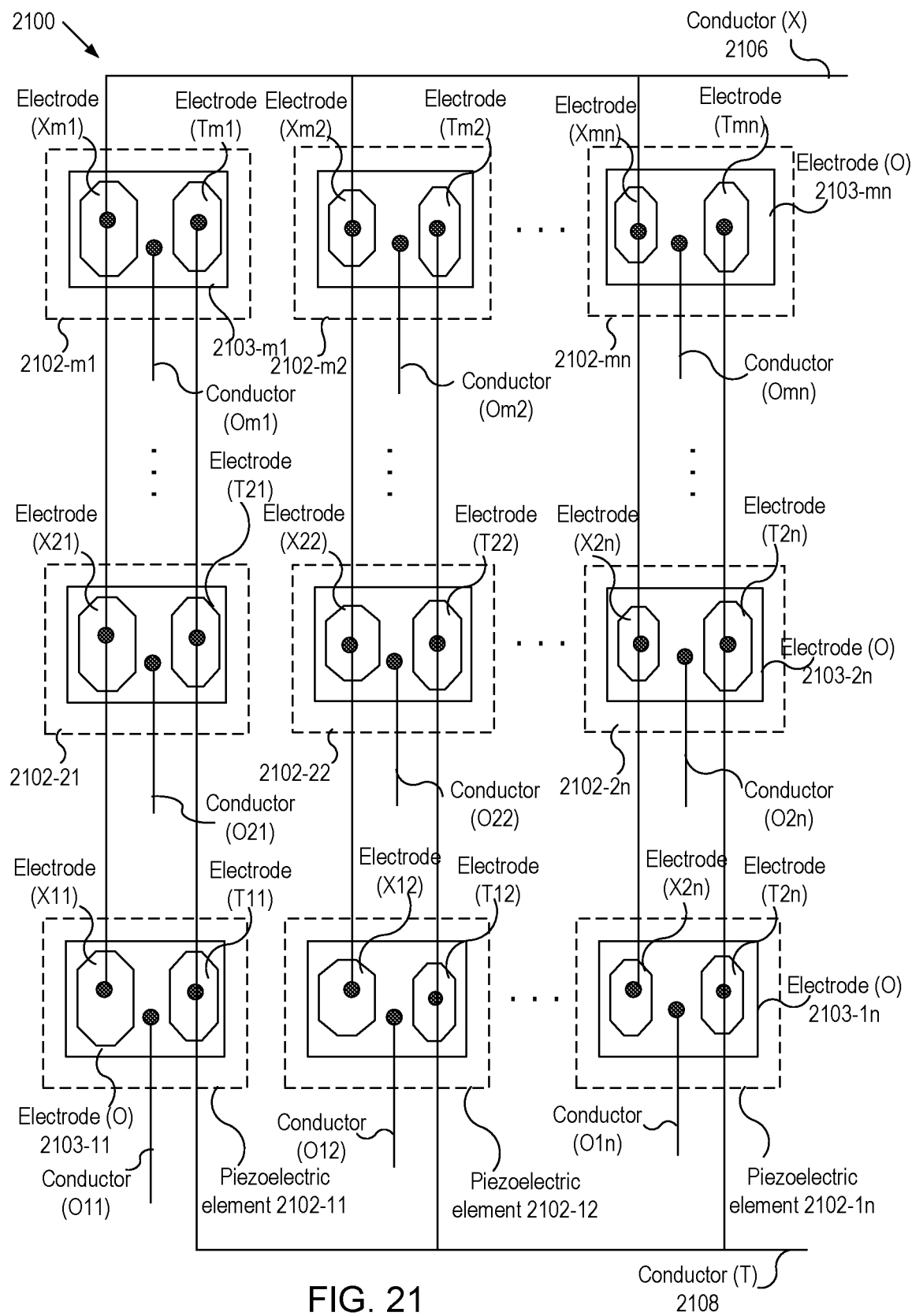
FIG. 21 illustrates a schematic diagram of an array of piezoelectric elements according to embodiments of the present disclosure.

FIG. 21 illustrates a schematic diagram of an n×n array 2100 of piezoelectric elements 2102-11-2012-$mn$ according to embodiments of the present disclosure. As depicted, each piezoelectric element may be a three terminal piezoelectric element and include the electrodes O, X, and T. In embodiments, the X electrodes (e.g. X11, X21, . . . , Xm1) may be connected column wise in a serial manner and all of the X electrodes (X11-Xmn) may be electrically coupled to a common conductor (X) 2106. The T electrodes (e.g. T11, T21, . . . , Tm1) may be connected column wise in a serial manner and all of the T electrodes (T11-Tmn) may be electrically coupled to a common conductor (T) 2108. A column of elements such as 2102-11, 2102-21 through 2102-$m1$ when connected together as described in embodiments make up a line element or a column. In embodiments, each of the O electrodes 2103-11-2103-$mn$ may be electrically coupled to a transmit driver of a corresponding circuit element in an ASIC chip via one of the conductors O11-Omn. In embodiments, the array 2100 may be disposed on a transceiver substrate and electrically coupled to an ASIC chip by interconnection mechanism, such as m×n+2 bumps.

In embodiments, the O electrodes in each column (e.g. 2103-11-2103-$m1$) may be electrically coupled to a common conductor. In such a configuration, the O electrodes in each column may receive the same electrical pulse through a common transmit driver during the transmit mode. Similarly, the O electrodes in each column may simultaneously transmit the electrical charge to a common amplifier during the receive mode. Stated differently, the piezoelectric element in each column is operated as a line unit. In embodiments each of the O electrodes in a column may be connected to a dedicated transmit driver, where the input signal of the transmit drivers for all elements in a column are identical, thus creating a substantially identical transmit drive output to appear on all piezoelectric elements during a transmit operation. Such a line element is electronically controlled on a per element basis, since each element has it own transmit driver. This has advantages in driving large capacitive line elements, where each element has smaller capacitance and delays in timing can be minimized for elements on a column. In embodiments, in a receive mode, charge from all elements in a column can be sensed by connecting it to a LNA, as is done by 2D imaging. For 3D imaging, charge for each element is sensed by connecting the O electrodes of each element to a LNA during a receive mode operation.

Figure 22:
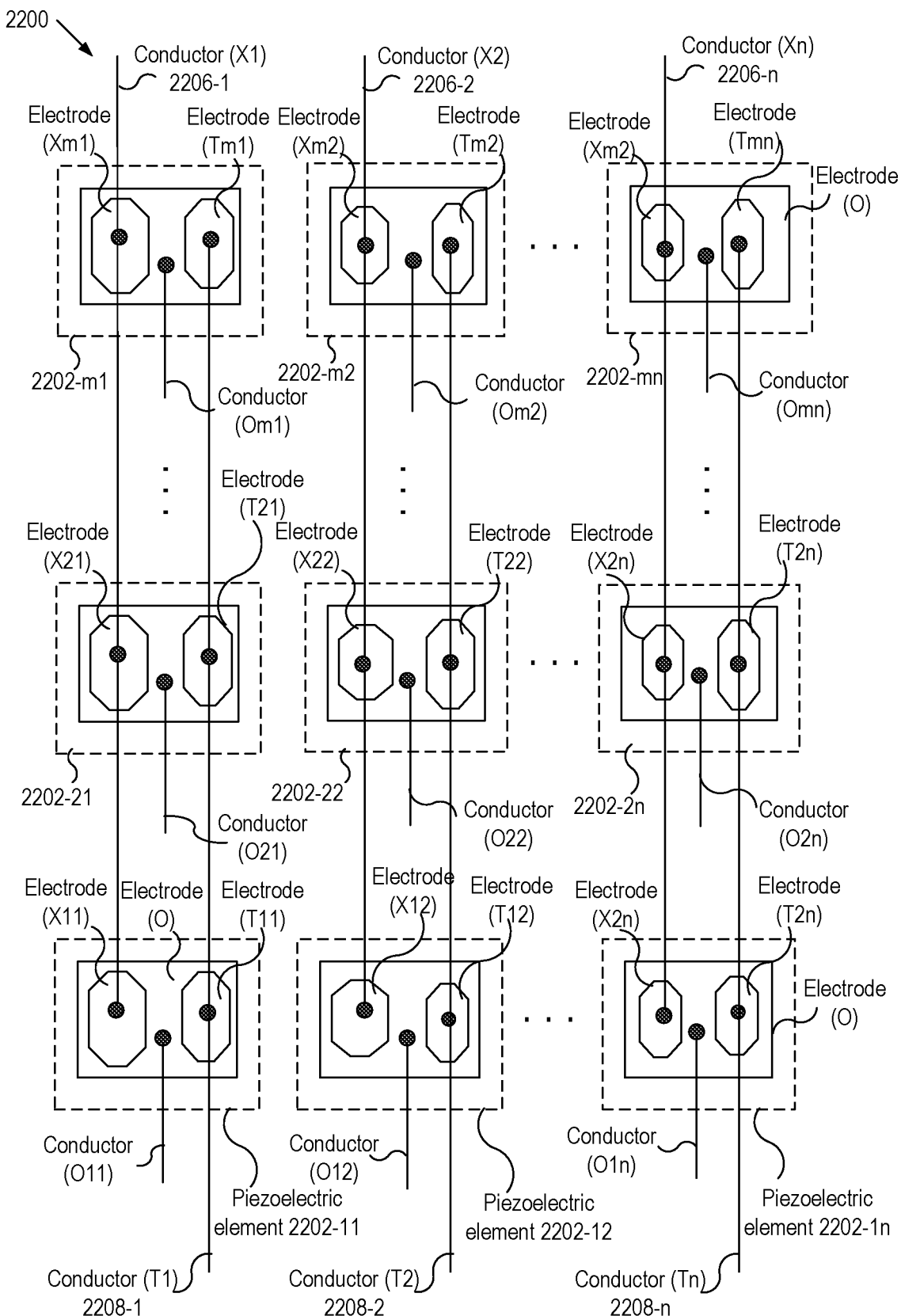
FIG. 22 illustrates a schematic diagram of an array of piezoelectric elements according to embodiments of the present disclosure.

FIG. 22 illustrates a schematic diagram of an m×n array 2200 of piezoelectric elements 2202-11-2202-$mn$ according to embodiments of the present disclosure. As depicted, the array 2200 may be similar to the array 2100, with the differences that the X electrodes (e.g. X12-Xm2) in a column may be connected to a common conductor (e.g. 2206-1) and the T electrodes (e.g. T12-Tm2) in a column may be connected to a common conductor (e.g. 2208-1). As such, the X electrodes (or T electrodes) in the same column may have the same voltage potential during operation. In embodiments, each of the O electrodes may be electrically coupled to a transmit driver of a corresponding circuit element in an ASIC chip via one of the conductors O11-Omn. In embodiments, the array 2200 may be disposed on a transceiver substrate and electrically coupled to an ASIC chip by interconnection mechanism, such as m×n+2n bumps.

Compared to array 2100, the array 2200 may use more bumps for connecting the T and X electrodes to the ASIC chip. In general, an increase in the number of connections for T and X between the ASIC chip and the piezoelectric array may reduce impedance in the X and T conductors when connected in parallel to the ground or DC bias sources and reduce the crosstalk. Crosstalk refers to the coupling of signals from an imaging element to another one, and may create interference and reduce the image quality. Spurious electrical coupling may be created when any voltage drop due to current flowing in X and T lines appear across a piezoelectric element that ideally should not be exposed to that voltage. In embodiments, when the piezoelectric element is not transmitting or receiving under electronic control, the X, T, and O electrodes may be locally shorted. Alternatively, the idle electrodes have the O electrodes grounded, leaving the X electrodes connected to other X electrodes in the array and the T electrodes connected to other T electrodes in the array.

Figure 23:
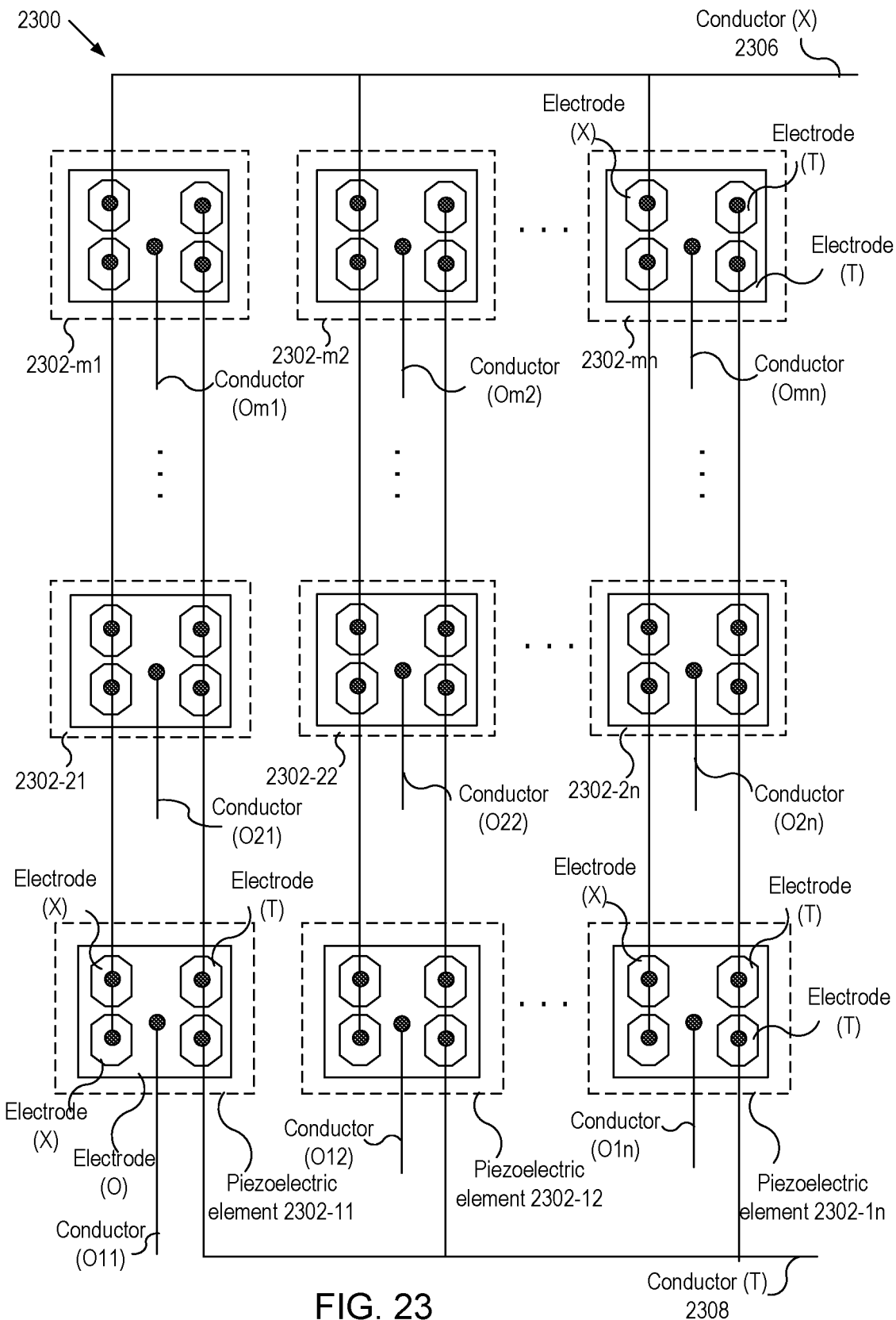
FIG. 23 illustrates a schematic diagram of an array of piezoelectric elements according to embodiments of the present disclosure.

FIG. 23 illustrates a schematic diagram of an m×n array 2300 of piezoelectric elements 2302-11-2302-$mn$ according to embodiments of the present disclosure. As depicted, the array 2300 may be similar to the array 2100, with the difference that each piezoelectric element may be a five terminal piezoelectric element, i.e., each piezoelectric element may include one bottom electrode (O) and four top electrodes (two X electrodes and two T electrodes). In embodiments, two X electrodes of each piezoelectric element may be connected column wise in a serial manner and all of the 2m×n X electrodes may be electrically coupled to a common conductor (X) 2306. Similarly, the two T electrodes of each piezoelectric element may be connected column wise in a serial manner and all of the 2m×n T electrodes may be electrically coupled to a common conductor (T) 2308. In embodiments, each of the O electrodes may be electrically coupled to a transmit driver of a corresponding circuit element in an ASIC chip via one of the conductors O11-Omn. In embodiments, the array 2300 may be disposed on a transceiver substrate and electrically coupled to an ASIC chip by interconnection mechanism, such as m×n+2 bumps.

Figure 24:
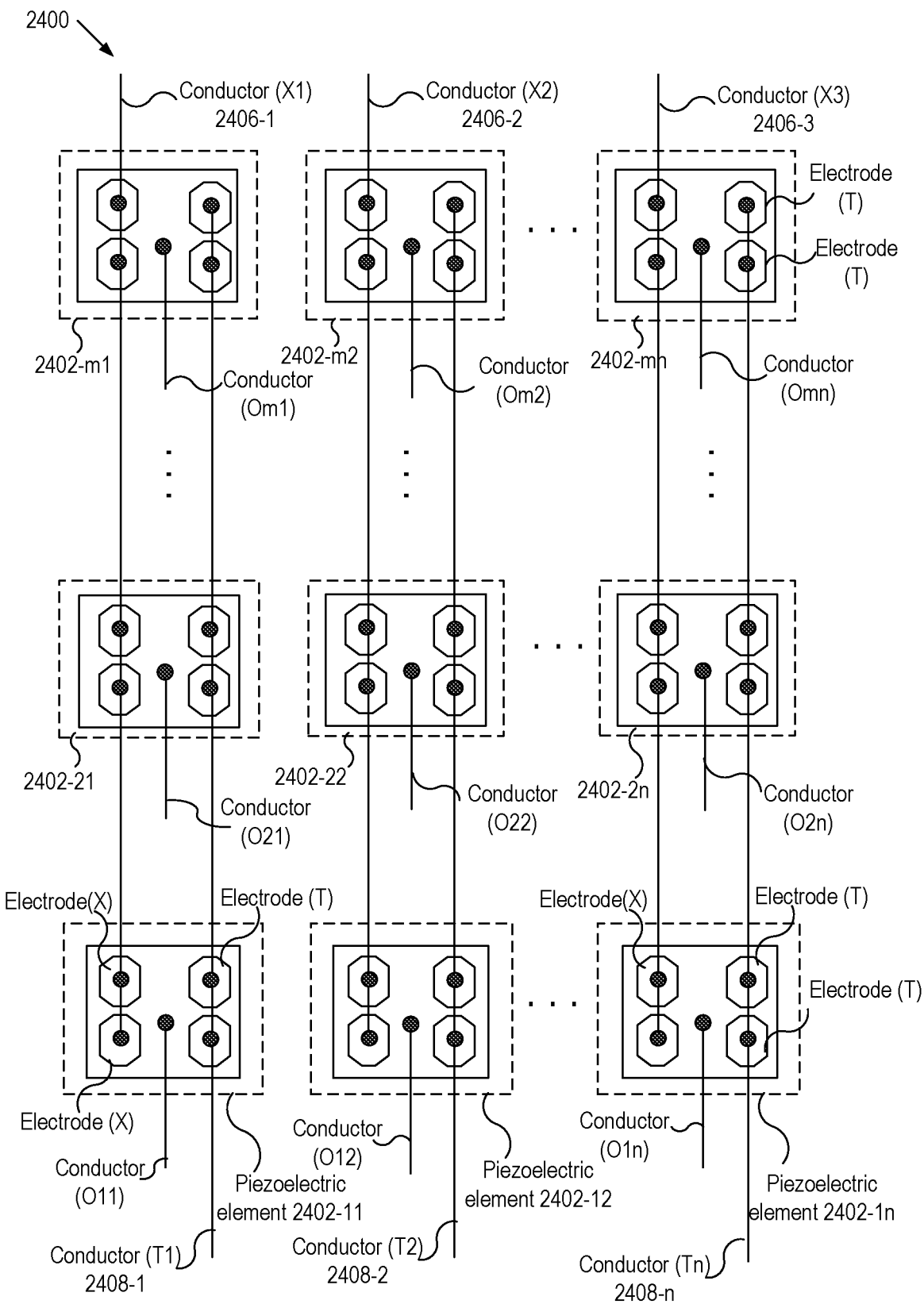
FIG. 24 illustrates a schematic diagram of an array of piezoelectric elements according to embodiments of the present disclosure.

FIG. 24 illustrates a schematic of an m×n array 2400 of piezoelectric elements 2402-11-2402-$mn$ according to embodiments of the present disclosure. As depicted, the array 2400 may be similar to the array 2200, with the differences that each piezoelectric element may be a five terminal piezoelectric element: one bottom electrode (O)

and four top electrodes (two X electrodes and two T electrodes). In embodiments, the two X electrodes of each piezoelectric element may be electrically connected in a column wise direction to a conductor (e.g. 2406-1), and the two T electrodes of each piezoelectric element may be electrically connected in a column wise direction to a common conductor (e.g. 2408-1). In embodiments, each of the O electrodes may be electrically coupled to a transmit driver of a corresponding circuit element in an ASIC chip via one of the conductors O11-Omn. In embodiments, the array 2400 may be disposed on a transceiver substrate and electrically coupled to an ASIC chip by interconnection mechanism, such as m×n+2n bumps.

Figure 25:
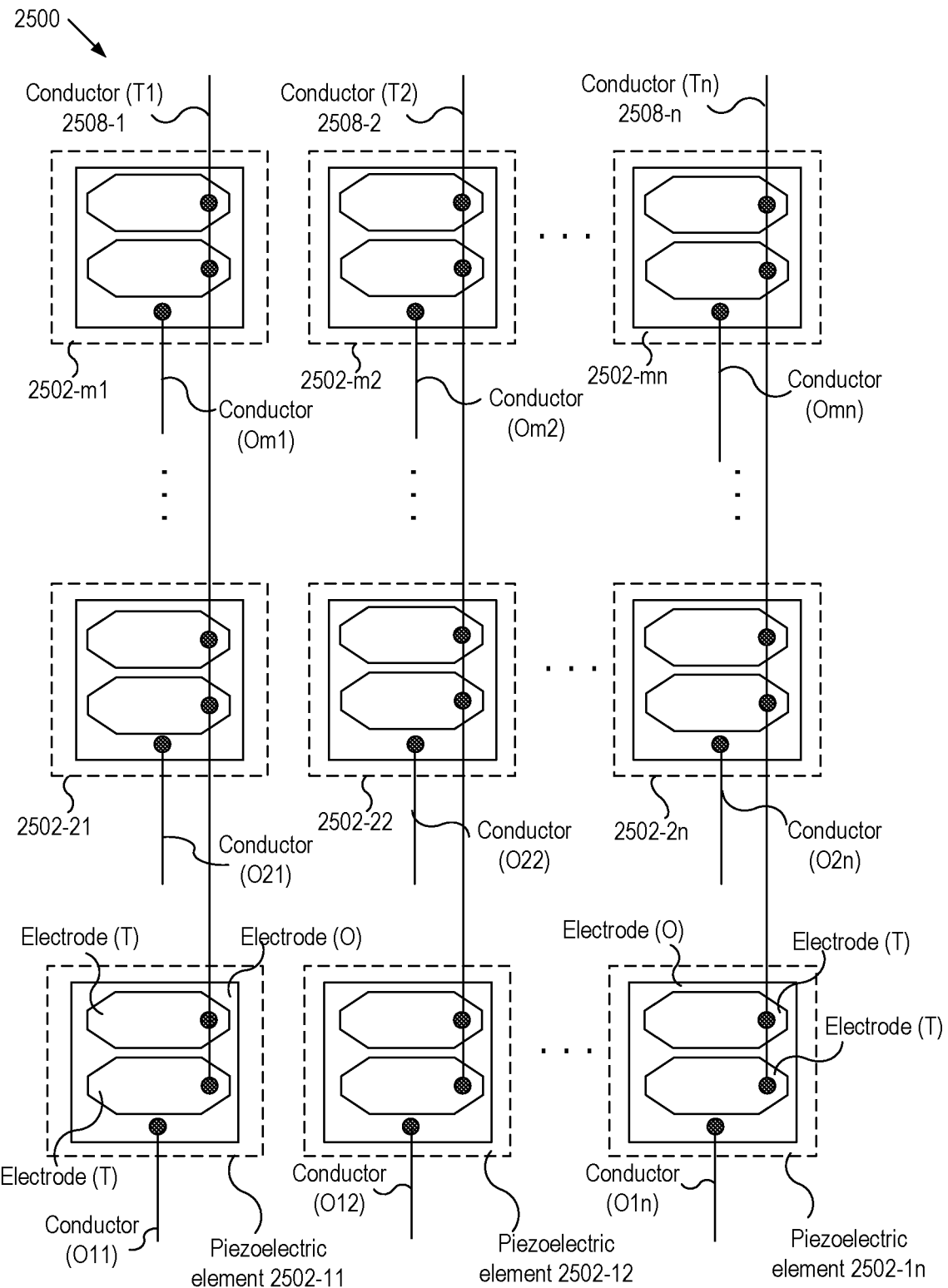
FIG. 25 illustrates a schematic diagram of an array of piezoelectric elements according to embodiments of the present disclosure.

FIG. 25 illustrates a schematic diagram of an m×n array 2500 of piezoelectric elements 2502-11-2502-*mn* according to embodiments of the present disclosure. As depicted, the array 2500 may be similar to the array 2100 in that each piezoelectric element may have one bottom electrode (O) and two top electrodes (T), but have the differences that all of the two top electrodes (T) of the piezoelectric elements along a column (e.g. 2502-11-2502-*m*1) may be electrically connected to a common conductor (e.g. 2508-1). In embodiments, each of the O electrodes may be electrically coupled to a transmit driver of a corresponding circuit element in an ASIC chip via one of the conductors O11-Omn. In embodiments, the array 2500 may be disposed on a transceiver substrate and electrically coupled to an ASIC chip by interconnection mechanism, such as m×n+n bumps.

Figure 26:
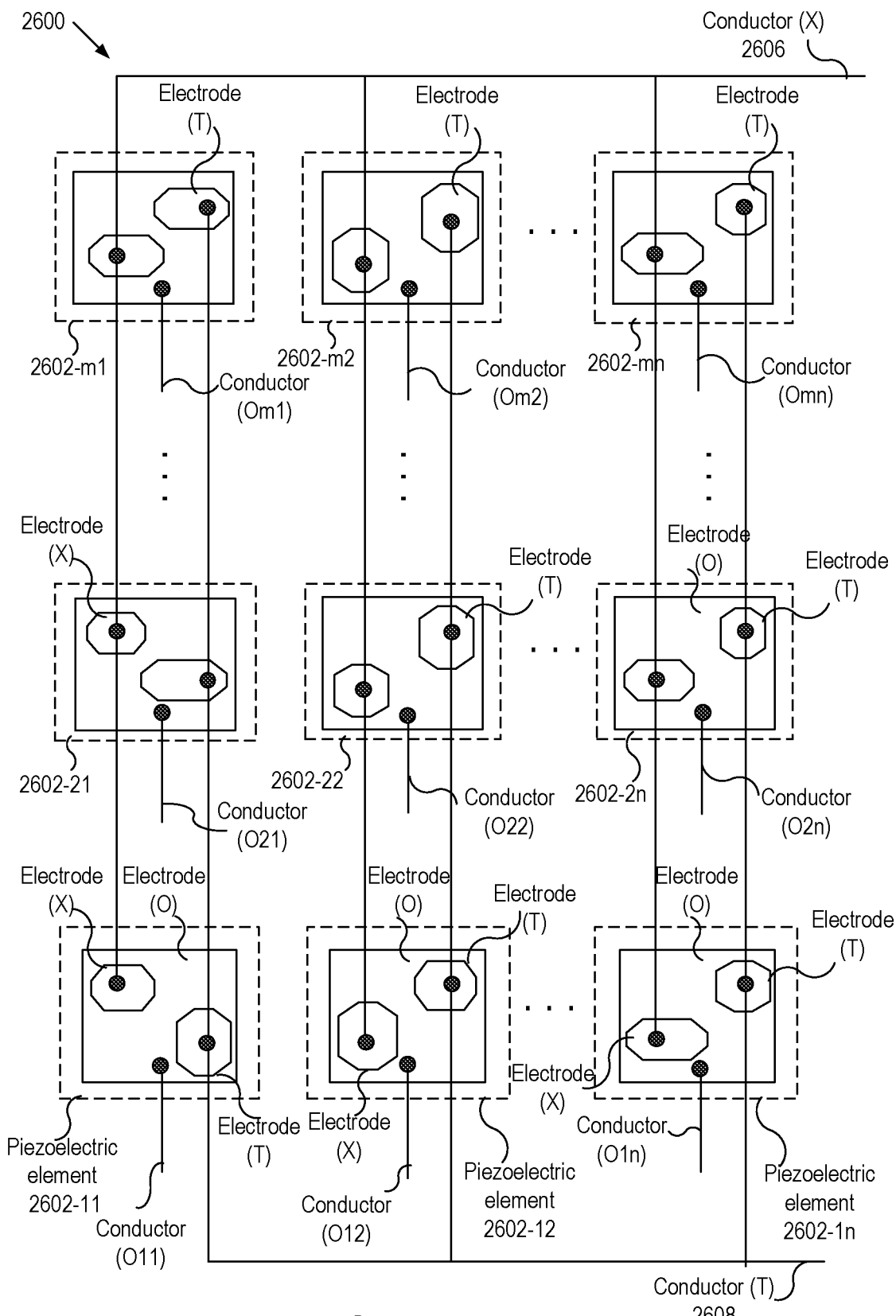
FIG. 26 illustrates a schematic diagram of an array of piezoelectric elements according to embodiments of the present disclosure.

FIG. 26 illustrates a schematic of an m×n array 2600 of piezoelectric elements 2602-11-2602-*mn* according to embodiments of the present disclosure. As depicted, the array 2600 may have similar electrical connections to the array 2100, i.e., all of the X electrodes in the piezoelectric elements may be electrically coupled to a common conductor 2606 and all of the T electrodes in the piezoelectric elements may be electrically coupled to a common conductor 2608. The array 2600 may be different from the array 2100 in that the top electrodes (X, T) of one piezoelectric element (e.g. 2602-11) may have the same or different geometrical shapes from the top electrodes (X, T) of another piezoelectric element (e.g. 2602-21).

For the piezoelectric arrays 2000-2500, the piezoelectric elements in each piezoelectric array may be the same or different from each other. For instance, the projection areas of the two top electrodes of one piezoelectric element 2202-11 may have same or different shapes from the projection areas of the two top electrodes of another piezoelectric element 2202-*n*1.

Figure 27:
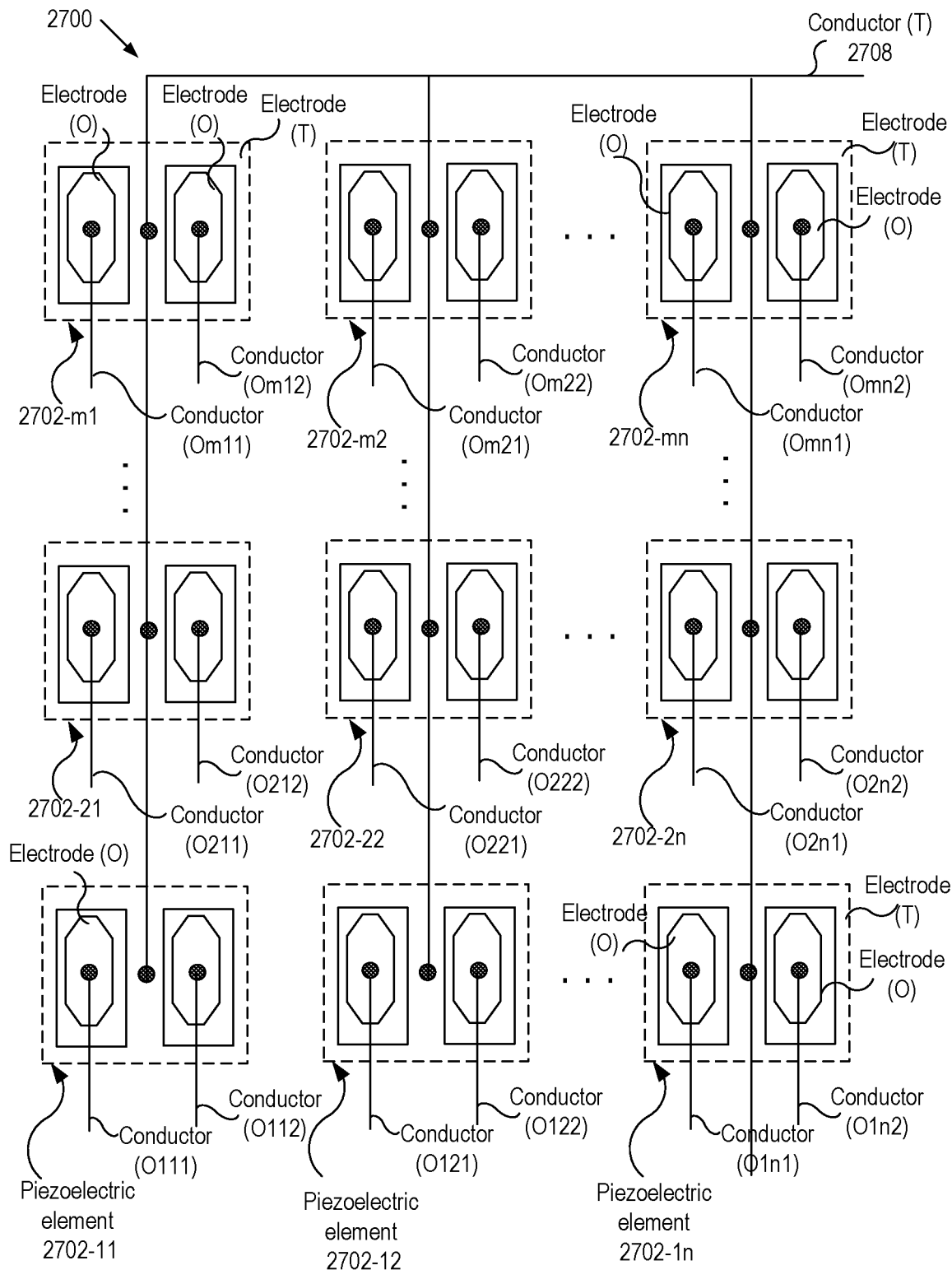
FIG. 27 illustrates a schematic diagram of an array of piezoelectric elements according to embodiments of the present disclosure.

FIG. 27 illustrates a schematic diagram of an m×n array 2700 of piezoelectric elements 2702-11-2702-*mn* according to embodiments of the present disclosure. As depicted, each piezoelectric element may include two signal electrodes (O) and one common electrode (X). In embodiments, each signal electrode (O) may be electrically coupled to a transmit driver of a corresponding circuit element of an ASIC chip. For instance, the piezoelectric element 2702-11 may include two signal conductors O111 and O112 that may be electrically coupled to two circuit elements in an ASIC chip, respectively, where each signal electrode may develop electrical charge during the receive mode. In embodiments, the array 2700 may be disposed on a transceiver substrate and electrically coupled to an ASIC chip by interconnection mechanism, such as 2m×n+1 bumps. In embodiments, all of the T electrodes in the array 2700 may be electrically coupled to the ground or a DC bias voltage via the common conductor (T) 2708.

In embodiments, the signal conductors (O) in the arrays in FIGS. 20-27 may be electrically coupled to a circuit element, where the circuit element may include a transistor switch that is similar to the switch 1816 in FIG. 18A, i.e., the switch may toggle between the transmit driver and an amplifier during the transmit and receive modes, respectively so that the O electrode may generate pressure wave during the transmit mode and develop electrical charge during the receive mode.

Figure 28:
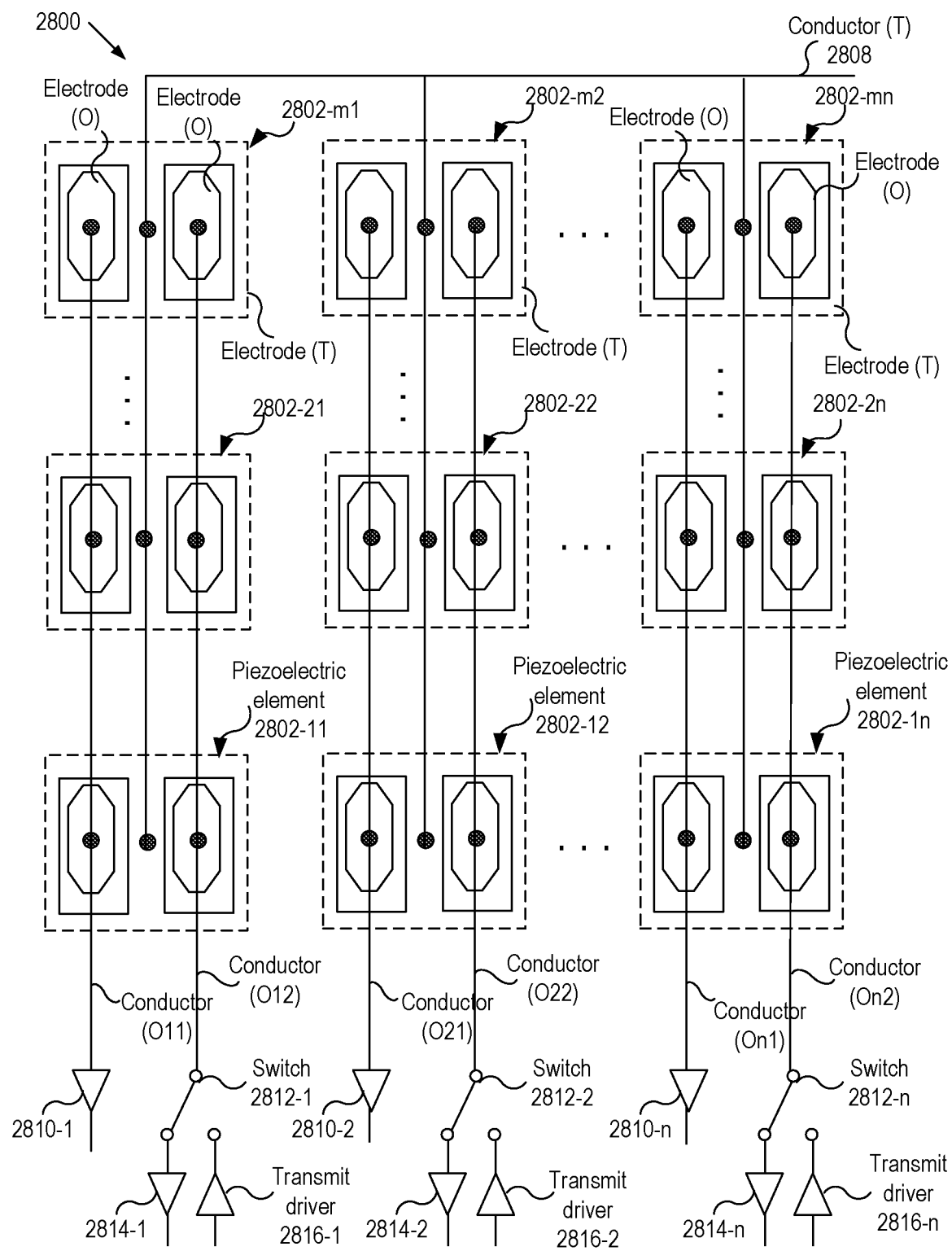
FIG. 28 illustrates a schematic diagram of an imaging system according to embodiments of the present disclosure.

FIG. 28 shows an exemplary embodiment of an imaging system 2800 according to embodiments of the present disclosure. As depicted, the imaging system 2800 may include an array of piezoelectric elements 2802-11-2802-*mn* and circuit elements for controlling/communicating with the array. In embodiments, each of the piezoelectric elements 2802-11-2802-*mn* may include three electrodes; first and second signal (O) electrodes and a T electrode. (For the purpose of illustration, the first and second O electrodes in each piezoelectric element refer to the left and right O electrodes of each piezoelectric element in FIG. 28.) In embodiments, all of T electrodes in the array 2800 may be electrically coupled to the ground or DC bias voltage via the conductor (T) 2808. In embodiments, the first O electrodes of the piezoelectric elements in a column may be electrically coupled to a common conductor (e.g. O11) and the second O electrodes of the piezoelectric elements in the same column may be electrically coupled to another common conductor (e.g. O12). In embodiments, during the receive mode, each of the first and second signal O electrodes may develop electrical charge that may be processed by a corresponding circuit.

In embodiments, the first set of conductors O11, O21, . . . , On1 may be electrically coupled to the amplifiers 2810-1-2810-*n*, respectively, where the electrical charge developed in a column of the first O electrodes may be transferred to a corresponding amplifier via one of the O conductors. In embodiments, the second set of conductors O12, O22, . . . , On2 may be electrically coupled to the switches 2812-1-2812-*n*, respectively. In embodiments, each switch (e.g. 2812-1) may be connected to a transit driver (e.g. 2816-1) during the transmit mode/process so that a signal pulse may be transmitted to a column of second O electrodes in the piezoelectric elements (e.g. 2801-11-2802-*m*1). In embodiments, each switch (e.g. 2812-1) may be connected to a signal amplifier (e.g. 2814-1) during the receive mode/process so that electrical charge developed in a column of second O electrodes in the piezoelectric elements (e.g. 2801-11-2802-*m*1) may be transmitted to the amplifier. In embodiments, the piezoelectric elements 2802-11-2802-*mn* may be disposed in a transceiver substrate while the switches 2812-1-2812-*n*, transmit drivers 2816-1-2816-*n*, and amplifies 2810-1-2810-*n* and 2814-1-2814-*n* may be disposed in an ASIC chip, where the transceiver substrate may be electrically coupled to the ASIC chip by 2n+1 bumps.

In embodiments, a column of the first electrodes may be electrically coupled to a common conductor (e.g. O11) and a column of the second electrodes may be electrically coupled to another common conductor (e.g. O12). As such, in embodiments, the imaging system 2800 may be operated as a line imager, i.e., each of the first set of conductors O11-On2 may operate as a transmit unit and/or a receive unit during operation. As discussed above, during the receive mode, the electrical charge developed in a column of the first O electrodes connected to a conductor (e.g. O11) may be transmitted to an amplifier (e.g. 2810-1), which may be a low noise amplifier. Then, the amplifier may amplify the electrical charge signal and convert the charge signal to an output voltage. Thus, each column of the first O electrodes may operate as a receiving line imager. In embodiments, during the receive mode, the electrical charge developed in a column of the second O electrodes connected to a conductor (e.g. O12) may be transmitted to a signal amplifier (e.g. 2814-1), which may be a low noise amplifier, via a switch (e.g. 2812-1). Then, the amplifier may amplify the electrical charge signal and convert the charge signal to an output voltage. Thus, each column of the second O electrodes may operate as a receiving line imager. In embodiments, during the transmit mode, the electrical signal pulse may be transmitted from the transmit driver (e.g. 2816-1) to a column of the second O electrodes connected to a conductor (e.g. O12) via a switch (e.g. 2812-1) so that the set of second O electrodes may generate pressure waves. Thus, each column of second O electrodes may operate as a transmit line unit.

In embodiments, the switches 2812, which may be transistor switches, may be set to a neutral position (i.e., they are not coupled to either transmit drivers or amplifiers) during the receive mode. In such a case, only the second set of conductors O12, O22, . . . , On2 may operate during the receive mode.

In embodiments, the transmit driver (e.g. 2816-1) may send a signal to a column of piezoelectric elements (e.g. 2802-11-2802-$m$1) via a conductor (O12) and simultaneously, an amplifier (e.g. 2810-1) may receive electrical charge signal from the same column of piezoelectric elements (e.g. 2802-11-2802-$m$1). In such a case, each piezoelectric element (e.g. 2802-11) in a column may receive a signal from the transmit driver (e.g. 2816-1) through one conductor (e.g. O12) and simultaneously transmit an electrical charge signal to an amplifier (e.g. 2810-1) via another conductor (e.g. O11), i.e., the imaging system 2800 may perform simultaneous transmitting and receiving modes. This simultaneous operation of transmitting and receiving modes may be very advantageous in continuous mode Doppler Imaging, where a high blood flow velocity may be imaged, compared to pulsed Doppler Imaging.

In embodiments, a line unit, which refers to a column of O electrodes electrically coupled to a common conductor, may operate as a transmit unit or a receive unit or both. For instance, electrical signals may be sequentially transmitted to the conductors O12, O22, . . . , On2 so that the line elements sequentially generate pressure waves during the transmit mode, and the reflected pressure waves may be processed and combined to generate a two dimensional image of the target organ in the receive mode. In another example, electrical drive signals may be simultaneously transmitted to the conductors O12, O22, . . . , On2 during the transmit mode and the reflected pressure waves may be processed at the same time using charge generated from conductors O11, O12 to On1 to simultaneously transmit and receive ultrasound to create a two dimensional image. Conductors O12-On2 may also be used to receive charge from the piezoelectric line elements in a receive mode of operation.

Figure 29:
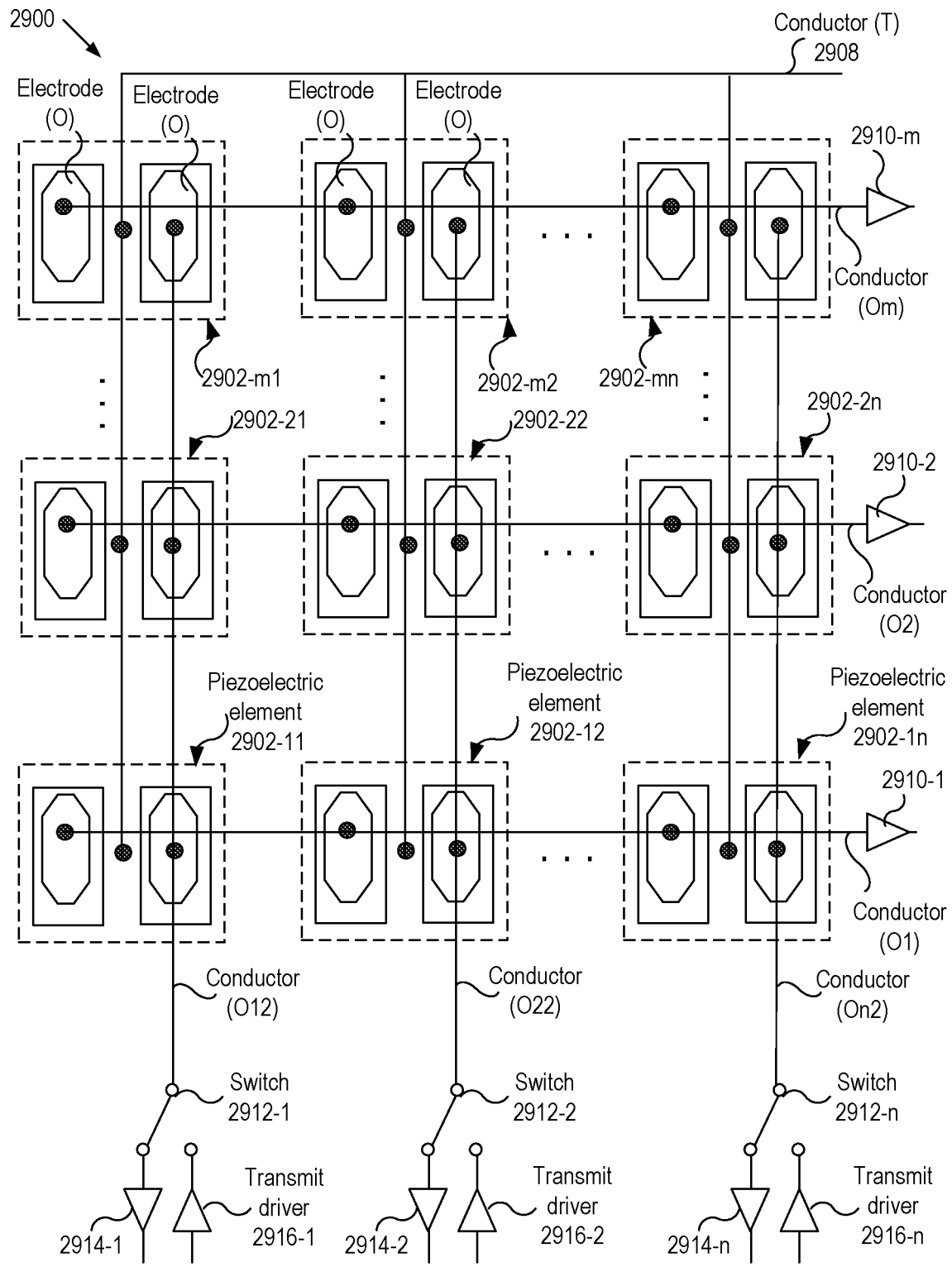
FIG. 29 illustrates a schematic diagram of an imaging system according to embodiments of the present disclosure.

FIG. 29 shows an exemplary embodiment of an imaging system 2900 according to embodiments of the present disclosure. As depicted, the imaging system 2900 includes an array of piezoelectric elements 2902-11-2902-$mn$ and each piezoelectric element may include first and second signal (O) electrodes and a T electrode. In embodiments, all of the T electrodes in the array may be electrically coupled to one common conductor (T) 2908; each row of the first O electrodes may be electrically connected to one of conductors O1-Om; and each column of the second O conductors may be electrically connected to a switch 2912 via one of conductors O12-On2 and. In embodiments, each of the switches 2912-1-2912-$n$ may toggle between a transmit driver (e.g. 2916-1) and an amplifier (e.g. 2914-1), which may be a low noise amplifier. In embodiments, each of the conductors O1-On may be connected to one of the amplifiers 2910-1-2910-$m$, which may be low noise amplifiers.

In embodiments, during the transmit mode, a signal may be transmitted from a transmit driver (e.g. 2916-1) to a column of second O electrodes via a conductor (e.g. O12) so that the column of piezoelectric elements may generate pressure waves as a line unit. During the transmit mode, each switch (e.g. 2912-1) may be toggled to a corresponding transmit driver (e.g. 2916-1).

In embodiments, the imaging system 2900 may process the reflected pressure waves in two different methods. In the first method, the amplifiers 2910-1-2910-$n$ may receive electric charge signals from the first O electrodes, i.e., each amplifier may receive signals from a row of the first O electrodes. This method allows biplane imaging/mode, where for a two dimensional image, the biplane image may provide orthogonal perspectives. Also, this method may provide more than two dimensional imaging capability. The biplane imaging may be helpful for many applications, such as biopsy. It is noted that, in this method, the transmitting and receiving modes may be performed simultaneously. In the second method, the switches 2912 may be toggled to the amplifiers 2914 so that each amplifier may receive and process the electrical charge signals from a corresponding column of the second O electrodes.

In embodiments, a line unit, which refers to a column (or row) of O electrode electrically coupled to an O conductor, may operate as a transmit unit or a receive unit or both. In embodiments, even though the conductors O1-Om are arranged in orthogonal directions to the conductors O12-On2, the directions may be electronically programmed and electronically adjustable. For instance, the gain of the amplifiers 2910 and 2914 may be adjustable electronically, where gain control leads are implemented in the amplifiers. In embodiments, the length of each line elements (i.e., the number of piezoelectric elements in each line element) may also be electronically adjusted. In embodiments, this may be achieved by connecting all signal electrodes of every piezoelectric element to corresponding nodes in the ASIC chip and, where the ASIC programs the connection between the signal electrodes of the elements to be connected to each other, transmit drivers or amplifiers as appropriate.

Figure 30:
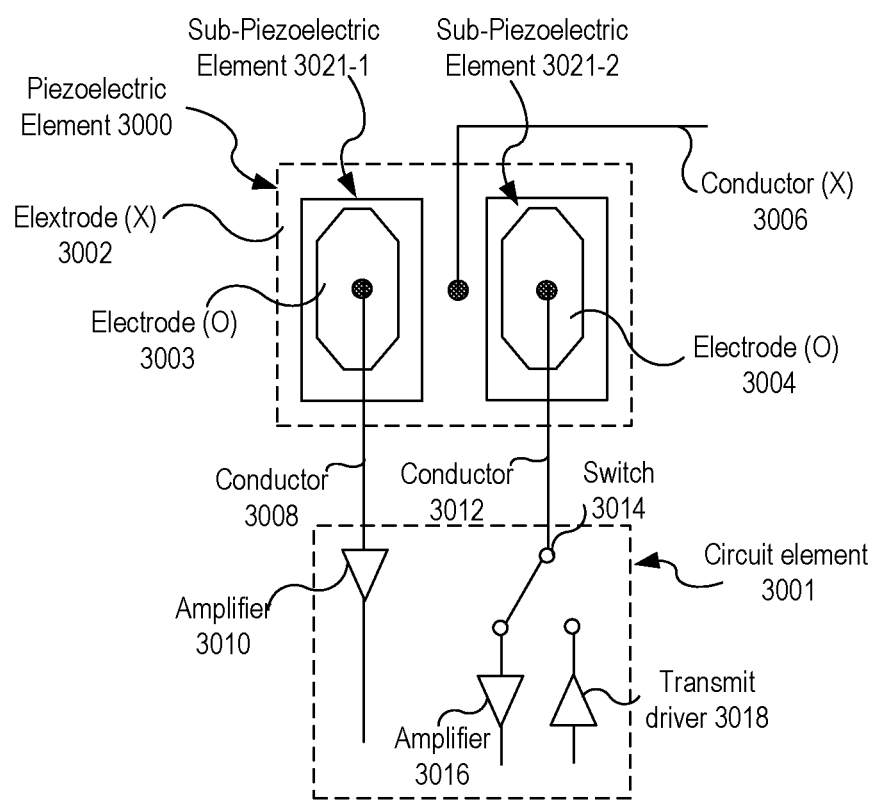
FIG. 30 shows an embodiment of a piezoelectric element coupled to a circuit element according to embodiments of the present disclosure.

FIG. 30 shows an embodiment of a piezoelectric element 3000 coupled to a circuit element 3001 according to embodiments of the present disclosure. As depicted, the piezoelectric element 3000 may include: a first sub-piezoelectric element 3021-1 and a second sub-piezoelectric element 3021-2. The piezoelectric element 3000 may include: a bottom electrode (X) 3002 that is shared by the first and second sub piezoelectric elements and coupled to a conductor (X) 3006. In embodiments, the first sub-piezoelectric element 3021-1 may include a signal (O) electrode 3003 that is electrically coupled to the amplifier 3010 via the conductor 3008. In embodiments, the second sub-piezoelectric element 3021-2 may include a signal (O) electrode 3004 that is electrically coupled to the switch 3014 via the conductor 3012.

In embodiments, a circuit element 3001 may be electrically coupled to the piezoelectric element 3000 and include two amplifiers 3010 and 3016, such as low noise amplifiers, and a transmit driver 3018. In embodiments, the switch 3014 may have one end connected to the O electrode 3004 through the conductor 3012 and the other end that may toggle between the amplifier 3016 for the receive mode and a transmit driver 3018 for the transmit mode. In embodiments, the amplifier 3016 may be connected to other electronics to further amplify, filter and digitize a receive signal, even though an amplifier is used to symbolically represent the electronics. The transmit driver 3018 may be a multi-stage drive and may generate an output with two or more levels of a signaling. The signaling can be unipolar or bipolar. In embodiments, the transmit driver 3018 may include a switch interconnecting an input to an output of a driver under electronic control of the driver, which is not explicitly shown In FIG. 30.

In embodiments, the signal of the transmit driver 3018 may be pulse width modulated (PWM), where, by controlling the pulse widths on a per element basis, a weighting function may be created on a transmitted ultrasound signal. This may for example perform a windowing function, where the transmit signal is weighted by a window function. In embodiments, the weighting coefficients may be achieved by varying the duty cycle of the transmit signal as is done during PWM signaling. This kind of operations may allow for transmit apodization, where the side lobe of a radiated signal are greatly attenuated, allowing for a higher quality image.

In embodiments, a transceiver array may be disposed in a transceiver substrate and include an n×n array of the piezoelectric element 3000 and an n×n array of the circuit elements 3001 may be disposed in an ASIC chip, where each piezoelectric element 3000 may be electrically coupled to a corresponding one of the n×n array of the circuit elements 3001. In such a case, the transceiver substrate may be interconnected to the ASIC chip by $3n^2$ bumps. In embodiments, each column (or row) of piezoelectric element array may be operated a line unit, as discussed in conjunction with FIGS. 28 and 29. For instance, a same pulse may be simultaneously applied to a column of piezoelectric elements so that the column of piezoelectric elements may generate pressure waves simultaneously. It is noted that each piezoelectric element 3000 of the n×n array of piezoelectric elements may be coupled with a corresponding one circuit element 3001 of the n×n array of circuit elements.

In embodiments, the sub-piezoelectric element 3021-1 may be in the receive mode during the entire operational period while the sub-piezoelectric element 3021-2 may be in either transmit or receive mode. In embodiments, the simultaneous operation of transmit and receive modes may allow the continuous mode Doppler imaging.

In embodiments, when the transmit driver 3018 transmits a signal to the electrode 3004, the power levels of the pressure wave generated by the sub-piezoelectric element 3021-2 may be changed by using pulse width modulation (PWM) signaling. This is important, for example, when switching from B mode to Doppler Mode imaging, signal power transmitted into the human body may be long and if power levels are not reduced, tissue damage may occur. Typically, in the conventional systems, different fast settling power supplies are used for B Mode and various Doppler Mode imaging to allow transmit drive voltages to differ in the 2 cases to for example not create excessive power in Doppler mode. Unlike the conventional systems, in embodiments, the power level may be changed by using the PWM signals on the transmit without using the conventional fast settling power supplies. In embodiments, rapid switching between Doppler and B mode imaging is desired to co-image these modes together. In embodiments, the ground electrodes of the piezoelectric element may also be separated from each other and connected to the ground separately. In embodiments, this independent grounding may reduce the noise and result in faster settling times. In embodiments, power transmitted may also be reduced by reducing the height of the transmit columns under electronic control. This again facilitates use of same power supply for both Doppler and B mode and meet power transmission requirements in each mode. This also allows co imaging.

Figure 31:
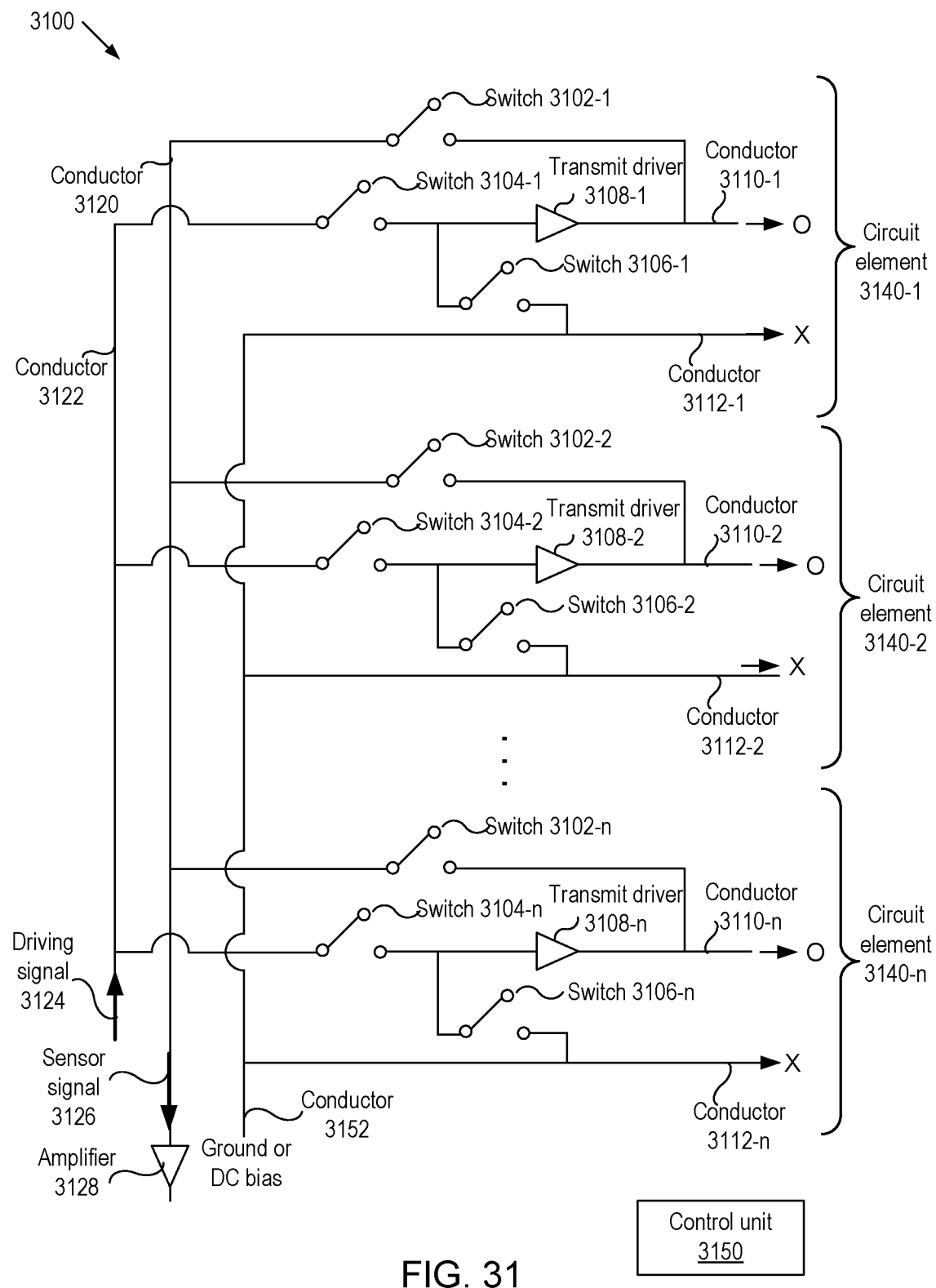
FIG. 31 shows a circuit for controlling multiple piezoelectric element according to embodiments of the present disclosure.

FIG. 31 shows a circuit 3100 for controlling multiple piezoelectric elements according to embodiments of the present disclosure. In embodiments, the circuit 3100 may be disposed in an ASIC chip, where the line (either column or row) of piezoelectric elements that is disposed in a transceiver substrate and the ASIC chip may be interconnected to the transceiver substrate by bumps. As depicted, the circuit 3100 may include an array of circuit elements 3140-1-3140-n, where each circuit element may communicate signals with the O and X electrodes of the corresponding piezoelectric element.

As depicted in FIG. 31, each circuit element (e.g. 3140-1) may include a first switch (e.g. 3102-1), a second switch (e.g. 3104-1), a third switch (e.g. 3106-1), and a transmit driver (e.g. 3108-1). The output from the transmit driver (e.g. 3108-1) may be sent to an O electrode of the piezoelectric element via a conductor (e.g. 3110-1). During the transmit mode, each circuit element may receive a transmit driver (driving) signal 3124 through a conductor 3122. Each second switch (e.g. 3104-1), which may be transistor switches and controlled by a control unit 3150, may be turned on to transmit the signal 3124 to the transmit driver (e.g. 3108-1). (The electrical connections between the control unit 3150 and other components in the circuit 3100 are not shown in FIG. 31.) The transmit driver (e.g. 3108-1) may perform logical decode, level shift, buffer the input signal and send the transit signal to the O electrode via the conductor (e.g. 3110-1). In embodiments, during the transmit mode, the first switch (e.g. 3102-1) may be turned off.

In embodiments, the control unit 3150 may decide which piezoelectric elements need to be turned on during the transmit mode. If the control unit 3150 decides not to turn on a second piezoelectric element, the first switch (e.g. 3102-2) and the second switch (e.g. 3104-2) may be turned off, while the third switch (e.g. 3106-2) may be turned on so that the O and X electrodes have the same electrical potential (i.e., there is a net zero volt drive across the piezoelectric layer). In in embodiments, the third switches 3106 may be optional.

In embodiments, during the receive mode, the first switch (e.g. 3102-1) may be turned on so that the electrical charge developed in the O electrode may be transmitted through the conductors 3110-1 and 3120 to the amplifier 3128. Then, the amplifier 3128 may receive electrical charge signal (or, equivalently, sensor signal) 3126 and amplify the sensor signal, where the amplified signal may be further processed to generate an image. During the receive mode, the second switch (e.g. 3104-1) and the third switch (e.g. 3106-1) may be turned off so that the received signal may not be interfered. It is noted that the entire array of the circuit element 3140-1-3140-n may share a common amplifier 3128, simplifying the design of the circuit 3100. In embodiments, the X electrodes of the piezoelectric elements may be electrically coupled to the ground or a DC bias voltage via the conductors 3112-1-3112-n, where the conductors 3112-1-3112-n may be electrically coupled to a common conductor 3152.

In embodiments, the circuit 3100 may be coupled to a column of piezoelectric elements (e.g. 2002-11-2002-$n$1) in FIG. 20. In embodiments, a plurality of circuits that are similar to the circuit 3100 may be coupled with the multiple columns of piezoelectric elements in the array in FIG. 20, and the conductors 3152 may be coupled to a common conductor (such as 2006 in FIG. 20). In embodiments, the circuit 3100 may control a column of piezoelectric elements in FIGS. 20-27.

Figure 32:
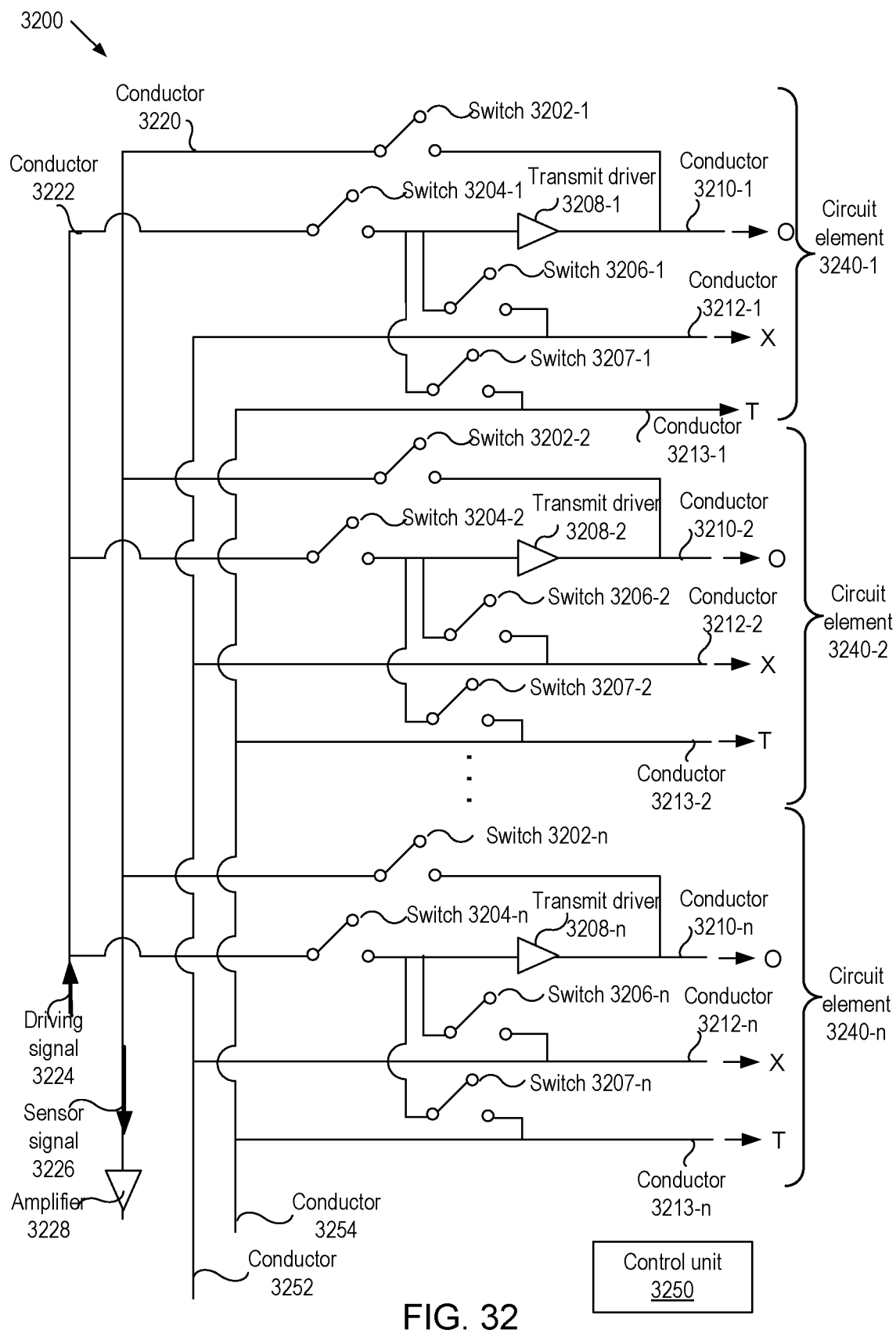
FIG. 32 shows a circuit for controlling multiple piezoelectric element according to embodiments of the present disclosure.

FIG. 32 shows a circuit 3200 for controlling multiple piezoelectric elements according to embodiments of the present disclosure. In embodiments, the circuit 3200 may be disposed in an ASIC chip, where the line (either column or row) of piezoelectric elements that is disposed in a transceiver substrate and the ASIC chip may be interconnected to the transceiver substrate by bumps. As depicted, the circuit 3200 may include an array of circuit elements 3240-1-3240-$n$, where each circuit element may communicate signals with the O, X, and T electrodes of the corresponding piezoelectric element.

As depicted in FIG. 32, each circuit element (e.g. 3240-1) may include a first switch (e.g. 3202-1), a second switch (e.g. 3204-1), a third switch (e.g. 3206-1), a fourth switch (e.g. 3207-1), and a transmit driver (e.g. 3208-1). The output from the transmit driver (e.g. 3208-1) may be sent to an O electrode of the piezoelectric element via a conductor (e.g. 3210-1). During the transmit mode, each circuit element may receive a transmit driver (or driving) signal 3224 through a conductor 3222. Each second switch (e.g. 3204-1), which may be a transistor switch and controlled by a control unit 3250, may be turned on to transmit the signal 3224 to the transmit driver (e.g. 3208-1). (The electrical connection between the control unit 3250 and other components in the circuit 3200 are not shown in FIG. 32.) The transmit driver (e.g. 3208-1) may logically decode the signal, level shift it and buffer, the output signal and send the transmit output signal to the O electrode via the conductor (e.g. 3210-1). In embodiments, during the transmit mode, the first switch (e.g. 3202-1) may be turned off.

In embodiments, the control unit 3250 may decide which piezoelectric elements need to be turned on during the transmit mode. If the control unit 3250 decides not to turn on a second piezoelectric element, the first switch (e.g. 3202-2) and the second switch (e.g. 3204-2) may be turned off, while the third switch (e.g. 3206-2) and the fourth switch (e.g. 3207-2) may be turned on so that the O and X (and T) electrodes have the same electrical potential (i.e., there is a net zero volt drive across the piezoelectric layer). In in embodiments, the third and fourth switches (e.g. 3206-2 and 3207-2 may be optional. It is understood that 3 level signaling and a transmit driver that performs that is not shown explicitly. Similarly the connections to X T conductors and switches like 3206-2, 3207-2 are shown in a simplified manner.

In embodiments, during the receive mode, the first switch (e.g. 3202-1) may be turned on so that the electrical charge developed in the O electrode may be transmitted through the conductors 3210-1 and 3220 to the amplifier 3228. Then, the amplifier 3228 may amplify the electrical charge (or sensor) signal 3226, where the amplified signal may be further processed to generate an image. During the receive mode, the second switch (e.g. 3204-1), the third switch (e.g. 3206-1), and the fourth switch (e.g. 3207-1) may be turned off so that the received signal may not be interfered.

It is noted that the entire array of the circuit element 3240-1-3240-$n$ may share a common amplifier 3228, simplifying the design of the circuit 3200. In embodiments, the X electrodes of the piezoelectric elements may be electrically coupled to the ground or a DC bias voltage via the conductors 3212-1-3212-$n$, where the conductors 3212-1-3212-$n$ may be electrically coupled to a common conductor 3252. In embodiments, the T electrodes of the piezoelectric elements may be electrically coupled to the ground or a DC bias voltage via the conductors 3213-1-3213-$n$, where the conductors 3213-1-3213-$n$ may be electrically coupled to a common conductor 3254.

In embodiments, the circuit 3200 may be coupled to a column of piezoelectric elements (e.g. 2102-11-2102-$n$1) in FIG. 21. In embodiments, a plurality of circuits that are similar to the circuit 3200 may be coupled with the multiple columns of piezoelectric elements in the array in FIG. 21, and the conductors 3252 may be coupled to a common conductor (such as 2106 in FIG. 20). Similarly, in embodiments, the conductors 3254 may be coupled to a common conductor (such as 2108 in FIG. 21). In embodiments, the circuit 3200 may control a column of piezoelectric elements in FIGS. 20-27.

In FIGS. 22-32, conductors are used to electrically couple an electrode to another electrode. For instance, the electrodes 2006-11-2006-$m$1 are electrically coupled to a conductor 2006. In embodiments, the conductors in FIGS. 22-32 may be implemented in a variety of methods, such as metal interconnect layers deposited and patterned on the substrate on which the piezoelectric elements are disposed or on a different substrate, such as ASIC, that is connected to the substrate.

FIGS. 33 and 34 show exemplary waveforms 3300 and 3400 for driving a piezoelectric element during the transmit mode according to embodiments of the present disclosure. In general, piezoelectric material may be vulnerable to damages caused by dielectric aging, and the aging may be delayed or avoided by using unipolar drive signals. The waveforms 3300 and 3400 represent the voltage potential between O and X electrodes and/or between O and T electrodes. As depicted, the waveforms may be unipolar in nature and may be a two level step waveform 3300 (i.e., the transmit driver, such as 2812, 2912, 3018, 3108, 3208, etc. is a unipolar transmit driver) or a multilevel (such as three level) step waveform 3400. The actual voltage amplitude may vary typically from 1.8 V to 12.6 V. In embodiments, the multistep waveform 3400 or a waveform with more steps may reduce heating in the piezoelectric element and have advantages for use during certain imaging modes, such as Doppler or harmonic imaging.

In embodiments, the frequency of the pulses in the waveforms 3300 and 3400 may vary depending on the nature of the signal needed and need to contain the frequency at which membrane underlying the pMUT is responsive to. In embodiments, the waveforms may also be complex signals, such as linear or non-linear frequency modulated chirp signals, or other coded signals using the Golay codes.

In embodiments, the circuits for driving the piezoelectric elements may further be designed such that the transmit output from the underlying membrane may be symmetrical in shape. In embodiments, for each signal pulse in the waveform 3300 (or 3400), the rising edge of the pulse may be substantially symmetrical to the falling edge of the pulse with respect to the center of the pulse. This symmetry lowers the harmonic content of the transmit signal, specially the second harmonic and other even order harmonics signal. In embodiments, the signal pulse in the waveform 3300 (or 3400) may be a pulse width modulated (PWM) signal.

Figure 35:
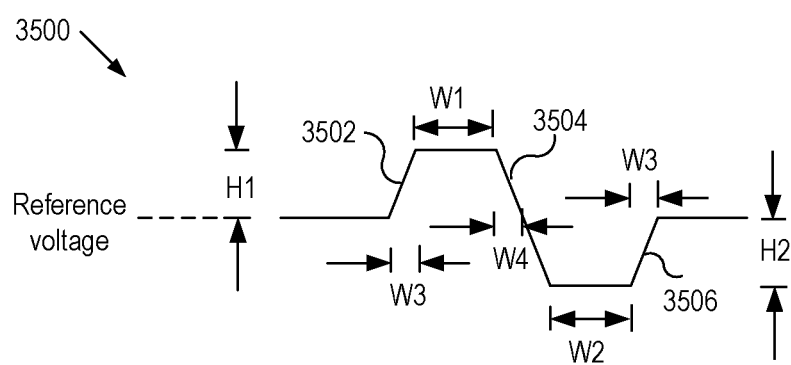
FIG. 35 shows a transmit drive signal waveform according to embodiments of the present disclosure.

FIG. 35 shows a transmit drive signal waveform according to embodiments of the present disclosure. As depicted, the signal 3500 from the transmit driver may be symmetric and bipolar i.e., the magnitude (H1) and width (W1) of the peak maximum voltage are the same as the magnitude (H2) and width (W2) of the peak minimum voltage. Also, the slope of the rising edge 3502 is the same as the slope of the falling edge 3504. In addition, the rising time W3 is the same as the fall time W4, where the fall time W4 refers to the time interval between the starting point of the fall and the reference voltage. Furthermore, the rising edge 3506 has the same slope as the rising edge 3502.

Figure 36:
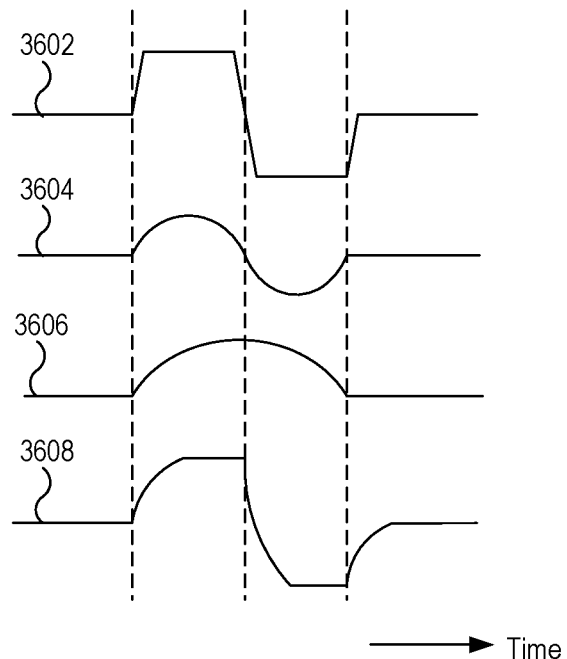
FIG. 36 shows input/output signals of various circuits in an imaging assembly according to embodiments of the present disclosure.

During the transmit operation, the transmit drive, e.g. 3018 in FIG. 30, may be driven by an electrical waveform, such as shown in FIGS. 33-34. FIG. 36 shows output signals of various circuits in an imaging assembly according to embodiments of the present disclosure. In embodiments, the waveform 3602 may be an output signal from the transmit driver, e.g. 3018 and transmitted to a piezoelectric element, e.g. 3000. In embodiments, as the piezoelectric element may have an inherent bandwidth, it may output a sinusoidal output 3604 at its resonant frequency. If the output of the transmit driver connected to the O electrode of the piezoelectric element rises very slowly, it may not be able to charge the electrode to the desired final value and thus may cause low output signals, as shown in waveform 3606, where final amplitude is smaller than in 3602. On the other hand, if the output signal of the transmit driver settles very quickly, the output signal of the transmit driver has larger bandwidth than the bandwidth limit of the piezoelectric element and therefore extra energy may be dissipated in heat. Therefore, in embodiments, as shown in the waveform 3608, the piezoelectric element may be charged at a rate such that it is completely charged but not very quickly. In embodiments, the waveform 3608, which represents the voltage potential across the top and bottom electrodes as a function of time, is closer in shape to the output of the transducer and because difference in shape is smaller, the input signal bandwidth and output signal bandwidth matches better, less loss of energy in heat occurs. In embodiments, drive impedance of transmit driver is optimized to reduce the loss of energy. Stated differently, the impedance of the transmit driver is designed to drive the piezoelectric element optimally with respect to heat dissipation and time constants needed for adequate voltage settling within a target time period.

In embodiments, the imager 120 may use a harmonic imaging technique, where the harmonic imaging refers to transmitting pressure waves on the fundamental frequency of the membrane and receiving reflected pressure waves at second or higher harmonic frequencies of the membrane. In general, the images based on the reflected waves at the second or higher harmonic frequencies have higher quality than the images based on the reflected waves at the fundamental frequency. The symmetry in the transmit waveform may suppress the second or higher harmonic components of the transmit waves, and as such, the interference of these components with the second or higher harmonic waves in the reflected waves may be reduced, enhancing the image quality of the harmonic imaging technique. In embodiments, to reduce the second or higher harmonic waves in the transmit waves, the waveform 3300 may have 50% duty cycle.

In FIGS. 20-29, the arrays may include multiple line units, where each line unit includes a plurality of piezoelectric elements that are electrically coupled to each other. In embodiments, the line units may be driven with multiple pulses that have phase differences (or equivalently delays). By adjusting the phases, the resultant pressure waves may be steered at an angle, which is referred to as beamforming.

Figure 37A:
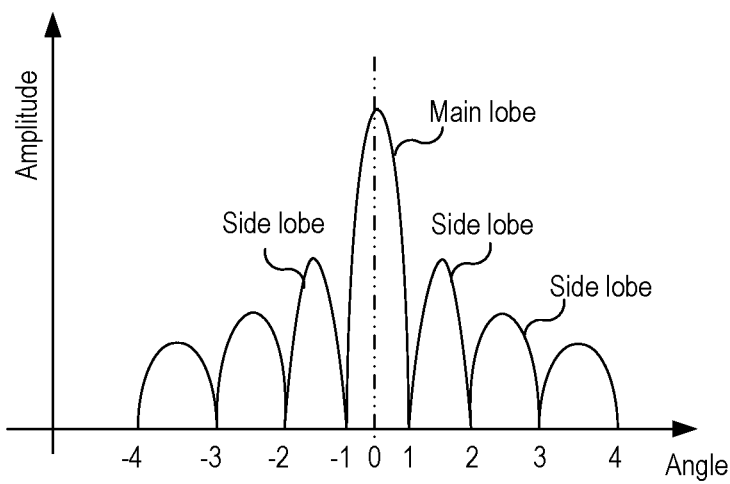
FIG. 37A shows a plot of the amplitude of a transmit pressure wave as a function of angle according to embodiments of the present disclosure.

FIG. 37A shows a plot of the amplitude of a transmit pressure wave as a function of spatial location along the azimuth axis of the transducer according to embodiments of the present disclosure. If the piezoelectric elements in the array are arranged in 2 dimensions and the piezoelectric elements on a column in the Y direction are connected and have many columns along the X direction, the X direction is known as the azimuth direction and the Y direction is known as the elevation direction. As depicted in FIG. 37A, the transmit pressure wave includes the main lobe and multiple side lobes. The main lobe may be used to scan tissue targets and have high pressure amplitude. The side lobes have lower amplitude but degrade quality of images and therefore it is desirable to reduce their amplitude.

Figure 37B:
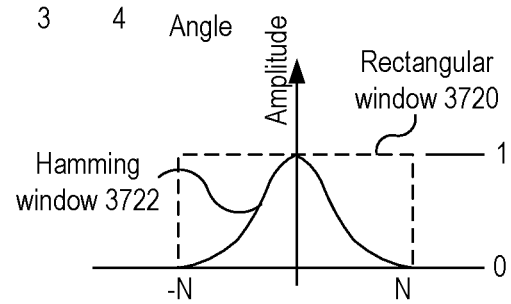
FIG. 37B shows windows for apodization process according to embodiments of the present disclosure.

FIG. 37B shows various types of windows for apodization process according to embodiments of the present disclosure. In FIG. 37B, x-axis represents position of a piezoelectric elements relative to the piezoelectric element at the center of an active window and y-axis represents the amplitude (or, weight applied to the piezoelectric element). As depicted, for the rectangular window 3720, there is no weighting provided for any of the transmit lines, i.e., they are all at a uniform amplitude (i.e. symbolically 1). On the other hand, if the weighting function is implemented, as depicted by the Hamming window 3722, lines at the center get a greater weighting than ones at the edges. For instance, to apply the Hamming window 3722 to the transducer tile 210 in FIG. 3B, the piezoelectric elements in the leftmost column (which is denoted as −N in FIG. 37B) and the piezoelectric elements in the rightmost column (which is denoted as N in FIG. 37B) may have the lowest weight, while the piezoelectric elements in the middle column may have the highest weight. This process is known as apodization. In embodiments, various types of window weighting may be applied, even though the Hamming window 3722 shown is only meant to be one example. In embodiments, apodization may be implemented by a variety of means such as scaling the transmit driver output drive level differently for different lines by employing a digital to analog converter (DAC) or by keeping the same drive level but reducing the number of pixels on a line The net effect is the side lobe level can be reduced by use of apodization, where the weighting of the transmit drive varies based on where a particular line is located within the transmit aperture energized.

In embodiments, the reduction in the voltage of the pulses or waveforms may lower the temperature at the transducer surface. Alternately, for a given maximum acceptable transducer surface temperature, transducers operating at lower voltages may deliver better probe performance, resulting in better quality images. For example, for a probe with 192 piezoelectric elements to reduce power consumption, transmit pressure waves may be generated by using only a portion of probe (i.e., a subset of the piezoelectric elements) and scanning the remaining elements sequentially in time using a multiplexer. Therefore, at any point of time, in the conventional systems, only a portion of the transducer elements may be used to limit the temperature rise. In contrast, in embodiments, the lower voltage probe may allow more piezoelectric elements to be addressed simultaneously, which may enable increased frame rates of the images and enhanced image quality. Significant power is also consumed in the receive path where the received signal is amplified using LNAs. An imaging system typically uses a number of receive channels, with an amplifier per receiver channel. In embodiments, using temperature data, a number of receiver channels can be turned off to save power and reduce temperature.

In embodiments, the apodization may be achieved by varying the number of piezoelectric elements in each line unit according to a window function. In embodiments, such a window approximation may be achieved by electronically controlling the number of piezoelectric elements on a line or by hardwiring the transducer array with the required number of elements.

In general, the heat developed by a probe may be a function of the pulse duration in the transmit pulse/waveform. In general, to make the pressure waves penetrate deep in the target with better signal to noise ratio (SNR), a piezoelectric element may requires long pulse trains. However, this also degrades axial resolution and also generates more heat in the piezoelectric elements. So, in the conventional systems, the number of pulses emitted is small, sometimes one or two. Since longer pulses may create more heat energy, making it impractical for their use in the conventional systems. In contrast, in embodiments, the pulses and waveforms 3300 and 3400 may have significantly lower peak values, which may enables the use of long pulse trains, chirps or other coded signaling. In embodiments, the longer pulse trains do not degrade axial resolution since in the receiver matched filtering is performed to compress the waveform to restore resolution. This technique allows a better signal to noise ratio and allows signal to penetrate deeper into the body and allows for high quality imaging of targets deeper in the body.

In embodiments, a layer of Polydimethylsiloxane (PDMS) or other impedance matching material may be spun over the transducer elements in FIGS. 4-19. This layer may improve the impedance matching between the transducer elements and the human body so that the reflection or loss of pressure waves at the interface between the transducer elements and the human body may be reduced.

In FIGS. 20-29, more than one line unit may be created by connecting pixels in the y-direction (or x-direction), where one line unit (or equivalently line element) refers to multiple piezoelectric elements that are electrically connected to each other. In embodiments, one or more line units may also be created by connecting piezoelectric elements along the x-direction. In embodiments, the piezoelectric elements in a line unit may be hardwired.

As discussed in conjunction with FIG. 18A, each piezoelectric element 1806 may be electrically coupled to a circuit 1842, i.e., the number of piezoelectric elements in the transceiver substrate 1802 is the same as the number of circuit 1842 in the ASIC chip 1804. In such a case, the electrical connections of piezoelectric elements in each column (or row) may be performed electronically, i.e., the hardwire conductors (e.g. 2006) for connecting electrodes in a column (or row) is replaced by electronic switches. Stated differently, the piezoelectric elements in a line imager/unit may be electronically connected to each other. For an electronically controlled line imager, a line imager/unit may be built by connecting each piezoelectric element of a two dimensional matrix array to a corresponding control circuit (such as 1842) of a two dimensional array of control circuits, where the control circuits are located spatially close to pixels. To create a line element, a multiplicity of drivers controlling a column (or row) of pixels may be turned on electronically. In embodiments, the number of drivers in each line imager/unit can be electrically modified under program control and electronically adjustable, i.e., the line imager having the piezoelectric elements are electrically configurable.

In embodiments, smaller capacitance of each pixel may be driven efficiently by the distributed drive circuitry without other equalizing elements in between driver and pixel, eliminating the difficulty of driving a very large line capacitance. In embodiments, driver optimization may allow symmetry in rising edge and falling edges, allowing better linearity in transmit output, enabling harmonic imaging. (The symmetry is described in conjunction with FIGS. 33 and 34.) In embodiments, electronic control may allow programmable aperture size, transmit apodization, and horizontal or vertical steering control, all of which may improve image quality. In embodiments, the configurable line imager/unit under electronic control may be electrically modified under program control. For example, if a smaller number of connected elements is desired in the y-direction, the number may be adjusted by software control and without having to re-spin the control electronic circuitry or the piezoelectric array.

In embodiments, each line unit may be designed to consist of several sub units with separate control for each sub unit. The advantage of these sub units is that it may alleviate the difficulty of driving a large capacitive load for a line unit using one single external transmit driver. For example, if two line units are created in the place of one line unit that includes the entire piezoelectric elements in a column, two different transmit drivers (such as 2816) may be employed and each transmit driver may control half of the load of the full line unit. Also, even if one driver is used, driving the first half of the line unit and the second half of the line unit separately may improve the drive situation due to lower resistance connection to both ends of the line unit.

In embodiments, both the length and orientation of the line units may be controlled. For instance, in FIGS. 20-29, the line units may be arranged in both x and y directions. By way of example, in FIG. 30, the O electrodes along a column (e.g. 2003-11-2003-$n1$) may be electrically coupled to form one line unit, and the O electrodes in the other columns may be electrically coupled to form n number of line units that extend along the x-direction. More specifically, the line units that extend along the x-direction include n number of O electrodes (2003-12-2003-1$n$), . . . , (2003-$n2$-2003-$nn$). In embodiments, the arrangement of line units along orthogonal directions may be possible by controlling the electrical circuits in ASIC chip.

In FIGS. 20-30, each piezoelectric element may include two or more top (X and T) electrodes. In embodiments, the piezoelectric layer under these top electrode may be poled in the same direction or opposite directions. The multiple poling direction when combined with an appropriate applied signal electric field may create improvements in transducer transmit and receive sensitivities and also create additional resonances to enable wider bandwidth.

In FIGS. 20-30, each array may have one or more membranes disposed under the piezoelectric elements. In embodiments, the membranes may have multiple modes of vibration. In embodiments, one membrane may vibrate in the fundamental mode at a certain frequency while another membrane may vibrate at a different frequency determined by membrane design and relative arrangements of electrodes with different poling directions. In embodiments, multiple membranes may be driven by same electrode set and each membrane may have different fundamental frequencies. In embodiments, each membrane may be responsive to a wide range of frequencies, increasing its bandwidth. Also, such a transducer with different poling directions may help increase transmit and receive sensitivities while also enabling a high bandwidth transducer.

In FIGS. 22, 24, 25, the X (or T) electrodes in a column may be electrically coupled to a conductor. In embodiments, these conductors may be electrically coupled to one common conductor. For instance, in FIG. 22, the conductors 2008-1-2208-n may be electrically coupled to one common conductor line so that all of the T electrodes in the array 2200 may be connected to the ground or a common DC bias voltage.

In FIGS. 20-29, each array may include piezoelectric elements that are arranged in a two dimensional array, where the number of elements in the x-direction may be the same as the number of elements in the y-direction. However, it should be apparent to those of ordinary skill in the art that the number of elements in the x-direction may be different from the number of elements in the y-direction.

In embodiments, the ASIC chip (such as 1804) coupled to the transducer substrate (such as 1802) may contain temperature sensors that measure the surface temperatures of the imaging device 120 facing the human body during operation. In embodiments, the maximum allowable temperature may be regulated, and this regulation may limit the functionality of the imaging device since the temperatures should not rise beyond the allowable upper limit. In embodiments, this temperature information may be used to improve image quality. For example, if temperature is below the maximum allowed limit, additional power may be consumed in the amplifiers to lower its noise and improve system signal-to-noise ratio (SNR) for improved quality images.

In embodiments, the power consumed by the imaging device 120 increases as the number of line units that are driven simultaneously increases. All line units in the imaging device 120 may need to be driven to complete transmitting pressure waves from the whole aperture. If only a few line units are driven to transmit pressure waves, wait and receive the reflected echo at a time, it will take more time to complete one cycle of driving the entire line units for the whole aperture, reducing the rate at which images can be taken per second (frame rate). In order to improve this rate, more line units need to be driven at a time. In embodiments, the information of the temperature may allow the imaging device 120 to drive more lines to improve the frame rate.

In FIGS. 20-30, each piezoelectric element may have one bottom electrode (O) and one or more top electrodes (X and T) and have more than one resonance frequency. For instance, each piezoelectric element 2502 in FIG. 25 may have one bottom electrode (O) and two top electrodes, where the first top electrode and the bottom electrode (O) may be responsive to a first frequency f1, while the second top electrode and the bottom electrode (O) may be responsive to a second frequency f2 that may be different from f1.

In embodiments, the electrical charge developed during the receive mode is transferred to an amplifier, such as 1811, 2810, 2814, 2910, 2914, 3010, 3016, 3128, and 3228. Then, the amplified signal may be further processed by various electrical components. As such, it should be apparent to those of ordinary skill in the art that the each of the amplifiers 1811, 2810, 2814, 2910, 2914, 3010, 3016, 3128, and 3228 collectively refers to one or more electrical components/circuits that process the electrical charge signal, i.e., each amplifier symbolically represents one or more electrical components/circuits for processing the electrical charge signal.

Figure 38:
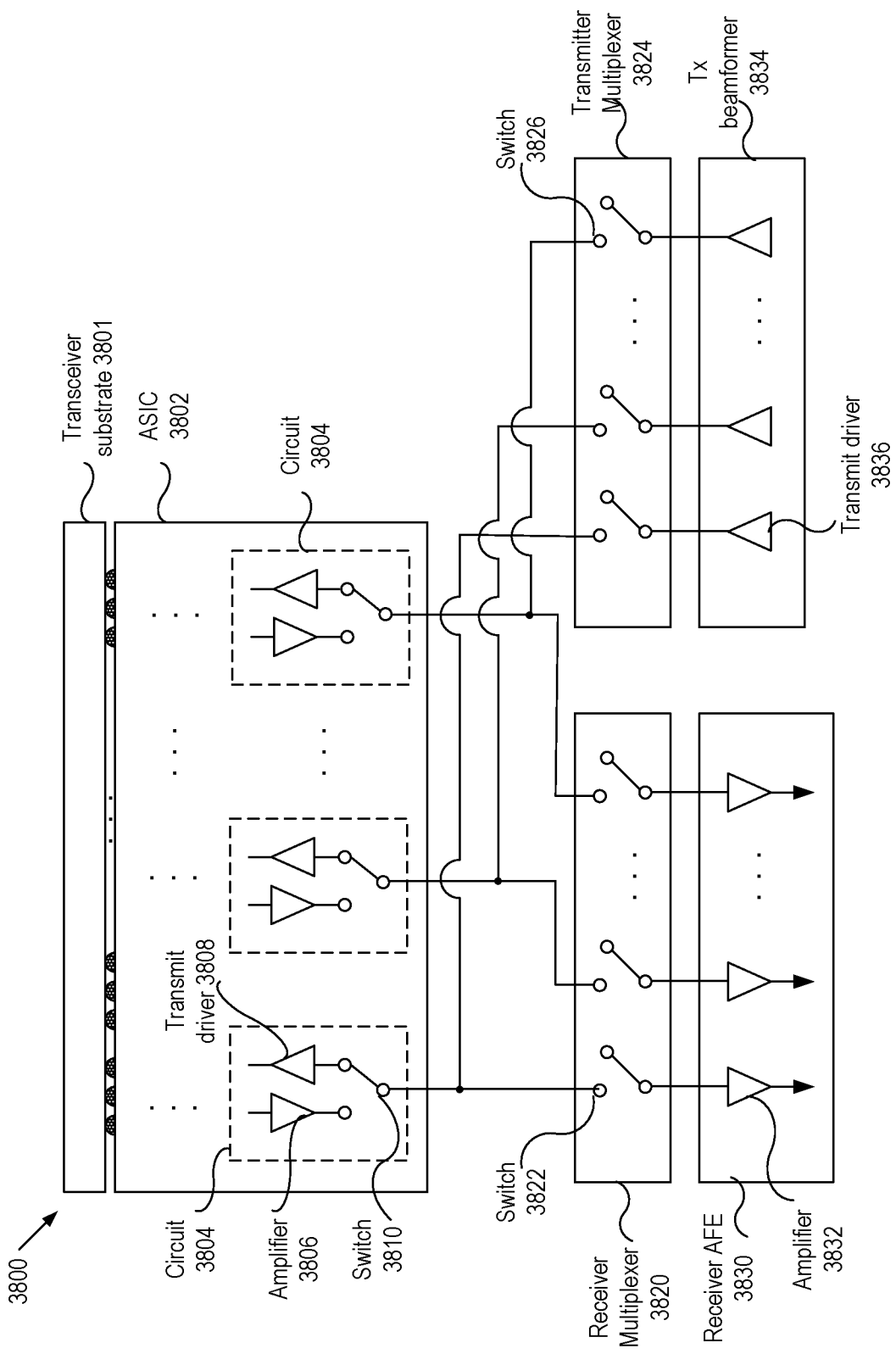
FIG. 38 shows a schematic diagram of an imaging assembly according to embodiments of the present disclosure.

FIG. 38 shows a schematic diagram of an imaging assembly 3800 according to embodiments of the present disclosure. As depicted, the imaging assembly 3800 may include: a transceiver substrate 3801 having piezoelectric elements (not shown in FIG. 38); an ASIC chip 3802 electrically coupled to the transceiver substrate 3801; a receiver multiplexer 3820 electrically coupled to the ASIC chip 3802; a receiver analogue-front-end (AFE) 3830; a transmitter multiplexer 3824 electrically coupled to the ASIC chip 3802; and a transmit beamformer 3834 electrically coupled to the second multiplexer 3824. In embodiments, the ASIC chip 3802 may include multiple circuits 3804 that are connected to and configured to drive multiple piezoelectric elements in the transceiver substrate 3801. In embodiments, each circuit 3804 may include a receiver amplifier (or shortly amplifier) 3806, such as LNA, and a transmit driver 3808 for transmitting a signal to a piezoelectric element, and a switch 3810 that toggles between the amplifier 3806 and the transmit driver 3808. The amplifiers may have programmable gain and means to connect them to piezo elements that need to be sensed. The transmit drivers have means to optimize their impedance and means to be connected to piezoelectric elements that are to be driven.

In embodiments, the receiver multiplexer 3820 may include multiple switches 3822 and the receiver AFE 3830 may include multiple amplifiers 3832. In embodiments, each of the switches 3822 may electrically connect/disconnect a circuit 3804 to/from an amplifier 3832. In embodiments, the transmitter multiplexer 3824 may include multiple switches 3826 and the transmit beamformer 3834 may include multiple transmit driver 3836 and other circuitry not shown to control the relative delay between transmit driver waveform of the various drivers, and other circuitry not shown to control the frequency and the number of pulses for each of the transmit drivers. In embodiments, each of the switches 3826 turn on during a transmit operation and connect to circuit 3804, while switches 3822 turn off, while switch 3810 connects to transmit driver 3808. Similarly, during a receive operation, switches 3826 turn off while switches 3822 turn on, while switch 3810 is connected to amplifier 3806.

In embodiments, the switches 3810 may be toggled to the transmit drivers 3808 during the transmit mode and toggle to the amplifiers 3806 during the receive mode. In embodiments, a portion of the switches 3822 may be closed so that the corresponding circuits 3804 may be set to the receive mode. Similarly, a portion of the switches 3826 may be closed so that the corresponding circuits 3804 may be set to the transmit mode. Since a portion of the switches 3822 and a portion of the switches 3826 may be closed simultaneously, the imager assembly may be operated in both transmit and receive modes simultaneously. Also, the receiver multiplexer 3820 and the transmitter multiplexer 3824 reduce the number of ASIC pins. In embodiments, the receiver multiplexer 3820, receiver AFE 3830, transmitter multiplexer 3824, and transmitter beamformer 3834 may be included in the circuits 215 in FIG. 2.

In embodiments, each piezoelectric may have more than two electrodes, where one electrode may be in the transmit mode to generate pressure waves while the other electrode may be simultaneously in the receive mode to develop electrical charge. This simultaneous operation of transmit and receive modes may allow three dimensional imaging.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. An imaging device, comprising:
a two-dimensional array of piezoelectric elements, each piezoelectric element including:
a piezoelectric layer;
a bottom electrode disposed on a bottom side of the piezoelectric layer; and
a first top electrode disposed on a top side of the piezoelectric layer; and
an application-specific integrated circuit (ASIC) chip comprising an array of driver circuits for driving the two-dimensional array of piezoelectric elements, each of the driver circuits being electrically coupled to a corresponding piezoelectric element;
wherein the two-dimensional array of piezoelectric elements is arranged into columns of piezoelectric elements, a first column includes a portion of the piezoelectric elements of the two-dimensional array, and the first column is activated by simultaneously turning on a portion of the driver circuits that control the portion of the piezoelectric elements in the first column of the two-dimensional array.

2. The imaging device of claim 1, wherein a number of the driver circuits in the ASIC chip is the same as or less than a number of the piezoelectric elements in the two-dimensional array of piezoelectric elements.

3. The imaging device of claim 1, wherein a second column includes another portion of the piezoelectric elements of the two-dimensional array, and the second column is activated by turning on a portion of the driver circuits that control the portion of the piezoelectric elements in the second column of the two-dimensional array, and a number of piezoelectric elements in the first column is different from a number of the piezoelectric elements in the second column.

4. The imaging device of claim 1, wherein the first column of the two-dimensional array of piezoelectric elements is coupled to a transmit driver that applies an electrical signal to the first column so that the piezoelectric elements in the first column emit a pressure wave.

5. The imaging device of claim 1, wherein the first column of the two-dimensional array of piezoelectric elements is coupled to a receive amplifier that receives an electrical signal from the first column and processes the electrical signal.

6. The imaging device of claim 1, wherein each of the driver circuits includes a respective receiver amplifier, the imaging device further comprising:
a multiplexer electrically coupled to the respective receiver amplifiers of each of the driver circuits during a receive mode and configured to multiplex signals from the respective receiver amplifiers.

7. The imaging device of claim 6, further comprising:
a receiver analog-front-end (AFE) electrically coupled to the multiplexer.

8. The imaging device of claim 1, wherein each of the driver circuits includes a respective transmit driver, the imaging device further comprising:
a multiplexer coupled to the respective transmit drivers of each of the driver circuits during a transmit mode and configured to multiplex signals to be sent to the respective transmit drivers.

9. The imaging device of claim 8, further comprising:
a transmit beamformer electrically coupled to the multiplexer.

10. The imaging device of claim 8, wherein a respective impedance of each of the respective transmit drivers is programmable and designed to maximize acoustic power from a transducer without excess heating.

11. The imaging device of claim 1, wherein, during a first period, the columns of piezoelectric elements are driven by transmit drivers, each transmit driver consisting of several circuits on one or more integrated circuits connected by switches under electronic control and wherein, during a second period, each of the columns is connected to a respective receive amplifier consisting of several circuits connected by switches under program control.

12. The imaging device of claim 1, wherein parts of the driver circuits are implemented in a field-programmable gate array (FPGA)-based transmit beamformer.

13. The imaging device of claim 5, wherein the receive amplifier is implemented in an AFE that includes a time-gain amplifier, a low-pass filter, an analog-to-digital converter, and a digital decimator.

* * * * *